(12) United States Patent
Bunnage et al.

(10) Patent No.: US 6,333,330 B1
(45) Date of Patent: *Dec. 25, 2001

(54) PYRAZOLOPYRIMIDINONE CGMP PDE5 INHIBITORS FOR THE TREATMENT OF SEXUAL DYSFUNCTION

(75) Inventors: Mark Edward Bunnage; John Paul Mathias; Graham Nigel Maw; David James Rawson; Stephen Derek Albert Street; Anthony Wood, all of Sandwich (GB)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/426,554

(22) Filed: Oct. 22, 1999

(30) Foreign Application Priority Data

Oct. 23, 1998 (GB) .................................................. 9823102

(51) Int. Cl.⁷ ........................ A61K 31/505; C07D 487/04
(52) U.S. Cl. ............................................. 514/258; 544/262
(58) Field of Search ............................ 544/262; 514/258

(56) References Cited

U.S. PATENT DOCUMENTS

| | | | |
|---|---|---|---|
| 4,371,843 | 2/1983 | Roger et al. | 540/575 |
| 4,663,326 | 5/1987 | Hamilton | 514/258 |
| 4,666,908 | 5/1987 | Hamilton | 514/229 |
| 5,250,534 | * 10/1993 | Bell et al. | 514/258 |
| 5,272,147 | 12/1993 | Bell et al. | 514/234.2 |
| 5,294,612 | 3/1994 | Bacon et al. | 514/234.2 |
| 5,346,901 | 9/1994 | Bell et al. | 514/258 |
| 5,426,107 | 6/1995 | Bell et al. | 514/234.2 |
| 5,719,283 | 2/1998 | Bell et al. | 544/262 |
| 5,734,053 | 3/1998 | Terrett | 544/277 |
| 5,736,548 | * 4/1998 | Bacon et al. | 514/258 |
| 5,955,611 | 9/1999 | Dunn et al. | 544/262 |

FOREIGN PATENT DOCUMENTS

| | | | |
|---|---|---|---|
| 0210188 | 2/1987 | (EP) | H01R/43/20 |
| 0349239 | 1/1990 | (EP) | C07D/487/04 |
| 0352960 | 1/1990 | (EP) | C07D/473/30 |
| 0463756 | 1/1992 | (EP) | C07D/487/04 |
| 0636626 | 2/1995 | (EP) | C07D/487/04 |
| 0526004 | 8/1997 | (EP) | C07D/487/04 |
| 0995750 | 4/2000 | (EP) | C07D/487/04 |
| WO9306104 | 4/1993 | (WO) | C07D/487/04 |
| WO9307149 | 4/1993 | (WO) | C07D/487/04 |
| WO9312095 | 6/1993 | (WO) | C07D/239/91 |
| WO 9315062 | 8/1993 | (WO) | C07D/241/04 |
| WO9400453 | 1/1994 | (WO) | C07D/473/30 |
| WO9405661 | 3/1994 | (WO) | C07D/471/04 |
| WO9428902 | 12/1994 | (WO) | A61K/31/505 |
| WO9616644 | 6/1996 | (WO) | A61K/31/00 |
| WO9616657 | 6/1996 | (WO) | A61K/31/505 |
| WO9628429 | 9/1996 | (WO) | C07D/239/70 |
| WO9628448 | 9/1996 | (WO) | C07D/487/04 |
| WO9849166 | 11/1998 | (WO) | C07D/487/04 |
| WO 9954333 | 10/1999 | (WO) | C07D/487/04 |
| WO9954333 | 10/1999 | (WO) | C07D/487/04 |
| WO 9964004 | 12/1999 | (WO) | A61K/31/505 |

OTHER PUBLICATIONS

J. Med. Chem., 1996, 39, 1635.
Abstract 08253484.
Dumaitre et al., J. Med. Chem., 1996, V. 39(8), pp. 1635–1644.
Harriet W. Hamilton, J. Med. Chem., 1987, 30, pp. 91–96.
Czarmiecki et al in Annual Reports in Medicinal Chemistry, 31, 61–70.
Henze et al. J. Am. Chem. Soc., Feb., 1939, pp. 433–435.
Terfort et al., J. Chem. Soc. Perkin Trans. 1, 1996, pp. 1467–1479.

* cited by examiner

Primary Examiner—Richard L. Raymond
Assistant Examiner—Hong Liu
(74) Attorney, Agent, or Firm—Peter C. Richardson; Gregg C. Benson; James T. Jones

(57) ABSTRACT

There is provided compounds of formula IA and of formula IB,

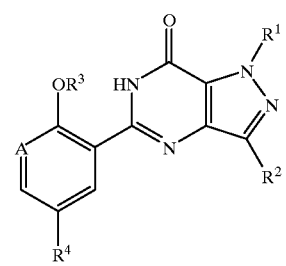

IA

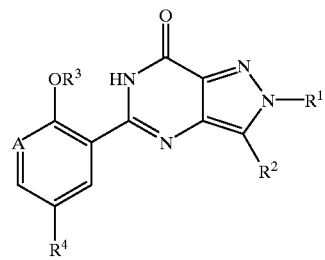

IB wherein $R^1$, $R^2$, $R^3$, $R^4$ and A have meanings given in the description, which are useful in the curative and prophylactic treatment of medical conditions for which inhibition of a cyclic guanosine 3',5'-monophosphate phosphodiesterase (e.g. cGMP PDE5) is desired.

11 Claims, No Drawings

PYRAZOLOPYRIMIDINONE CGMP PDE5 INHIBITORS FOR THE TREATMENT OF SEXUAL DYSFUNCTION

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterases (cGMP PDE5). The compounds therefore have utility in a variety of therapeutic areas, including male erectile dysfunction (MED).

PRIOR ART

International patent application WO 94/28902 discloses the use of certain pyrazolopyrimidinone compounds in the treatment of impotence.

DISCLOSURE OF THE INVENTION

According to a first aspect of the invention there is provided compounds of formulae IA and IB:

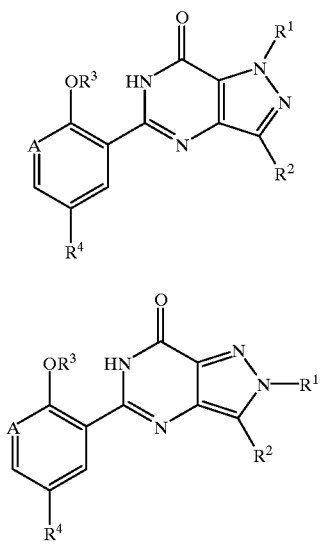

wherein
A represents CH or N;
$R^1$ represents H, lower alkyl, Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;
$R^2$ represents $C(O)NR^{12}R^{13}$, $C(O)OR^{12}$, $NR^{12}R^{13}N(H)$ $SO_2R^{12}$, $N(H)SO_2NR^{12}R^{13}$, $N(H)C(O)R^{12}$, $OR^{12a}$, lower alkyl (which alkyl group is interrupted by one or more of O, S or $N(R^{12})$ and/or substituted or terminated by $C(O)$ $NR^{12}R^{13}$, $C(O)OR^{12}$ or aryl or $Het^1$), cyano, aryl or $Het^1$;
$R^3$, $R^{12}$ and $R^{13}$ independently represent H or lower alkyl, which alkyl group is optionally substituted and/or optionally terminated by one or more substituents selected from aryl, Het, halo, cyano, nitro, $OR^5$, $C(O)R^6$, $C(O)OR^7$, $C(O)NR8R9$, $NR^{10a}R^{10b}$ and $SO_2NR^{11a}R^{11b}$;
$R^4$ represents $SO_2NR^{14}R^{15}$;
$R^{14}$ and $R^{15}$, together with the nitrogen to which they are attached, form Het;

Het represents an optionally substituted four- to twelve-membered heterocyclic group, which group contains at least one nitrogen atom and, optionally, one or more further heteroatoms selected from nitrogen, oxygen and sulphur;
$Het^1$ represents an optionally substituted four- to twelve-membered heterocyclic group, which group contains at least one nitrogen atom or at least one oxygen atom and, optionally, one or more further heteroatoms selected from nitrogen, oxygen and sulphur; and
$R^5$, $R^6$, $R^7$, $R^8$, $R^9$, $R^{11a}$, $R^{11b}$ and $R^{12a}$ independently represent, at each occurrence when used herein, H or lower alkyl;
$R^{10a}$ and $R^{10b}$, at each occurrence when used herein, either independently represent, H or lower alkyl or, together with the nitrogen atom to which they are attached, represent azetidinyl, pyrollidinyl or piperidinyl; or a pharmaceutically, or a veterinarily, acceptable derivative thereof; which compounds are referred to together hereinafter as "the compounds of the invention".

The term "aryl", when used herein, includes six- to ten-membered carbocyclic aromatic groups, such as phenyl and naphthyl. Each "aryl" group identified herein is optionally substituted with one or more substituents selected from halo, cyano, nitro, lower alkyl, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{12}$.

The terms "Het" and "$Het^1$", when used herein, include four- to twelve-membered, preferably four- to ten-membered, ring systems, which may be wholly or partly aromatic in character. Each "Het/$Het^1$" group identified herein is optionally substituted with one or more substituents selected from halo, cyano, nitro, lower alkyl (which alkyl groups may itself be optionally substituted or terminated as defined below), $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{12}$. The term thus includes groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, benzodioxalyl, pyrazolyl, imidazopyridinyl, furanyl, tetrahydrofuranyl and piperazinyl, e.g. 4-$R^{16}$-piperazinyl, wherein $R^{16}$ represents H or lower alkyl, which latter group is optionally substituted or terminated by one or more substituents selected from aryl, Het, halo, cyano, nitro, $OR^5$, $C(O)R^6$, $C(O)OR^7$, $C(O)$ $NR^8R^9$, $NR^{10a}R^{10b}$, $SO_2NR^{11a}R^{11b}$ and $N(H)SO_2R^{12}$.

"Het" and "$Het^1$" groups may also be in the form of an N-oxide.

Azetidinyl, pyrollidinyl and piperidinyl groups that $R^{10a}$, $R^{10b}$ and the nitrogen atom to which they are attached may together represent may also be substituted with one or more substituents selected from halo, cyano, nitro, lower alkyl (which alkyl groups may itself be optionally substituted or terminated as defined below), $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{12}$.

For the avoidance of doubt, the nitrogen atom to which $R^{14}$ and $R^{15}$ are attached is the nitrogen atom that must be present in the relevant Het group.

The term "lower alkyl", when used herein, includes $C_{1-6}$ alkyl. Alkyl groups which $R^1$, $R^2$, $R^3$, $R^5$, $R^6$, $R^7$, $R^{8,}$ $R^9$, $R^{10a}$, $R^{10b}$, $R^{11a}$, $R^{11b}$, $R^{12}$, $R^{12a}$, $R^{13}$ and $R^{16}$ may represent, and with which $R^1$, $NR^{10a}R^{10b}$, aryl, Het and $Het^1$ may be substituted, may, when there is a sufficient number of carbon atoms, be linear or branched, be saturated or unsaturated, be cyclic, acyclic or part cyclic/acyclic, be interrupted by oxygen, and/or be substituted by one or more halo atom.

The terms "alkylHet" and "alkylaryl" include $C_{1-6}$ alkylHet and $C_{1-6}$ alkylaryl. The alkyl groups (e.g. the $C_{1-6}$ alkyl groups) of alkylHet and alkylaryl may, when there is a sufficient number of carbon atoms, be linear or branched, be saturated or unsaturated, and/or be interrupted by oxygen. When used in this context, the terms "Het" and "aryl" are as defined hereinbefore.

Halo groups, with which $R^1$, $R^3$, $R^{12}$, $R^{13}$, $R^{16}$, aryl, Het, $Het^1$ and above-mentioned allyl groups may be substituted or terminated, include fluoro, chloro, bromo and iodo.

The term "pharmaceutically, and veterinary, acceptable derivative" includes salts and solvates. Salts which may be mentioned include: acid addition salts, for example, salts formed with inorganic acids such as hydrochloric, hydrobromic, sulphuric and phosphoric acid, with carboxylic acids or with organo-sulphonic acids; base addition salts; metal salts formed with bases, for example, the sodium and potassium salts. Pharmaceutically acceptable derivatives also include $C_1$ to $C_4$ alkyl ammonium salts.

Preferred compounds of the invention include those wherein:

$R^1$ represents H, a linear, branched, cyclic, acyclic and/or part cyclic/acyclic lower alkyl group, alkylHet, or alkylaryl;

$R^2$ represents a linear or branched, optionally unsaturated lower allyl group (which alkyl group is optionally interrupted by one or more of O, S or $N(R^{12})$), $C(O)NR^{12}R^{13}$, $NR^{12}R^{13}$, $N(H)C(O)R^{12}$, $OR^{12a}$, aryl or $Het^1$;

$R^3$ represents linear, branched, cyclic and/or acyclic lower alkyl which is optionally substituted or terminated by one or more substituents selected from Het or $OR^5$;

$R^{12}$ and $R^{13}$ independently represent H, or linear or branched lower alkyl, provided that, in the case where $R^2$ represents $NR^{12}R^{13}$, $R^{12}$ and $R^{13}$ do not both represent H;

$R^{14}$ and $R^{15}$, together with the nitrogen to which they are attached represent 4-$R^{16}$-piperazinyl, in which $R^{16}$ is as hereinbefore defined.

More preferred compounds of the invention include those wherein:

$R^1$ represents H; a linear or part cyclic/acyclic $C^1$–$C_6$ alkyl group; $C_1$–$C_2$ alkylphenyl, the phenyl group of which is optionally substituted by one or more halo atoms; or $C_1$–$C_3$ alkylHet, in which Het represents a six-membered heterocyclic group;

$R^2$ represents a linear or branched, optionally unsaturated, $C_{1-6}$ alkyl group (which alkyl group is optionally interrupted by one or more of O or $N(R^{12})$), $C(O)NR^{12}R^{13}$, $NR^{12}R^{13}$, $N(H)C(O)R^{12}$, $R^{12a}$, an optionally substituted phenyl group, or an optionally substituted $Het^1$ group (e.g. a pyridinyl, benzodioxazolyl, furanyl, tetrahydrofuranyl, imidazolopyridinyl, pyrazolyl, oxadiazolyl pyrimidinyl or pyrazinyl group);

$R^3$ represents linear or branched $C_1$–$C_4$ alkyl, which is optionally terminated by one or more substituents selected from pyridinyl or $OR^5$, in which $R^5$ represents H or $C_1$–$C_3$ alkyl;

$R^{12}$ and $R^{13}$ independently represent H or linear or branched $C_1$–$C_3$ alkyl, provided that, in the case where $R^2$ represents $NR^{12}R^{13}$, $R^{12}$ and $R^{13}$ do not both represent H;

$R^{12a}$ represents $C_{1-3}$ alkyl;

$R^{14}$ and $R^{15}$, together with the nitrogen to which they are attached, represent 4-$R^{16}$-piperazinyl, in which $R^{16}$ represents a linear or branched $C_1$–$C_3$ alkyl group which is optionally terminated by OH.

Particularly preferred compounds of the invention include those wherein: $R^1$ represents H, a linear or part cyclic $C_1$–$C_5$ alkyl group (e.g. methyl, ethyl, propyl or cyclobutylmethyl), $CH^2$phenyl, $CH_2$(bromophenyl) (e.g. $CH_2$(4-bromophenyl)), $C_1$–$C_2$ alkylHet, in which Het represents pyridin-2-yl, pyridin-3-yl, pyridin-4-yl, pyrimidin-2-yl or morpolin-4-yl;

$R^2$ represents a linear or branched, optionally unsaturated, $C_{1-4}$ alkyl group (which alkyl group is optionally interrupted by an oxygen atom or an $N(R^{12})$ group), $C(O)NR^{12}R^{13}$, $NR^{12}R^{13}$, $N(H)C(O)R^{12}$, $OR^{12a}$, phenyl (optionally substituted by one or more substituent (e.g. one or more of $C_{1-3}$ alkyl, $C_{1-3}$ alkoxy (which latter two groups are optionally substituted by one or more halo atom and/or optionally interrupted by an oxygen atom), halo and cyano)), pyridin-2-yl, pyridin-3-yl, pyrimidin-5-yl, pyrazin-2-yl (which latter four groups are optionally substituted (e.g. by one or more halo, $C_{1-3}$ alkyl, $C_{1-3}$ alkoxy or $NR^{10a}R^{10b}$ groups)), furan-2-yl, furan-3-yl, tetrahydrofuran-2-yl, tetrahydrofuran-3-yl, benzodioxalyl, imidazolo[1,2-a]pyridin-6-yl (which latter six groups are optionally substituted), pyrazol4-yl or 1,3,4-oxadiazol-2-yl (which latter two groups are optionally substituted (e.g. by one or more $C_{1-3}$ alkyl groups));

$R^3$ represents $C^2$–$C_4$ alkyl optionally terminated with $OC_1$–$C_2$ alkyl or pyridin-2-yl; $R^{10a}$ and $R^{10b}$ independently represent H or $C_{1-2}$ alkyl or, together with the nitrogen atom to which they are attached, represent azetidinyl;

$R^{12}$ and $R^{13}$ independently represent H, methyl or ethyl, provided that, in the case where $R^2$ represents $NR^{12}R^{13}$, $R^{12}$ and $R^{13}$ do not both represent H;

$R^{12a}$ represents methyl or ethyl;

$R^{14}$ and $R^{15}$, together with the nitrogen to which they are attached represent 4-$R^{16}$-piperazinyl, in which $R^{16}$ represents methyl or ethyl, the latter of which is optionally terminated with OH.

Most preferred compounds of the invention include the compounds of the Examples described hereinafter.

According to a further aspect of the invention there is provided a compound of formula IA or IB as hereinbefore defined, provided that:

(a) $R^2$ does not represent $OR^{12a}$ or lower alkyl substituted or terminated by $Het^1$;

(b) $Het^1$ represents Het;

(c) $R^{10a}$ and $R^{10b}$ do not, together with the nitrogen atom to which they are attached, represent azetidinyl, pyrollidinyl or piperidinyl;

(d) alkyl groups, as defined herein, are not substituted by one or more halo atom.

The compounds of the invention may exhibit tautomerism. All tautomeric forms of the compounds of formulae IA and IB, and mixtures thereof, are included within the scope of the invention.

The compounds of the invention may also contain one or more asymmetric carbon atoms and may therefore exhibit optical and/or diastereoisomerism. Diastereoisomers may be separated using conventional techniques e.g. by fractional crystallization or chromatography. The various stereoisomers may be isolated by separation of a racemic or other mixture of the compounds using conventional techniques e.g. fractional crystallization or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallization of the diastereoisomeric salts formed by reaction of the racemate with a suitable optically active acid or base. All stereoisomers are included within the scope of the invention.

Also included within the scope of the invention are radiolabelled derivatives of compounds of formulae IA and IB which are suitable for biological studies.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae IA and IB may be prepared by cyclization of corresponding compounds of formulae IIA and IIB, respectively:

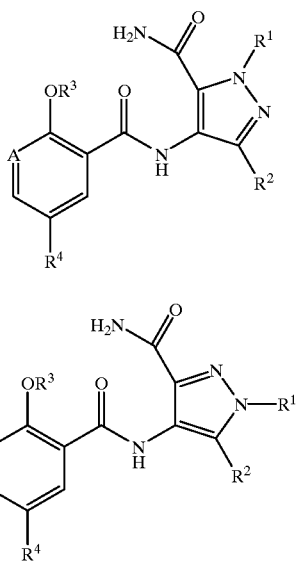

wherein $R^1$, $R^2$, $R^3$, $R^4$ and A are as defined previously for compounds of formulae IA and IB.

This cyclization may be accomplished under basic, neutral or acidic conditions using known methods for pyrimidone ring formation. Preferably, the cyclization is performed under basic conditions using an alkali metal salt of an alcohol or amine, such as potassium tert-butoxide or potassium bis(trimethylsilyl) amide, in the presence of a suitable solvent is (e.g. an alcohol), for example at elevated (e.g. reflux) temperature (or, if a sealed vessel is employed, at above reflux temperature). The skilled person will appreciate that, when an alcohol is selected as solvent, an appropriate alcohol of formula $R^3OH$, or a sterically hindered alcohol, e.g. iso-propanol or 3-methyl pentan-3-ol, may be used if it is intended to mitigate alkoxide exchange at either the 2-position of the pyridin-3-yl, or the phenyl, substituent.

Compounds of formulae IIA and IIB may be prepared by reaction of corresponding compounds of formulae IIIA and IIIB, respectively:

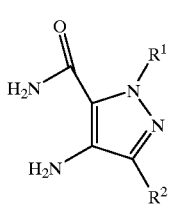

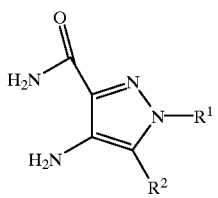

wherein $R^1$ and $I^2$ are as defined previously for compounds of formulae IIA and IIB, with a compound of formula IV or a carboxylic acid derivative thereof:

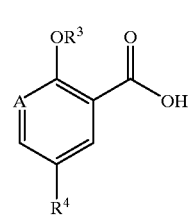

wherein $R^3$, $R^4$ and A are as defined previously for compounds of formulae IIA and IIB.

This coupling reaction may be achieved by conventional amide bond forming techniques which are well known to those skilled in the art. For example, an acyl halide (e.g. chloride) derivative of a compound of formula IV may be reacted with a compound of formula IIIA or IIIB in the presence of an excess of a tertiary amine, such as triethylamine or pyridine, optionally in the presence of a suitable catalyst, such as 4-dimethylaminopyridine, in a suitable solvent such as dichloromethane, at a temperature of about 0° C. to room temperature.

A variety of other amino acid coupling methodologies may be used to couple the compound of formula IIIA or IIIB with the compound of formula IV. For example, the acid of formula IV or a suitable salt thereof (e.g. sodium salt) may be activated with an appropriate activating reagent, e.g. a carbodiimide, such as 1,3-dicyclohexylcarbodiimide or 1-(3-dimethylaminopropyl)-3-ethylcarbodiimide hydrochloride optionally in the presence of 1-hydroxybenzotriazole hydrate and/or a catalyst such as 4-dimethylaminopyridine; a halotrisaminophosphonium salt such as bromotris(pyrrolidino)phosphonium hexafluorophosphate; or a suitable pyridinium salt such as 2-chlorol-1-methyl pyridinium chloride. Either type of coupling reaction may be conducted in a suitable solvent such as dichloromethane or tetrahydrofuran, optionally in the presence of a tertiary amine such as N-methylmorpholine or N-ethyldiisopropylamine (for example when either the compound of formula IIIA or IIIB, or the activating agent is presented in the form of an acid addition salt), at from about 0° C. to about room temperature. Preferably, from about 1 to 2 molecular equivalents of the activating reagent and from 1 to 3 molecular equivalents of any tertiary amine present may be employed.

Alternatively, the carboxylic acid function of IV may be activated using an excess of a reagent such as N,N'-carbonyldiimidazole in an appropriate solvent, e.g. ethyl acetate, dichloromethane or butan-2-one, at from about room temperature to about 80° C., followed by reaction of the intermediate imidazolide with a compound of the formula IIIA or IIIB at from about 20° C. to about 90° C.

In a further variation, a compound of formula IA or IB in which A is CH may be formed in a one-pot procedure by coupling a compound of formula IIIA or IIIB with an acyl chloride derivative of a compound of formula IV and by cyclising the resultant intermediate compound of formula IIA or IIB, using the methods as described previously. The one-pot procedure may further involve an in-situ coupling and cyclization reaction to form a compound of formula IA or IB. Preferably, pyridine may serve as an acid scavenger and as the solvent for the in-situ coupling and cyclization reaction.

2. Compounds of formulae IA and IB, in which $R^2$ represents $C(O)NR^{12}R^{13}$, and $R^{12}$ and $R^{13}$ are as defined previously for compounds of formulae IA and IB, may be prepared by reaction of corresponding compounds of formulae IA and IB, in which $R^2$ represents C(O)OH (or a carboxylic acid derivative thereof) with a compound of formula $HNR^{12}R^{13}$, in which $R^{12}$ and $R^{13}$ are as previously defined for compounds of formula e IA and IB.

This reaction may be accomplished using analogous amide bond forming techniques to those previously described for compounds of formulae IIA and IIB. Alternatively, when $R^{12}$ and $R^{13}$ both represent hydrogen and A represents CH, the coupling reaction may be performed by reaction with ammonia in methanol, at 100° C. under pressure.

3. Compounds of formulae IA and IB, in which $R^2$ represents $C(O)OR^{12}$, may be prepared by cyclization of corresponding compounds of formulae VIA and VIB, respectively:

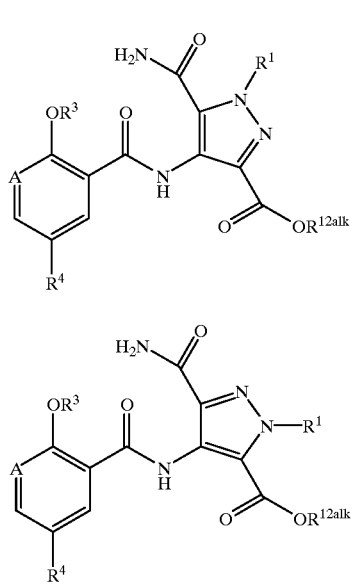

wherein $R^1$, $R^3$, $R^4$ and A are as defined previously for compounds of formulae IA and IB, and $R^{12alk}$ represents an optionally substituted lower allyl group, as defined hereinbefore, followed by removal of the alkyl group $R^{12alk}$ (if required) by hydrolysis and/or (if required) exchange with a further optionally substituted alkyl group.

Typically, the cyclization reaction is accomplished using analogous methods to those previously described for compounds of formulae IIA and IIB.

Compounds of formulae VIA and VIB may be prepared by reaction of corresponding compounds of formulae VIIA and VIIB, respectively:

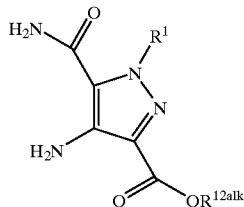

VIIA

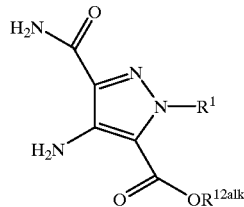

VIIB wherein $R^1$ and $R^{12alk}$ are as defined previously for compounds of formulae VIA and VIB, with a compound of formula IV as defined hereinbefore.

The reaction may be accomplished using analogous amide coupling conditions to those described previously in relation to compounds of formulae IIA and IIB.

4. Compounds of formulae IA and IB may alternatively be prepared by reaction of corresponding compounds of formulae VIIIA and VIIIB, respectively:

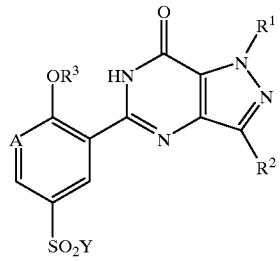

VIIIA

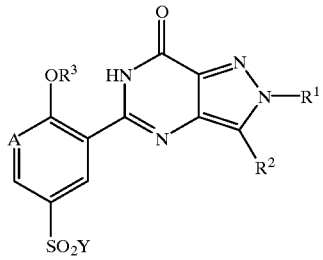

VIIIB wherein Y is a leaving group, such as halo, preferably chloro, bromo or iodo, and $R^1$, $R^2$, $R^3$ and A are as previously defined for compounds of formulae IA and IB, with a compound of formula IX:

$R^{14}R^{15}NH$    IX wherein $R^{14}$ and $R^{15}$ are as previously defined for compounds of formulae IA and IB.

This reaction is typically performed at from 0° C. to room temperature, in the presence of an appropriate solvent, such as a $C_1$ to $C_3$ alcohol or dichloromethane, using an excess of the compound of formula IX and, optionally, in the presence of another suitable base, such as triethylamine.

Compounds of formula VIIIA and VIIIB, in which A represents N, may be prepared from corresponding compounds of formulae XA and XB, respectively:

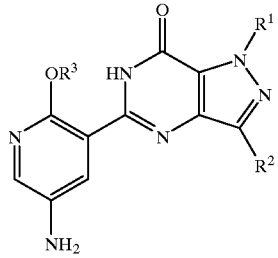

XA

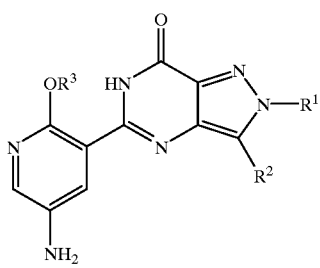

XB wherein $R^1$, $R^2$ and $R^3$ are as previously defined for compounds of formulae VIIIA and VIIIB, using methods known to those skilled in the art for converting an amino group to an $SO_2Y$ group, in which Y is as previously defined for compounds of formulae VIIIA and VIII. For example, compounds of formulae VIIIA and VIIIB in which Y is chloro may be prepared by reacting a corresponding compound of formula XA or XB with about a 1.5 to 2-fold excess of sodium nitrite in a mixture of concentrated hydrochloric acid and glacial acetic acid, at from about −25° C. to about 0° C., followed by treatment with excess liquid sulphur dioxide and a solution of about a three-fold excess of cupric chloride in aqueous acetic acid, at from about −30° C. (e.g. −15° C.) to about room temperature.

Compounds of formulae XA and XB may be prepared by cyclization of corresponding compounds of formulae XIA and XIB, respectively:

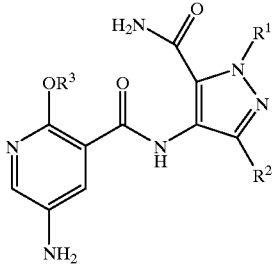

XIA

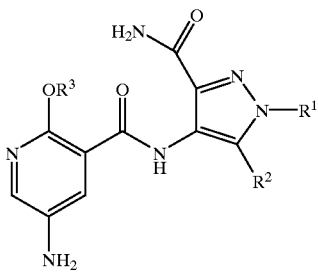

XIB wherein $R^1$, $R^2$ and $R^3$ are as previously defined for compounds of formulae XA and XB. This cyclization may be carried out using similar techniques to those described hereinbefore for the preparation of compounds of formulae IIA and IIB, but it is preferably base mediated.

Compounds of formulae XIA and XIB may be prepared by the reduction of corresponding compounds of formulae XIIA and XIIB, respectively:

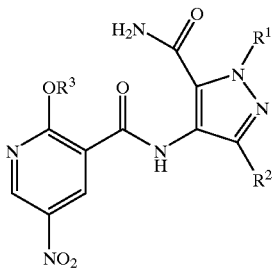

XIIA

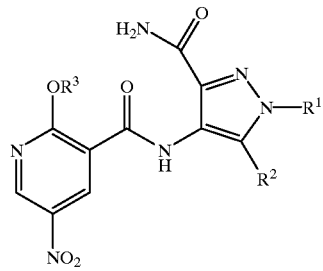

XIIB wherein $R^1$, $R^2$ and $R^3$ are as defined previously for compounds of formulae XIA and XIB, by conventional techniques, such as catalytic hydrogenation. Typically, the hydrogenation may be achieved using a Raney nickel catalyst in a suitable solvent such as ethanol at a hydrogen pressure of about 150 kPa to 500 kPa, especially 345 kPa, at from about 40° C. to about 50° C.

Compounds of formulae XIIA and XIIB may be prepared by reaction of corresponding compounds of formulae IIIA and IIIB as defined hereinbefore, with a compound of formula XIII:

XIII

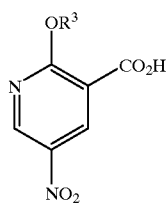

wherein R³ is as previously defined for compounds of formulae XIIA and XIIB. The reaction may be achieved using analogous amide bond forming techniques to those previously described for compounds of formulae IIIA and IIB.

Compounds of formulae XA and XB may alternatively be prepared by reduction of corresponding compounds of formulae XIIIA and XIIIB, respectively:

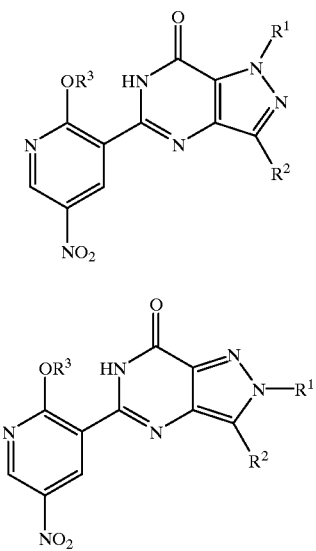

XIIIA

XIIIB wherein R¹, R² and R³ are as previously defined for compounds of formulae XA and XB. This reduction may be performed under a variety of reaction conditions, for example by catalytic hydrogenation (e.g. using 10% Pd/C in an alcohol, such as ethanol, at 60 psi (415 kpa) $H_2$ pressure and room temperature) or by transition metal catalyzed reduction (e.g. at around room temperature in the presence of iron powder (e.g. 7 eq.) in acetic acid, or $TiCl_3$ (e.g. 9 eq.) in acetic acid).

Compounds of formulae XIIIA and XIIIB may be prepared by reaction of a compound of formula XIIIC,

XIIIC

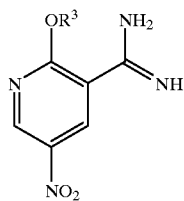

or, preferably, a carboxylic acid addition salt thereof, wherein R³ is as previously defined for compounds of formulae XIIIA and XIIIB, with either:

(a) a corresponding compound of formula IIIA or formula IIIB, as defined hereinbefore; or
(b) a corresponding compound of formula XVIIA or formula XVIIB, as defined hereinafter, in both cases under conditions such as those described herein. Such reactions may be carried out, for example, using 1.0 to 1.1 equivalents of the amidine compound of formula XIIIC, for example by refluxing in 3-methyl-3-pentanol.

Compounds of formula XIIIC may be prepared from the corresponding cyanopyridine under conditions well known to those skilled in the art.

Compounds of formulae XIIIA and XIIIB in which R² represents lower alkyl (which alkyl group is branched and unsaturated at the carbon atom that is attached to the rest of the molecule), $NR^{12}R^{13}$, cyano, aryl or $Het^1$ (which $Het^1$ group is either aromatic or is unsaturated at the carbon atom that is attached to the rest of the molecule) may alternatively be prepared from corresponding compounds of formulae XIIID or XIIIE, respectively:

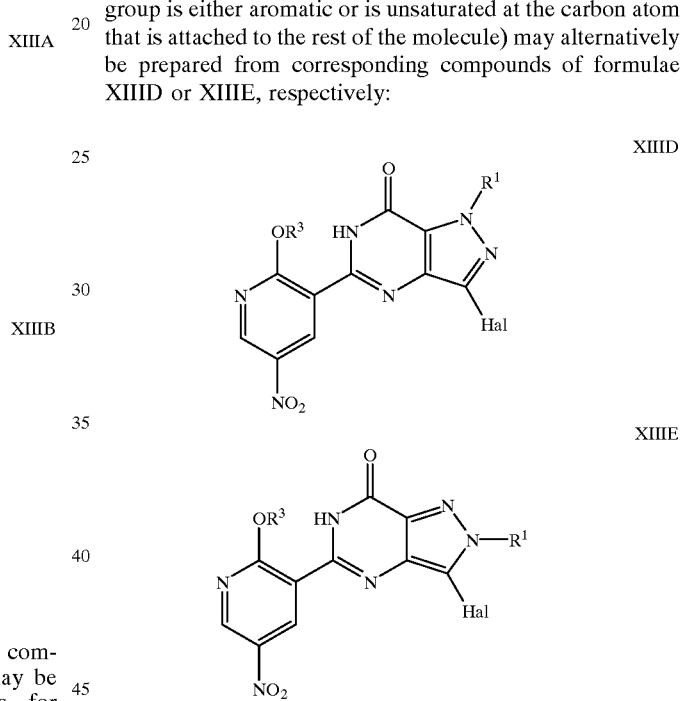

XIIID

XIIIE wherein Hal represents Cl, Br or I, preferably I and especially Br, and R¹ and R³ are as previously defined for compounds of formulae XIIIA and XIIIB, for example as described hereinafter for preparation of compounds of formulae IA and IB (see process 6 below). In addition to the process conditions described in process 6 below, suitable coupling conditions include so-called "Suzuki" conditions (e.g. 1.2 eq. of boronic acid, 2 eq. of $K_2CO_3$ and 0.1 eq. of $Pd(PPh_3)_4$, refluxing in an approximately 4:1 mixture of dioxane:water, or 2.5 to 3 eq. of CsF, 0.05 to 0.1 eq. of $Pd_2(dba)_3$ and 0.01 to 0.04 eq of P(o-tol)₃, refluxing in DME); or so-called "Stille" conditions (1.5 eq. of stannane, 10 eq. of LiCl, 0.15 eq. of CuI, and 0.1 eq. of $Pd(PPh_3)_4$, refluxing in dioxane, or 5 eq. of stannane, 3.6 eq. of $Et_3N$, $Pd_2(dba)$ and P(o-tol)₃, refluxing in MeCN).

Compounds of formula XIIID and XIIIE may be prepared by halogenation of corresponding compounds of formulae XIIIF and XIIIG, respectively:

XIIIF

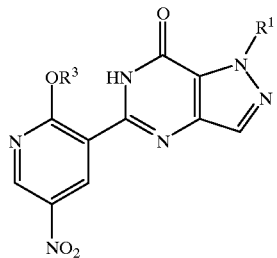

XIIIG

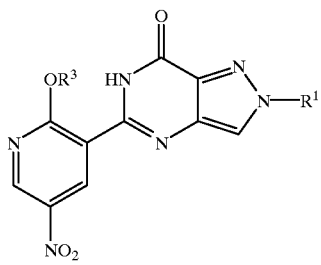

wherein R¹ and R³ are as hereinbefore defined, under conditions known to those skilled in the art (e.g., for bromination, at between room temperature and reflux in the presence of acetic acid as solvent, 1.5 to 2.0 eq. of bromine and e.g. 1.5 to 2.0 eq. of sodium acetate).

Compounds of formulae VIIIA and VIIIB, in which A is CH, may be prepared from corresponding compounds of formulae XIVA and XIVB, respectively:

XIVA

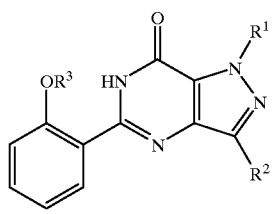

XIVB

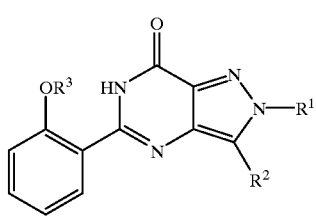

wherein R¹, R² and R³ are as previously defined for compounds of formulae VIIIA and VIIIB, for example using conventional methods for the introduction of a $SO_2Y$ group into an aromatic ring system, such as reaction of a compound of formula XIVA and XIVB with a compound of formula $SO_2Y$ and/or a compound of formula $YSO_3H$. When Y is chloro, an excess of chlorosulphonic acid, optionally with an excess of thionyl chloride, at from about 0° C. to room temperature may be used in an appropriate organic solvent (e.g. dichloromethane).

Compounds of formulae XIVA and XIVB are available using known techniques. For example, compounds of formulae XIVA and XIVB, in which R¹ represents lower alkyl, alkylHet or alkylaryl, may be prepared by alkylation of corresponding compounds of formulae XVA and XVB, respectively:

XVA

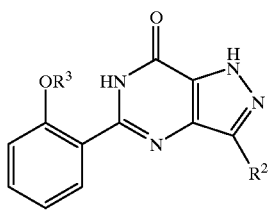

XVB

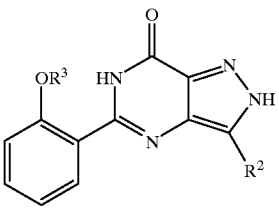

wherein R² and R³ are as previously defined for compounds of formulae XIVA and XIVB, using methods which are well known to those skilled in the art. For example, the reaction may be accomplished by reaction of a compound formula XVA or XVB with a compound of formula R¹L¹, wherein R¹ represents lower alkyl, alkylhet or alkylaryl, and L¹ is a suitable leaving group, using conventional techniques which are well known to those skilled in the art. Preferably, the leaving group is halo (preferably chloro, bromo or iodo) and the alkylation is performed in the presence of an appropriate base (e.g. sodium hydride), in an appropriate solvent (e.g. dimethylformamide), optionally in the presence of sodium iodide or potassium iodide, at from about −70° C. to about 100° C.

Preferably the alkylation is conducted at from about room temperature to about 80° C. Alternatively, compounds of formulae XVA and XVB may be reacted with a compound of formula R¹OH, wherein R¹ represents lower alkyl, alkylHet or alkylaryl, using classical Mitsunobu methodology.

Compounds of formulae XIVA and XIVB may alternatively be prepared by cyclization of corresponding compounds of formulae XVIA and XVIB, respectively:

XVIA

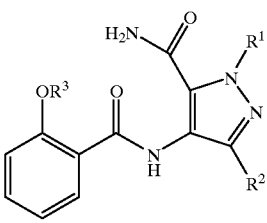

XVIB

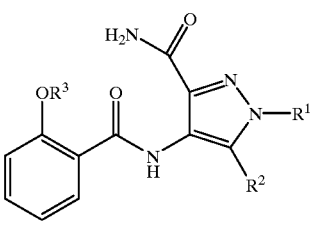

wherein R¹, R² and R³ are as previously defined for compounds of formulae XIVA and XIVB. The cyclization may be accomplished using analogous conditions to those described previously for compounds of formula IIA and IIB.

Compounds of formulae XVIA and XVIB may be prepared by coupling corresponding compounds of formulae XVIIA and XVIIB, respectively:

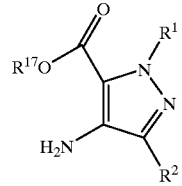

XVIIA

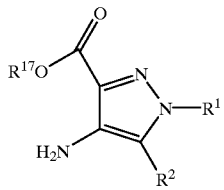

XVIIB wherein $R^1$ and $R^2$ are as previously defined for compounds of formulae XVIA and XVIB and $R^{17}$ represents a lower (e.g. $C_{1-6}$ alkyl) group, with a compound of formula XVIII or a carboxylic acid derivative thereof:

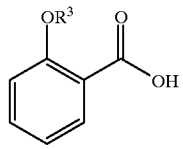

XVIII wherein $R^3$ is as previously defined for compounds of formulae XVIA and XVIB, followed by conversion of the $C(O)OR^{17}$ group of the resultant amide into $C(O)NH_2$ using conventional techniques known to those skilled in the art. In a particular embodiment, the in-situ conversion of the $C(O)OR^{17}$ group of compounds of formulae XVIIA and XVIIB into a $C(O)NH_2$ group, and the cyclization of the intermediate formed from the coupling, may be accomplished in a one-pot procedure. Preferably, this one-pot procedure is accomplished with a saturated methanolic ammonia solution, in the presence of base (e.g. potassium t-butoxide), under pressure, at elevated temperatures, especially at 100° C.

Compounds of formulae XIVA and XIVB, in which $R^2$ represents $C(O)NH_2$, may alternatively be prepared by reaction of corresponding compounds of formulae XIXA and XIXB, respectively:

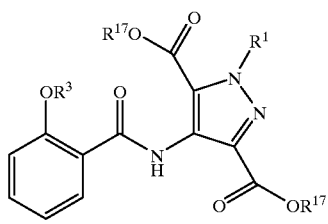

XIXA

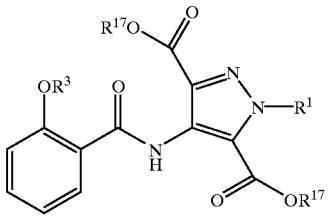

XIXB wherein $R^1$ and $R^3$ are as previously defined for compounds of formulae XIVA and XIVB and $R^{17}$ is as previously defined for compounds of formulae XVIIA and XVIIB, with ammonia, followed by cyclization of the resultant intermediate using similar techniques to those described hereinbefore.

Preferably, the reaction is accomplished in a saturated methanolic ammonia solution, in a sealed vessel, at elevated temperatures, e.g. 100° C. The cyclization of the resultant intermediate may be accomplished using analogous techniques to those previously described for preparation of compounds of formulae IA and IB from compounds of formulae IIA and IIB. In a particular embodiment, the in-situ conversion of the $C(O)OR^{17}$ group, and the cyclization, may be accomplished in a one-pot procedure.

Compounds of formula XIXA and XIXB may be prepared by reaction of corresponding compounds of formulae XXA and XXB, respectively:

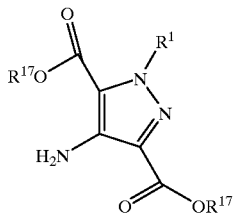

XXA

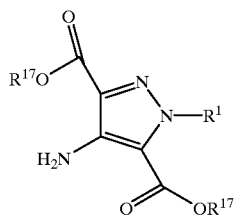

XXB wherein $R^1$ and $R^{17}$ are as previously defined for formulae XIXA and XIXB, with a compound of formula XVIII as defined hereinbefore. The coupling reaction may be performed using analogous conditions to those previously described for compounds of preparation of compounds of formulae IIA and IIB.

Compounds of formulae XIVA and XIVB, in which $R^2$ represents $C(O)NR^{12}R^{13}$, may alternatively be prepared by cyclization of corresponding compounds of formulae XXIA and XXIB, respectively:

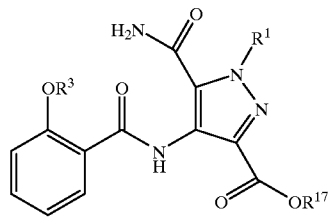

XXIA

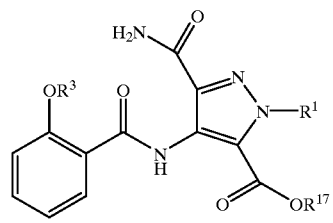

XXIB

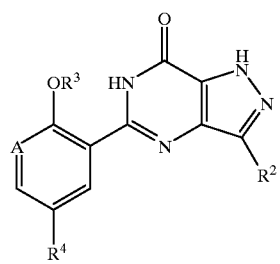

XXIIA

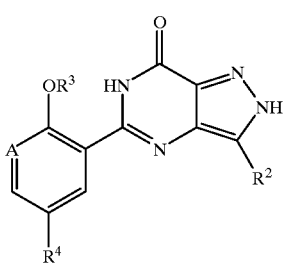

XXIIB wherein $R^1$ and $R^3$ are as previously defined for compounds of formulae XIVA and XIVB and $R^{17}$ is as previously defined for formulae XVIIA and XVIIB, followed by conversion of the $C(O)OR^{17}$ group of the resultant intermediate into an $C(O)NR^{12}R^{13}$ group, in which $R^{12}$ and $R^{13}$ are as previously defined for compounds of formulae IA and IB.

The cyclization may be accomplished using analogous cyclization techniques to those previously described for formulae IIA and IIB. The conversion of $C(O)OR^{17}$ group into $C(O)NR^{12}R^{13}$ may be accomplished using techniques which are known to those skilled in the art. Typically, the reaction is accomplished by removal of $R^{17}$ and then reacting the resultant acid (or derivative, e.g. alkali metal salt, if formed by the removal reaction) with a compound of formula $HNR^{12}R^{13}$, in which $R^{12}$ and $R^{13}$ are as previously defined for formulae IA and IB, using analogous amide coupling techniques to those described hereinbefore for compounds of formulae IIA and IIB. It will be appreciated that by an appropriate selection of the protecting group $R^{17}$, it may be removed during the reaction of the product formed from the cyclization of compounds of formulae XXIA and XXIB.

In a further embodiment, compounds of formulae XIVA and XIVB, in which $R^2$ represents $C(O)NR^{12}R^{13}$, and $R^{12}$ and $R^{13}$ are as defined hereinbefore for compounds of formulae IA and IB, except that they do not represent H, may be prepared from corresponding compounds of formula XIVA and XIVB, in which $R^2$ represents $C(O)NH_2$.

This conversion may be accomplished using procedures which are known to those skilled in the art. For example, the $CONH_2$ group may be hydrolysed into the corresponding acid (or acid salt) group, which may then be coupled to a compound of formula $HNR^{12}R^{13}$ using analogous amide bond forming techniques to those previously described for compounds of formulae IIA and IIB. Preferably, the hydrolysis is performed under basic conditions e.g. using aqueous sodium hydroxide in ethanol or dioxan, at reflux temperature of the reaction.

5. Compounds of formulae IA and IB in which $R^1$ represents lower alkyl, alkylHet or alkylaryl may be prepared by alkylation of corresponding compounds of formulae XXIIA and XXIIB, respectively:

wherein $R^2$, $R^3$, $R^4$ and A are as previously defined for compounds of formulae IA and IB, for example as described hereinbefore for preparation of compounds of formulae XIVA and XIVB. The skilled person will appreciate that compounds of formulae XXIIA and XXIIB are, respectively, compounds of formulae IA and IB in which $R^1$ represents H.

6. Compounds of formulae IA and IB, in which $R^2$ represents lower alkyl (which alkyl group is branched and unsaturated at the carbon atom that is attached to the rest of the molecule), $NR^{12}R^{13}$, cyano, aryl or $Het^1$ (which $Het^1$ group is either aromatic or unsaturated at the carbon atom that is attached to the rest of the molecule), may be prepared by cross-coupling of corresponding compounds of formula XXIIIA and XXIIIB:

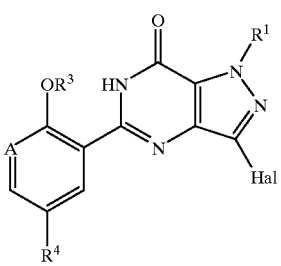

XXIIIA

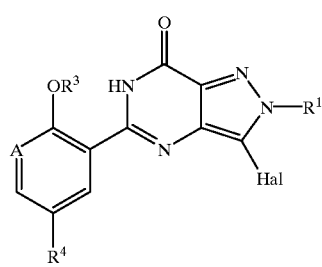

XXIIIB wherein Hal, $R^1$, $R^3$, $R^4$ and A are as hereinbefore defined, using a compound of formula $R^{2a}M$ wherein $R^{2a}$ represents lower alkyl (which alkyl group is branched and unsaturated at the carbon atom that is attached to M), NR$^{12}$R$^{13}$, cyano, aryl or Het$^1$ (which Het$^1$ group is either aromatic or unsaturated at the carbon atom that is attached to M), R$^{12}$ and R$^{13}$ are as hereinbefore defined and M represents an optionally substituted metal or boron group, which group is suitable for cross-coupling reactions, for example a trialkylstannae (e.g. tri-n-butylstannane), a dialkylborane (e.g. diethylborane), a dialkoxy borane, a dihydroxyborane, lithium, a halomagnesium, a halozinc, copper, a halomercury, in the presence of an appropriate catalyst system (e.g. a palladium or nickel catalyst).

The cross-coupling reaction is preferably carried out in the presence of a base (e.g. potassium carbonate, cesium fluoride or triethylamine), preferably in excess. Those skilled in the art will appreciate that the type of catalyst that is employed will depend on factors such as the nature of the M group, the substrate that is employed etc.

Typical procedures that may be employed include those described hereinafter. In a further typical procedure, a compound of formula R$^2$M may be used, in which M is halozinc. Such a compound may be prepared by reaction of a compound R$^2$Hal, where Hal and R$^2$ are as hereinbefore defined, with an alkyllithium (e.g. n-butyllithium) at a temperature of between –78° C. and room temperature, in a suitable solvent (e.g. THF), and the resultant solution is then treated with Zn(II)Cl$_2$ (solution in ether) and the resultant solution is treated with a compound of formula XXIIIA or XXIIIB in the presence of a palladium catalyst (e.g. tetrakis(triphenyl) phosphine palladium) in a suitable solvent (e.g. THF). The reaction may be carried out at from room temperature to reflux temperature.

Suitable coupling conditions also include so-called Suzuki and Stille conditions such as those described hereinbefore in respect of preparation of compounds of formulae XIIIA and XIIIB.

The skilled person will appreciate that compounds of formulae IA and IB in which R$^2$ represents lower alkyl that is branched, but not unsaturated, at the carbon atom that is attached to the rest of the molecule may be prepared by in this way, provided that the corresponding compound of formula IA or IB in which the corresponding R$^2$ group is unsaturated is subsequently hydrogenated under conditions known to those skilled in the art.

Compounds of formulae XXIIA and XXIIB may be prepared by cyclization of corresponding compounds of formulae XXIVA and XXIVB, respectively:

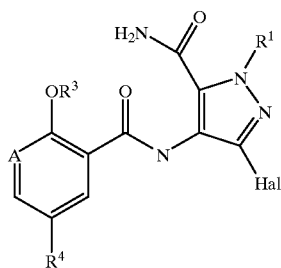

XXIVA

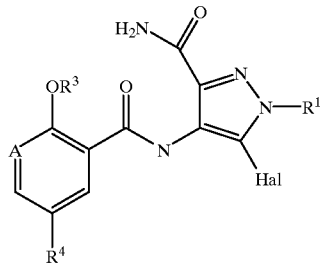

XXIVB in which R$^1$, R$^3$, R$^4$, A and Hal are as hereinbefore defined, for example under analogous reaction conditions to those described hereinbefore for compounds of formulae IIA and IIB.

Compounds of formulae XXIVA and XXIVB may be prepared analogously to methods described herein, for example coupling of a compound of formula IV, as hereinbefore defined, to an appropriate 4-amino-3-halopyrazole-5-carboxamide, which pyrazole compound may, in turn, be prepared by halogenation of a corresponding 4-aminopyrazole-5-carboxamide, under conditions which are well known to those skilled in the art.

Compounds of formulae XXIIA and XXIIB may alternatively be prepared from corresponding compounds of formulae XXVA and XXVB, respectively:

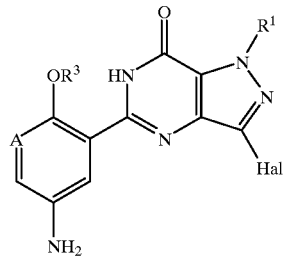

XXVA

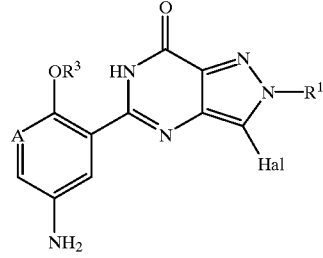

XXVB wherein A, Hal, R$^1$ and R$^3$ are as hereinbefore defined, for example as described hereinbefore for preparation of compounds of formulae IA and IB from compounds of formulae XA and XB (see process 4 above).

Compounds of formulae XXVA and XXVB may be prepared via routine techniques (for example for compounds of formulae XXVA and XXVB in which A represents N, reduction of corresponding nitropyridine compounds of formulae XIIID and XIIIE as defined herein, respectively, for example as described herein).

7. Compounds of formulae IA and IB in which R$^2$ represents N(H)C(O)R$^{12}$ may be prepared by acylation of a corresponding compound of formula IA or IB in which R$^2$ represents NH$_2$, using a compound of formula XXVI,

L$^1$C(O)R$^{12}$    XXVI in which $L^1$ and $R^{12}$ are as hereinbefore defined under conditions that are known to those skilled in the art.

8. Compounds of formulae IA and IB in which $R^2$ represents $NR^{12}R^{13}$ in which one of $R^{12}$ and $R^{13}$ does not represent H may be prepared by alkylation of a corresponding compound of formula IA or IB in which $R^2$ represents $NH_2$ using an appropriate alkylating agent under conditions that are known to those skilled in the art.

9. Compounds of formulae IA and IB in which $R^2$ represents $NR^{12}R^{13}$ in which one of $R^{12}$ and $R^{13}$ does not represent H may be prepared by reductive amination from a compound of formula IA or IB in which $R^2$ represents $NH_2$, using an appropriate carbonyl compound under conditions that are known to those skilled in the art.

10. Compounds of formulae IA and IB in which $R^2$ represents $NH_2$ may be prepared by reduction of corresponding compounds of formulae XXVIIA or XXVIIB, respectively:

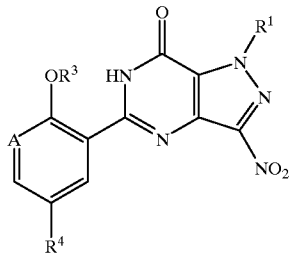

XXVIIA

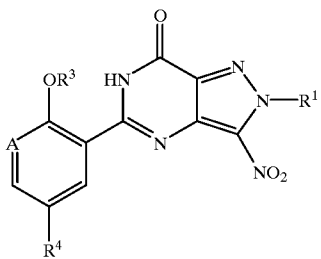

XXVIIB wherein A, $R^1$, $R^3$ and $R^4$ are as hereinbefore defined under conditions is that are well known to those skilled in the art.

Compounds of formulae XXVIIA and XXVIIB may be prepared by nitration of corresponding compounds of formulae XXVIIIA or XXVIIIB, respectively:

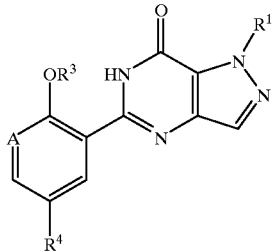

XXVIIIA

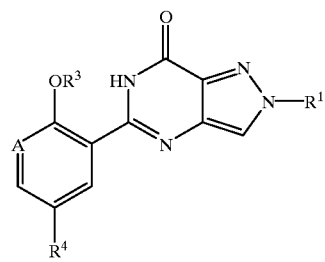

XXVIIIB wherein A, $R^1$, $R^3$ and $R^4$ are as hereinbefore defined, using conventional techniques. For example, nitration may be performed at or around room temperature using 1.5 to 3 eq. of ammonium nitrate in the presence of trifluoroacetic anhydride.

Compounds of formulae XXVIIIA and XXVIIIB may be prepared analogously to methods described herein in respect of the preparation of compounds of formulae IA and IB.

Compounds of formulae IIA and IIIB, IV, VIIA and VIIB, IX, XIII, XIIIF and XIIIG, XVA and XVB, XVIIA and XVIIB, XVIII, XXA and XXB, XXIA and XXIB and XXVI, and compounds of formulae $HNR^{12}R^{13}$, $R^{2a}M$, $R^1L^1$ and $R^1OH$, and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions.

Substituents on aryl and Het/Het$^1$ groups in the above-mentioned compounds may be introduced, removed and interconverted, using techniques which are well known to those skilled in the art. For example, compounds of formulae IA and IB as described hereinbefore, in which $R^1$ represents an aryl or alkylaryl group, may be prepared by dehalogenating corresponding compounds of formula IA or IB, in which $R^1$ represents an aryl or alkylaryl substituted with a halo group, such as a bromo or iodo. The reaction may be performed using methods which are well known to those skilled in the art, for example using a suitable palladium catalyst, such as palladium (0) tetrakis(triphenyl)phosphine, a suitable hydrogen donor (e.g. sodium formate), and a suitable base (e.g. triethylamine), in a suitable solvent (e.g. acetonitrile and/or dimethylsulphoxide).

The skilled person will also appreciate that various standard substituent or functional group interconversions and transformations within certain compounds of formulae IA and IB will provide other compounds of formulae IA and IB. For example, alkoxide exchange at the 2-position of the 5-phenyl and the pyridin-3-yl substituents. Moreover, certain compounds of formulae IA and IB, for example those in which $R^{14}$ and $R^{15}$, together with the nitrogen to which they are attached, form a 4-$R^{16}$-piperazinyl group, in which $R^{16}$ does not represent H, may be prepared directly from the corresponding piperazine analogues in which $R^{16}$ represents H, using standard procedures (e.g. alkylation).

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protecting groups for amino include tert-butyloxycarbonyl, 9-fluorenylmethoxycarbonyl or benzyloxycarbonyl. Suitable protecting groups for carboxylic acid include $C_{1-6}$alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae IA and IB which contain a basic centre may be prepared in a conventional manner. For example, a solution of the free base may be treated with the appropriate acid, either neat or in a suitable solvent, and the resulting salt may then be isolated either by filtration or by evaporation under vacuum of the reaction solvent. Pharmaceutically acceptable base addition salts can be obtained in an analogous manner by treating a solution of a compound of formula IA or IB with the appropriate base. Both types of salt may be formed or interconverted using ion-exchange resin techniques.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

All protected derivatives, and prodrugs, of compounds of formula I are included within the scope of the invention.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative) or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is furter provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative or prophylactic treatment of male erectile dysfunction (MED), female sexual dysfunction (FSD), premature labor, dysmenorrhoea, benign prostatic hyperplasia (BPH), bladder outlet obstruction, incontinence, stable and unstable variant (Prinzmetal) angina, hypertension, pulmonary hypertension, congestive heart failure, atherosclerosis, stroke, peripheral vascular disease, conditions of reduced blood vessel patency (e.g. post transluminal coronary angioplasty (post-PTCA)), chronic asthma, bronchitis, allergic asthma, allergic rhinitis, glaucoma and diseases characterised by disorders of gut motility (e.g. irritable bowel syndrome (IBS)). Other conditions which may be mentioned include pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer metastasis, baldness, nutcracker oesophagus, anal fissure and hypoxic vasoconstriction. Particularly preferred conditions include MED and FSD.

Thus the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 10 to 500 mg/kg (in single or divided doses).

Thus, for example, the tablets or capsules of the compound of the invention may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluorometane, dichlorotetrafluoro-ethane, a hydrofluoroalkane such as 1,1, 1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg, which may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The skilled person will also appreciate that, in the treatment of certain conditions (including MED and FSD), compounds of the invention may be taken as a single dose on an "as required" basis (i.e. as needed or desired).

Generally, in humans, oral administration of the compounds of the invention is the preferred route, being the most convenient and, for example in MED, in avoiding the well-known disadvantages associated with intracavernosal (i.c.) administration A preferred oral dosing regimen in MED for a typical man is from 25 to 250 mg of compound when required.

In circumstances where the recipient suffers from a swallowing disorder or from impairment of drug absorption after oral administration, the drug may be administered parenterally, e.g. sublingually or bucally.

For veterinary use, a compound of the invention is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test methods.
Biological Tests
Phosphodiesterase (PDE) Inhibitory Activity In vitro PDE inhibitory activities against cyclic guanosine 3', 5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal is muscle; and the photoreceptor PDE (PDE6) from bovine retina.

Assays were performed using a modification of the "batch" method of W. J. Thompson et al. (Biochem., 1979, 18, 5228). Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of precontracted rabbit corpus cavernosum tissue strips, as described by S. A. Ballard et al. (Brit. J. Pharmacol., 1996, 118 (suppl.), abstract 153P).

In Vivo Activity

Compounds may be screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

Compounds of the invention may be tested at varying i.v and p.o. doses in animals such as mouse and dog, observing for any untoward effects.

Examples and Preparations

The synthesis of the compounds of the invention and of the intermediates for use therein are illustrated by the following Examples and Preparations.

$^1$H nuclear magnetic resonance (NMR) spectra were recorded using either a Varian Unity 300 or a Varian Inova 400 spectrometer and were in all cases consistent with the proposed structures. Characteristic chemical shifts (δ) are given in parts-per-million downfield from tetramethylsilane using conventional abbreviations for designation of major peaks: eg s, singlet; d, doublet; t, triplet; q, quartet; m, multiplet; br, broad.

Mass spectra (mlz) were recorded using a Fisons Instruments Trio mass spectrometer in the thermospray ionisation mode.

Room temperature includes 20 to 25° C.

Synthesis of Intermediates

Preparation 1

4-Nitro-1H-pyrazole-3,5-dicarboxylic acid

Fuming sulphuric acid (105 ml) was added dropwise over 45 minutes to ice-cooled finning nitric acid (88 ml), so as to maintain the internal temperature below 20° C. Once addition was complete the mixture was warmed to 40° C., pyrazole-3,5-dicarboxylic acid (125 g, 0.80 mol) added portionwise over 75 minutes, so as to maintain the reaction temperature below 50° C., and the reaction then stirred at 60° C. for 18 hours. The cooled mixture was poured onto ice (1 kg), and flaked potassium hydroxide carefully added with stirring, until the solution pH was 2. The resulting precipitate was filtered, and triturated with boiling water (500 ml), to afford the title compound (123 g, 76%) as a white solid. m.p. 325–327° C.

Preparation 2 4-Nitro-1H-pyrazole-3,5-dicarboxylic acid dimethyl ester

Thionyl chloride (290 ml, 3.98 mol) was added dropwise over 2 hours, to an ice cooled suspension of the title compound of Preparation 1 (123 mmol , 0.61 mol) in dry methanol (1200 ml), and the reaction stirred under reflux for 48 hours. The cooled mixture was concentrated under reduced pressure, partitioned between water (500 ml) and dichloromethane (500 ml), and filtered. The phases were separated, the aqueous layer extracted with dichloromethane (4×250 ml), the combined organic solutions dried ($Na_2SO_4$), and evaporated under reduced pressure to afford the title compound (74.6 g, 53%) as a white solid.

Found: C, 36.39; H, 2.98; N, 18.15. $C_7H_7N_3O_6$ requires C, 36.69; H, 3.08; N, 18.34%.

δ($CDCl_3$): 4.00 (6H, s).

LRMS: m/z 247 (M+18)+

Preparation 3 4-Nitro-1-(pyridin-2-yl)methyl-1H-pyrazole-3,5-dicarboxylic acid dimethyl ester Cesium carbonate (14.22 g, 43.6 mmol) was added to a solution of the title compound of Preparation 2 (10.0 g, 43.6 mmol) in dinethylformamide (100 ml), and the mixture stirred at room temperature for 30 minutes. 2-(Chloromethyl)pyridine hydrochloride (7.16 g, 43.6 mmol) was added and the reaction stirred at room temperature for a farther 22 hours. The reaction mixture was concentrated under reduced pressure, the residue partitioned between dichloromethane (150 ml) and water (70 ml), and the layers separated. The aqueous phase was extracted with dichloromethane (2×100 ml), the combined organic extracts dried ($MgSO_4$), and evaporated under reduced pressure. The residual brown solid was purified by column chromatography on silica gel, using an elution gradient of ethyl acetate-:pentane (20:80 to 50:50) to afford the title compound, (6.34 g, 45%) as a white solid.

δ($CDCl_3$): 3.88 (3H, s), 3.96 (3H, s), 5.93 (2H, s), 7.15 (1H, d), 7.21 (1H, m), 7.66 (1H, m), 8.52 (1H, d).

LRMS: m/z 321 (M+1)$^+$

Preparation 4

4-Nitro-1-(pyridin-3-yl)methyl-1H-pyrazole-3,5-dicarboxylic acid dimethyl ester

A mixture of the title compound of Preparation 2 (4.0 g, 17 mmol), and cesium carbonate (2.86 g, 19 mmol) in dimethylformamide (100 ml) was stirred at room temperature for 45 minutes, 3-chloromethyl)pyridine hydrochloride (6.26 g, 19 mmol) added and stirring continued for a further 18 hours. The reaction mixture was concentrated under reduced pressure, and the residue partitioned between ethyl acetate (50 ml) and water (5 ml). The phases were separated, the aqueous layer extracted with ethyl acetate (2×50 ml) and the combined organic extracts dried ($Na_2SO_4$) and evaporated under reduced pressure. The residual brown oil was purified by column chromatography on silica gel, using an elution gradient of dichloromethane:methanol (100:0 to 98:2) to afford the title compound (2.40 g, 45%) as a white solid.

δ($CDCl_3$): 3.92 (3H, s), 3.97 (3H, s), 5.82 (2H, s), 7.29 (1H, m), 7.70 (1H, d), 8.60 (1H, d), 8.69 (1H, s).

LRMS: m/z 321 (M+1)$^+$

Preparation 5

4-Nitro-1-(pyridin4-yl)methyl-1H-pyrazole-3,5-dicarboxylic acid dimethyl ester

Obtained as a white solid (64%) from the title compound of Preparation 2 and 4-(chloromethyl)pyridine hydrochloride using the procedure of Preparation 4.

δ($CDCl_3$): 3.90 (3H, s), 3.98 (3H, s), 5.80 (2H, s), 7.18 (2H, d), 8.62 (2H, d).

Preparation 6

1-Benzyl-4-nitro-1H-pyrazole-3,5-dicarboxylic acid dimethyl ester

A mixture of the title compound of Preparation 2 (3.10 g, 13.5 mmol), cesium carbonate (2.20 g, 6.75 mmol) and benzyl bromide (1.6 ml, 13.5 mmol) in dimethylformamide (40 ml) was stirred at room temperature for 72 hours. The reaction mixture was concentrated under reduced pressure and the residue partitioned between water (50 ml) and ethyl acetate (50 ml). The phases were separated, the aqueous layer extracted with ethyl acetate (2×50 ml) and the combined organic extracts dried ($Na_2SO_4$) and evaporated under reduced pressure to afford the title compound (4.35 g, 99%) as a colourless oil.

δ(CDCl$_3$): 3.87 (3H, s), 3.96 (3H, s), 5.78 (2H, s), 7.34 (5H, s).

Preparation 7
1-(4-Bromobenzyl)-4-nitro-1H-pyrazole-3,5-dicarboxylic acid dimethyl ester A mixture of the title compound of Preparation 2 (5.04 g, 22.0 mmol), cesium carbonate (7.88 g, 24.0 mmol), and 4-bromobenzyl bromide (5.75 g, 24.0 mmol) in dimethylformamide (100 ml) was stirred for 18 hours at room temperature. The reaction mixture was concentrated under reduced pressure, the residue partitioned between water (50 ml) and ethyl acetate (75 ml) and the phases separated. The aqueous phase was extracted with dichloromethane (3×50 ml), and the combined organic extracts dried (Na$_2$SO$_4$) and evaporated under reduced pressure. The residual yellow solid was triturated with ethanol to afford the title compound, (6.60 g, 75%).

δ(CDCl$_3$): 3.90 (3H, s), 3.97 (3H, s), 5.74 (2H, s), 7.24 (2H, d), 7.48 (2H, d).

LRMS: m/z 415 (M+18)$^+$

Preparation 8
1-Methyl-4-nitro-1H-pyrazole-3,5-dicarboxylic acid dimethyl ester

Obtained as an off-white solid after trituration with hexane (93%), from dimethyl sulphate and the title compound of Preparation 2, using the procedure of Preparation 7.

δ(CDCl$_3$): 3.95 (6H, 2xs), 4.26 (3H, s).

LRMS: m/z 261 (M+18)$^+$

Preparation 9
1-Cyclobutylmethyl-4-nitro-1H-pyrazole-3,5-dicarboxylic acid dimethyl ester Diethylazodicarboxylate (3.78 ml, 24.0 mmol) was added dropwise to an ice-cooled solution of cyclobutanemethanol (2.06 ml, 21.8 mmol), the title compound of Preparation 2 (5.0 g, 21.8 mmol) and triphenylphosphine (6.30 g, 24.0 mmol) in tetrahydrofuran (50 ml) and the reaction stirred for a furter 2 hours at 0° C. The reaction mixture was concentrated under reduced pressure and the residue purified by column chromatography on silica gel, using an elution gradient of ethyl acetate:hexane (15:85 to 20:80) to afford the title compound (6.23 g, 96%) as a colourless oil.

δ(CDCl$_3$): 1.80–1.95 (4H, m), 2.05 (2H, m), 2.90 (1H, m), 3.96 (6H, 2xs), 4.63 (2H, d).

LRMS: m/z 315 (M+18)$^+$

Preparation 10
1-[2-(4-Morpholinyl)ethyl]-4-nitro-1H-pyrazole-3,5-dicarboxylic acid dimethyl ester Obtained as a solid (15%) from 4-(2-chloroethyl) morpholine hydrochloride and the title compound of Preparation 2, using the procedure of Preparation 3.

δ(CDCl$_3$): 2.46 (4H, m), 2.78 (2H, t), 3.61 (4H, m), 3.95 (6H, 2xs), 4.73 (2H, t).

LRMS: m/z343 (M+1)$^+$

Preparation 11
4-Amino-1-(pyridin-2-yl)methyl-1H-pyrazole-3,5-dicarboxylic acid dimethyl ester A mixture of the title compound of Preparation 3 (1.0 g, 3.12 mmol) and Raney nickel (800 mg) in methanol (50 ml) was hydrogenated at 50° C. and 345 kPa (50 psi) for 18 hours, then cooled and filtered. The filtrate was combined with a methanol wash of the filter pad, and concentrated under reduced pressure. The residue was azeotroped with dichloromethane and dried under vacuum to afford the title compound, (895 mg, 99%).

δ(DMSOd$_6$): 3.74 (3H, s), 3.80 (3H, s), 5.62 (2H, s), 5.74 (2H, s), 6.98 (1H, d), 7.26 (1H, m), 7.74 (1H, m), 8.45 (1H, d).

LRMS: m/z291 (M+1)$^+$

Preparation 12
4-Amino-1-(pyridin-3-yl)methyl-1H-pyrazole-3,5-dicarboxylic acid dimethyl ester Tin (II) chloride dihydrate (9.30 g, 41.2 mmol) was added to a suspension of the title compound of Preparation 4 (2.40 g, 7.50 mmol) in ethanol (20 ml) and the reaction stirred at 70° C. for 18 hours. The cooled reaction mixture was concentrated under reduced pressure and the residue stirred vigorously in a mixture of ethyl acetate (30 ml) and dilute sodium carbonate solution (30 ml) for an hour. The phases were separated, the aqueous layer extracted with ethyl acetate (2×25 ml), the combined organic solutions dried (Na$_2$SO$_4$) and evaporated under reduced pressure, to afford the title compound (1.77 g, 80%) as a white solid.

δ(CDCl$_3$): 3.86 (3H, s), 3.96 (3H, s), 5.37 (2H, s), 5.70 (2H, s), 7.22 (1H, m), 7.54 (1H, d), 8.52 (1H, d), 8.56 (1H, s).

Preparation 13
4-Amino-1-(pyridin-4-yl)methyl-1H-pyrazole-3,5-dicarboxylic acid dimethyl ester Obtained (96%) from the title compound of Preparation 5, using the procedure of Preparation 11.

δ(CDCl$_3$): 3.84 (3H, s), 3.96 (3H, s), 5.39 (2H, s), 5.70 (2H, s), 7.04 (2H, m), 8.55 (2H, m).

Preparation 14
4-Amino-1-(4-bromobenzyl)-1H-pyrazole-3,5-dicarboxylic acid dimethyl ester Obtained as a white solid after recrystallization from isopropyl acetate (74%), from the title compound of Preparation 7, using the procedure of Preparation 12.

δ(CDCl$_3$): 3.86 (3H, s), 3.97 (3H, s), 5.36 (2H, s), 5.64 (2H, s), 7.10 (2H, d), 7.42 (2H, d).

LRMS: m/z 369 (M+1)$^+$

Preparation 15
4-Amino-1-cyclobutylmethyl-1H-pyrazole-3,5-dicarboxylic acid dimethyl ester A mixture of the title compound of Preparation 9 (6.23 g, 21.0 mmol) and 10% palladium on charcoal (800 mg) in methanol (150 ml) was hydrogenated at 345 kPa (50 psi) and 50° C. for 18 hours. The cooled mixture was filtered, the filter pad washed with methanol (150 ml) and the filtrate evaporated under reduced pressure to afford the title compound (5.50 g, 98%) as a white solid.

δ(CDCl$_3$): 1.78–1.92 (4H, m), 1.99 (2H, m), 2.83 (1H, m), 3.94 (6H, 2x,s), 4.55 (2H, d), 5.35 (2H, s).

LRMS: m/z 268 (M+1)$^+$

Preparation 16
4-Amino-1-[2-(4-morpholinyl)ethyl]-1H-pyrazole-3,5-dicarboxylic acid dimethyl ester Obtained as a brown solid (95%) from the title compound of Preparation 10, using the procedure of Preparation 11.

δ(DMSOd$_6$): 2.40 (4H, m), 2.62 (2H, t), 3.50 (4H, m), 3.79 (3H, s), 3.81 (3H, s), 4.50 (2H, t), 5.58 (2H, s).

Preparation 17
4-Amino-1H-pyrazole-3,5-dicarboxylic acid dimethyl ester

Obtained as a white solid (91%) from the title compound of Preparation 2, using the procedure of Preparation 11.

δ(DMSOd$_6$): 3.80 (6H, s), 5.41 (2H, s), 13.83 (1H, s).

LRMS: m/z 217 (M+1)$^+$

Preparation 18
Dimethyl 4-(2-n-propoxybenzamido)-1-(pyridin-2-yl) methyl-1H-pyrazole-3,5-dicarboxylate A solution of the title compound of Preparation 11 (1.56 g, 7.84 mmol) in dichloromethane (5 ml) was added slowly to a solution of 2-n-propoxybenzoyl chloride (1.56 g, 7.84 mmol) in pyridine (10 ml) and the reaction stirred at room temperature for 18 hours. The reaction mixture was concentrated under reduced pressure, azeotroped with toluene and the residual brown oil partitioned between dichloromethane (10 ml) and saturated sodium bicarbonate solution (15 ml). The phases were separated, the aqueous layer extracted with dichloromethane (3×10 ml), and the combined organic extracts washed with aqueous copper (II) sulphate solution (2×10 ml), dried ($Na_2SO_4$) and evaporated under reduced pressure. The residue was purified by column chromatography on silica gel, using an elution gradient of dichloromethane:methanol (100:0 to 98:2) to afford the title compound (1.80 g, 51%) as a yellow foam.

δ($CDCl_3$): 1.06 (3H, t), 2.03 (2H, m), 3.78 (3H, s), 3.95 (3H, s), 4.25 (2H, t), 5.85 (2H, s), 6.95–7.08 (3H, m), 7.18 (1H, m), 7.48 (1H, m), 7.62 (1H, m), 8.24 (1H, d), 8.54 (1H, d), 10.69 (1H, s).

LRMS: m/z 453 $(M+1)^+$

Preparations 19 to 23

The compounds of the following tabulated Preparations of the general formula:

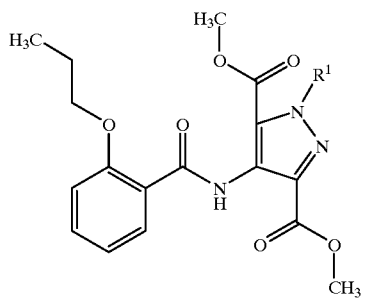

were prepared by the reaction of 2-n-propoxybenzoyl chloride and the corresponding aminopyrazoles, using similar methods to that described in Preparation 18.

Preparation 24
Dimethyl 4-(2-n-propoxybenzamido)-1H-pyrazole-3,5-dicarboxylate

A solution of 2-n-propoxybenzoyl chloride (3.99 g, 20.0 mmol) in dichloromethane (10 ml) was added dropwise to a solution of the title compound of Preparation 17 (4.0 g, 20 mmol) in pyridine (50 ml) and the reaction stirred at room temperature for 18 hours. The reaction mixture was concentrated under reduced pressure, the residue partitioned between water (30 ml) and ethyl acetate (100 ml) and the layers separated. The organic layer was washed with water (30 ml), 1N hydrochloric acid (4×50 ml), dried ($MgSO_4$) and evaporated under reduced pressure. The residue was purified by column chromatography on silica gel, using an elution gradient of ethyl acetate:pentane (50:50 to 100:0) to afford the title compound, (2.04 g, 28%) as a white solid.

δ($DMSOd_6$): 0.98 (3H, t), 1.89 (2H, m), 3.78 (3H, s), 3.81 (3H, s), 4.24 (2H, t), 7.10 (1H, m), 7.25 (1H, d), 7.57 (1H, m), 7.99 (1H, d), 10.28 (1H, s), 14.51 (1H, s). LRMS: m/z 362 $(M+1)^+$

Preparation 25
4-(2-n-Propoxybenzamido)-1H-pyrazole-3,5-dicarboxamide

Liquid ammonia (15 ml) was added carefully to a cooled (−75° C.) solution of the title compound of Preparation 24 (2.01 g, 5.56 mmol) in methanol (25 ml) and the reaction heated at 100° C. in a sealed vessel for 18 hours. The cooled reaction mixture was concentrated under reduced pressure and azeotroped with dichloromethane to afford the title compound (1.62 g, 93%) as a white solid.

δ($DMSOd_6$): 0.98 (3H, t), 1.90 (2H, m), 4.19 (2H, t), 7.08 (1H, m), 7.22 (1H, d), 7.55 (5H, m), 7.97 (1H, d), 10.56 (1H, s).

LRMS: m/z 332 $(M+1)^+$

Preparation 26
3-Carboxamido-5-(2-n-propoxyphenyl)-1-(pyridin-2-yl)methyl-1,6-dihydro-7H-pyrazolo[4,3-d]pyrimidin-7-one

| Prep. No. | $R^1$ | Data |
|---|---|---|
| 19 | *-CH2-(pyridin-3-yl) | δ ($CDCl_3$) : 1.06 (3H, t), 2.01 (2H, m), 3.80 (3H, s), 3.96 (3H, s), 4.25 (2H, t), 5.72 (2H, s), 7.06 (2H, m), 7.26 (1H, m), 7.48 (1H, m), 7.64 (1H, d), 8.22 (1H, d), 8.55 (1H, d), 8.60 (1H, s), 10.56 (1H, s). LRMS : m/z 453 $(M + 1)^+$ |
| 20 | *-CH2-(pyridin-4-yl) | δ ($CDCl_3$) : 1.08 (3H, t), 2.02 (2H, m), 3.78 (3H, s), 3.97 (3H, s), 4.26 (2H, t), 5.72 (2H, s), 7.08 (4H, m), 7.50 (1H, m), 8.23 (1H, d), 8.56 (2H, m), 10.70 (1H, s). |
| 21 | *-CH2-(4-bromophenyl) | δ ($CDCl_3$) : 1.08 (3H, t), 2.02 (2H, m), 3.78 (3H, s), 3.95 (3H, s), 4.25 (2H, t), 5.63 (2H, s), 7.06 (2H, m), 7.16 (2H, d), 7.45 (3H, m), 8.22 (1H, d), 10.66 (1H, s). LRMS : m/z 532 $(M + 2)^+$ |
| 22 | *-CH2-cyclobutyl | δ ($CDCl_3$) : 1.08 (3H, t), 1.86 (4H, m), 2.04 (4H, m), 2.88 (1H, m), 3.90 (3H, s), 3.95 (3H, s), 4.28 (2H, t), 4.52 (2H, d), 7.06 (2H, m), 7.48 (1H, m), 8.24 (1H, d), 10.68 (1H, s). LRMS: m/z 430 $(M + 1)^+$ |
| 23 | *-CH2CH2-morpholin-4-yl | δ ($CDCl_3$) : 1.08 (3H, t), 2.03 (2H, m), 2.48 (4H, m), 2.80 (2H, t), 3.65 (4H, m), 3.88 (3H, s), 3.95 (3H, s), 4.28 (2H, t), 4.62 (2H, t), 7.08 (2H, m), 7.48 (1H, m), 8.24 (1H, d), 10.53 (1H, s). |

An ice-cooled solution of the title compound of Preparation 18 (3.50 g, 7.74 mmol) in methanol (300 ml) was saturated with ammonia, then heated to 100° C. in a sealed vessel for 72 hours. The cooled mixture was concentrated under reduced pressure, and the residue triturated with diethyl ether, then a solution of dichloromethane:methanol (90:10), to give the title compound (1.0 g) as a white solid. The filtrate was concentrated under reduced pressure and the residue purified by column chromatography on silica gel, using dichloromethane:methanol (98:2) as eluant to afford a further 780 mg, of the title compound.

δ(CDCl$_3$): 1.18 (3H, t), 2.00 (2H, m), 4.21 (2H, t), 6.06 (3H, m), 7.06–7.20 (4H, m), 7.54 (1H, m), 7.62 (1H, m), 8.16 (1H, m), 8.43 (1H, d), 8.56 (1H, d).

LRMS: m/z 405 (M+1)$^+$

Preparation 27

3-Carboxamido-5-(2-n-propoxyphenyl)-1-(pyridin-3-yl)methyl-1,6-dihydro-7H-pyrazolo[4,3-d]pyrimidin-7-one An ice-cooled solution of the title compound of Preparation 19 (2.02 g, 4.47 mmol) in methanol (80 ml) was saturated with ammonia and the reaction heated at 100° C. in a sealed vessel for 18 hours. The cooled reaction mixture was evaporated under reduced pressure to give a white solid. Potassium t-butoxide (1.40 g, 12.43 mmol) was added to a suspension of this product in isopropanol (30 ml), and the reaction heated under reflux for 8 hours, then cooled. Water (60 ml) was added, the mixture neutralised with 2N hydrochloric acid and the resulting precipitate filtered, washed with water and dried under suction to afford the title compound (1.20 g, 66%) as a white solid.

δ(CDCl$_3$): 1.20 (3H, t), 2.04 (2H, m), 4.22 (2H, t), 5.92 (2H, s), 6.05 (1H, s), 7.10 (1H, d), 7.17 (1H, m), 7.26 (1H, m), 7.54 (1H, m), 7.86 (1H, d), 8.15 (1H, s), 8.40 (1H, d), 8.56 (1H, d), 8.80 (1H, s), 11.49 (1H, s).

LRMS: m/z 405 (M+1)$^+$

Preparation 28

3-Carboxamido-5-(2-n-propoxyphenyl)-1-(pyridin-4-yl)methyl-1,6-dihydro-7H-pyrazolo[4,3-d]pyrimidin-7-one An ice-cooled solution of the title compound of Preparation 20 (1.30 g, 2.88 mmol) in methanol (100 ml) was saturated with ammonia and the reaction heated at 100° C. for 24 hours. The cooled reaction mixture was evaporated under reduced pressure and the residue suspended in isopropanol (100 ml). Potassium t-butoxide (1.7 g, 15.1 mmol) was added and the reaction heated under reflux for 5 hours, then cooled. Water (100 ml) was added, the mixture neutralised with 2N hydrochloric acid and extracted with dichloromethane (2×100 ml). The combined organic extracts were dried (Na$_2$SO$_4$), concentrated under reduced pressure and the residue purified by column chromatography on silica gel, using an elution gradient of dichloromethane:methanol (98:2 to 94:6) to afford the title compound (550 mg, 47%).

δ(CDCl$_3$): 1.19 (3H, t), 2.03 (2H, m), 4.22 (2H, t), 5.88 (2H, s), 6.05 (1H, s), 7.10 (1H, d), 7.17 (1H, m), 7.35 (2H, d), 7.54 (1H, m), 8.16 (1H, s), 8.40 (1H, d), 8.57 (2H, d), 11.50 (1H, s).

Preparation 29

1-(4-Bromobenzyl)-3-carboxamido-5-(2-n-propoxyphenyl)-1,6-dihydro-7H-pyrazolo[4,3-d]pyrimidin-7-one Obtained (88%) from the title compound of Preparation 21, using a similar procedure to that described in Preparation 28.

δ(DMSOd$_6$): 0.94 (3H, t), 1.72 (2H, m), 4.05 (2H, t), 5.78 (2H, s), 7.08 (1H, m), 7.18 (1H, d), 7.26 (2H, d), 7.52 (3H, m), 7.76 (2H, m).

Preparation 30

3-Carboxamido-1-cyclobutylmethyl-5-(2-n-propoxyphenyl)-1,6-dihydro-7H-pyrazolo[4,3-d]pyrimidin-7-one Obtained as an off-white solid (56%) from the title compound of Preparation 22, using the procedure of Preparation 27.

δ(CDCl$_3$): 1.11 (3H, t), 1.93 (4H, m), 2.04 (4H, m), 3.07 (1H, m), 4.24 (2H, t), 4.75 (2H, d), 5.93 (1H, s), 7.10 (1H, d), 7.18 (1H, m), 7.55 (1H, m), 8.17 (1H, s), 8.42 (1H, d), 11.44 (1H, s).

LRMS: m/z 382 (M+1)$^+$

Preparation 31

3-Carboxamido-1-[2-(4-morpholinyl)ethyl]-5-(2-n-propoxyphenyl)-1,6-dihydro-7H-pyrazolo[4,3]pyrimidin-7-one Obtained as an orange solid (67%) from the title compound of Preparation 23 using a similar procedure to that described in Preparation 28.

δ(DMSOd$_6$): 0.96 (3H, t), 1.73 (2H, m), 2.50 (2H, m), 2.77 (2H, m), 3.32 (2H, m), 3.61 (4H, m), 4.05 (2H, t), 4.84 (2H, t), 7.08 (1H, m), 7.18 (1H, d), 7.52 (1H, m), 7.74 (3H, m), 12.34 (1H, s).

LRMS: m/z 427 (M+1)$^+$

Preparation 32

3-Carboxamido-5-(2-n-propoxyphenyl)-2,6-dihydro-7H-pyrazolo[4,3-d]pyrimidin-7-one A mixture of the title compound of Preparation 25 (1.2 g, 3.62 mmol) and potassium t-butoxide (1.63 g, 14.49 mmol) in n-propanol (50 ml) was heated under reflux for 18 hours. The cooled reaction mixture was concentrated under reduced pressure, the residue dissolved in water (30 ml), washed with ethyl acetate (20 ml) and acidified to pH 4 with hydrochloric acid.

The resulting precipitate was filtered, washed with water and dried at 60° C. A mixture of this solid, and N,N'-carbonyldiimidazole (670 mg, 4.13 mmol) in tetrahydrofuran (50 ml) was heated under reflux for 3 hours, then cooled in an ice-bath. The mixture was saturated with ammonia gas, and stirred at room temperature for 18 hours. The resulting precipitate was filtered, washed with ethyl acetate and dried at 60° C. to afford the title compound (510 mg, 45%) as a beige solid.

δ(DMSOd$_6$): 0.96 (3H, t), 1.75 (2H, m), 4.05 (2H, t), 7.08 (1H, m), 7.19 (1H, d), 7.50 (1H, m), 7.67 (1H, s), 7.71 (1H, s), 7.79 (1H, d).

LRMS: m/z 314 (M+1)$^+$

Preparation 33

3-N-Methylcarboxamido-5-(2-n-propoxyphenyl)-1-(pyridin-2-yl)methyl-1,6-dihydro-7H-pyrazolo[4,3-d]pyrimidin-7-one A mixture of the title compound of Preparation 26 (600 mg, 1.48 mmol) and 2N aqueous sodium hydroxide solution (20 ml) in dioxan (10 ml) was heated under reflux for 18 hours. The cooled reaction mixture was neutralized with 2N hydrochloric acid, concentrated under reduced pressure and azeotroped with toluene. The residual white solid was suspended in dichloromethane (20 ml), N-methylmorpholine (360 ml, 3.26 mmol), 1-hydroxybenzotriazole hydrate (220 mg, 1.63 mmol), methylamine hydrochloride (220 mg, 3.26 mmol) and finally 1-(3-dimethylaminopropyl)-3-ethylcarbodiimide hydrochloride (312 mg, 1.63 mmol) added and the reaction stirred at room temperature for 18 hours. The reaction mixture was filtered, sodium bicarbonate solution (20 ml) added, and the phases separated. The aqueous phase was extracted with dichloromethane (4×20 ml), the combined organic extracts washed with brine (20 ml), dried and evaporated under reduced pressure. The crude product was purified by column chromatography on silica gel, using an elution gradient of dichloromethane:methanol:0.88 ammonia (100:0:0 to 98:2:1) to afford the title compound (170 mg, 30%) as a pale yellow solid.

δ(CDCl$_3$): 1.19 (3H, t), 2.01 (2H, m), 3.17 (3H, d), 4.20 (2H, t), 6.05 (2H, s), 7.08 (2H, m), 7.18 (2H, m), 7.54 (1H, m), 7.60 (1H, m), 8.12 (1H, s), 8.42 (1H, d), 8.55 (1H, d), 11.42 (1H, s).

LRMS: m/z 419 (M+1)$^+$

Preparation 34

3-N-Methylcarboxamido-5-(2-n-propoxyphenyl)-1-(pyridin-3-yl)methyl-1,6-dihydro-7H-pyrazolo[4,3-d]pyrimidin-7-one Obtained as a white solid (55%) from the title compound of Preparation 27, using the procedure of Preparation 33.

δ(CDCl$_3$): 1.20 (3H, t), 2.04 (2H, m), 3.16 (3H, d), 4.24 (2H, t), 5.90 (2H, s), 7.09 (1H, d), 7.21 (2H, m), 7.55 (1H, m), 7.85 (1H, d), 8.15 (1H, m), 8.39 (1H, d), 8.55 (1H, d), 8.79 (1H, s), 11.43 (1H, s).

Preparation 35

3-N-Methylcarboxamido-5-(2-n-propoxyphenyl)-1-(pyridin-4-yl)methyl-1,6-dihydro-7H-pyrazolo[4,3-d]pyrimidin-7-one Obtained as a white solid (37%) from the title compound of Preparation 28, using a similar procedure to that described in Preparation 33.

δ(CDCl$_3$): 1.18 (3H, t), 2.02 (2H, m), 3.17 (3H, d), 4.21 (2H, t), 5.86 (2H, s), 7.10 (1H, d), 7.20 (1H, m), 7.30 (2H, d), 7.55 (1H, m), 8.16 (1H, s), 8.39 (1H, d), 8.56 (2H, d), 11.48 (1H, s).

LRMS: m/z 419 (M+1)$^+$

Preparation 36

1-(4-Bromobenzyl)-3-N-methylcarboxamido-5-(2-n-propoxyphenyl)-1,6-dihydro-7H-pyrazolo[4,3-d]pyrimidin-7-one A mixture of the title compound of Preparation 29 (2.56 g, 5.3 mmol) and 6N aqueous sodium hydroxide solution (60 ml) in ethanol (30 ml) was heated under reflux for 18 hours. The cooled reaction mixture was acidified with hydrochloric acid, the resulting precipitate filtered, washed with water, and dried at 60° C., to give a white solid. A mixture of this product, N-methylmorpholine (1.29 ml, 11.7 mmol), 1-hydroxybenzotriazole hydrate (950 mg, 6.2 mmol), methylamine hydrochloride (357 mg, 5.3 mmol) and finally 1-(3-dimethylaminopropyl)-3-ethylcarbodiimide hydrochloride (1.28 mg, 6.7 mmol) in dichloromethane (40 ml) was stirred at room temperature for 3 hours. The reaction mixture was washed with ammonium chloride solution (10 ml), then sodium bicarbonate solution (10 ml), dried (Na$_2$SO$_4$) and concentrated under reduced pressure. The residue was purified by column chromatography on silica gel, using dichloromethane:methanol:0.88 ammonia (98:2:0.2) as eluant to afford the title compound (1.1 g, 42%).

δ(CDCl$_3$): 1.19 (3H, t), 2.04 (2H, m), 3.16 (3H, d), 4.22 (2H, t), 5.81 (2H, s), 7.09 (1H, d), 7.19 (1H, m), 7.41 (3H, m), 7.53 (1H, m), 8.15 (1H, d), 8.58 (1H, m), 11.40 (1H, s).

LRMS:m/z 498 (M+2)$^+$

Preparation 37

1-Cyclobutyl-3-N-methylcarboxamido-5-(2-n-propoxyphenyl)-1,6-dihydro 7H-pyrazolo[4,3-d]pyrimidin-7-one Obtained after recrystallization from ethyl acetate-hexane (51%), from the title compound of Preparation 30, using a similar procedure to that described in Preparation 36.

δ(CDCl$_3$): 1.17 (3H, t), 1.86 (4H, m), 1.99 (4H, m), 3.00 (1H, m), 3.12 (3H, d), 4.20 (2H, t), 4.69 (2H, d), 7.06 (1H, d), 7.17 (1H, m), 7.50 (1H, m), 8.11 (1H, d), 8.38 (1H, d), 11.35 (1H, s).

LRMS:m/z 395 (M)$^+$

Preparation 38

3-Methoxycarbonyl-4-nitro-1-(pyridin-2-yl)methyl-1H-pyrazole-5-carboxylic acid

Potassium hydroxide solution (6.87 ml, 1N, 6.87 mmol) was added to a suspension of the title compound of Preparation 3 (2.0 g, 6.25 mmol) in methanol (50 ml) and the reaction stirred at room temperature for 18 hours. The reaction mixture was concentrated under reduced pressure, the residual brown oil dissolved in water (15 ml), and washed with diethyl ether (20 ml). The aqueous solution was acidified to pH 4 with 2N hydrochloric acid, the resulting precipitate filtered, washed with water and diethyl ether, and dried at 60° C., to afford the title compound (1.37 g, 72%).

Found: C, 46.63; H, 3.11; N, 18.00. C$_{12}$H$_{10}$N$_4$O$_6$ requires C, 47.07; H, 3.29; N, 18.30%.

δ(DMSOd$_6$): 3.85 (3H, s), 5.92 (2H, s), 7.34 (2H, m), 7.81 (1H, m), 8.48 (1H, d).

Preparation 39

1-Benzyl-3-methoxycarbonyl-4-nitro-1H-pyrazole-5-carboxylic acid

A methanolic solution of potassium hydroxide (27 ml, 2N, 54 mmol) was added to a solution of the title compound of Preparation 6 (17.4 g, 54.5 mmol) in methanol (400 ml) and the reaction stirred at room temperature for 40 hours. The reaction mixture was concentrated under reduced pressure, the residue suspended in water (100 ml), and acidified to pH 4 using 2N hydrochloric acid. This mixture was evaporated under reduced pressure and recrystallised from dichloromethane-pentane to afford the title compound as a solid.

δ(DMSO$_6$): 3.80 (3H, s), 5.74 (2H, s), 7.23–7.38 (5H, m).

Preparation 40

3-Methoxycarbonyl-1-methyl-4-nitro-1H-pyrazole-5-carboxylic acid

An aqueous solution of potassium hydroxide (6.48 ml, 2N, 12.95 mmol) was added to a suspension of the title compound of Preparation 8 (3.0 g, 12.37 mmol) in methanol (60 ml) and the reaction stirred at room temperature for 18 hours. The reaction mixture was concentrated under reduced pressure, the residue partitioned between ethyl acetate (30 ml) and water (30 ml), and the phases separated. The aqueous layer was acidified to pH 4 using 2N hydrochloric acid, extracted with ethyl acetate (4×50 ml) and the combined organic solutions dried (Na$_2$SO$_4$), and evaporated under reduced pressure to afford the title compound (1.97 g, 70%) as a white solid.

δ(DMSOd$_6$): 3.83 (3H, s), 4.14 (3H, s).

LRMS: m/z 247 (M+18)$^+$

Preparation 41

3-Methoxycarbonyl-1-methyl-4-nitro-1H-pyrazole-5-carboxylic acid chloride

Oxalyl chloride (3.05 ml, 34.9 mmol) was added dropwise to an ice-cooled suspension of the title compound of Preparation 40 (4.0 g, 17.5 mmol) and dimethylformamide (1 drop) in dichloromethane (50 ml), and the reaction was stirred at room temperature for 18 hours. The reaction mixture was concentrated under reduced pressure, and the residue triturated with hexane to afford the title compound as a beige solid.

δ(DMSOd$_6$): 3.85 (3H, s), 4.15 (3H, s).

Preparation 42

1-Benzyl-3-methoxycarbonyl-4-nitro-1H-pyrazole-5-carboxamide

Oxalyl chloride (7.8 ml, 90 mmol) was added dropwise to an ice-cooled solution of the title compound of Preparation 39 (13.7 g, 44.9 mmol) and dimethylformamide (1 drop) in dichloromethane (100 ml), and the reaction stirred at room temperature for 4 hours. The reaction mixture was concentrated under reduced pressure, the residue suspended in dioxan (50 ml), and cooled in an ice-bath. 0.88 Ammonia was added dropwise until a pH of 8 had been achieved, the mixture stirred for 30 minutes, then concentrated under reduced pressure. The residue was triturated with water, filtered and dried under suction to afford the title compound (8.2 g, 60%) as a white powder.

Preparation 43
3-Methoxycarbonyl-1-methyl-4-nitro-1H-pyrazole-5-carboxamide

Oxalyl chloride (1.1 ml, 12.6 mmol) was added dropwise to an ice-cooled solution of the title compound of Preparation 40 (1.93 g, 8.42 mmol) and dimethylformamide (1 drop) in dichloromethane (30 ml), and the reaction stirred at room temperature for 18 hours. The reaction mixture was evaporated under reduced pressure, triturated with tetrahydrofuran (100 ml), filtered and the filtrate cooled in an ice-bath. Ammonia gas was 5 passed through the solution for 30 minutes, the resulting precipitate filtered, washed with water and dried at 60° C. to afford the title compound (1.39 g, 72%) as a white solid.

Found: C, 36.97; H, 3.55; N, 24.36. $C_7H_8N_4O_5$ requires C, 36.85; H, 3.53; N, 24.56%.

$\delta(DMSO_d)$: 3.88 (3H, s), 3.92 (3H, s), 8.37 (1H, s), 8.50 (1H, s).

LRMS: m/z 246 (M+18)$^+$

Preparation 44
5-Methoxycarbonyl-1-methyl-4-nitro-1H-pyrazole-3-carboxamide

Obtained as a white solid after recrystallization from methanol-ethyl acetate (49%), from 1-methyl-5-(methoxycarbonyl)-4-nitropyrazole-3-carboxylic acid (J.Med.Chem. 1994, 37, 4335) using the procedure of Preparation 43.

Found: C, 36.70; H, 3.42; N, 24.33. $C_7H_8N_4O_5$ requires C, 36.85; H, 3.53; N, 24.56%.

$\delta(DMSOd_6)$: 3.87 (3H, s), 4.12 (3H, s), 7.77 (1H, s), 8.01 (1H, s).

LRMS: m/z 246 (M+18)$^+$

Preparation 45
3-Methoxycarbonyl-4-nitro-1-(pyridin-2-yl)methyl-1H-pyrazole-5-N-methylcarboxamide A mixture of the title compound of Preparation 38 (1.36 g, 4.45 mmol),1-(3-dimethylaminopropyl)-3-ethylcarbodiimide hydrochloride (853 mg, 4.45 mmol), 1-hydroxybenzotriazole hydrate (682 mg, 4.45 mmol), methylamine hydrochloride (1.20 g, 17.79 mmol) and N-ethyldiisopropylamine (3.87 ml, 22.24 mmol) in dichloromethane (30 ml) was stirred at room temperature for 18 hours. The reaction mixture was washed consecutively with water (10 ml), 0.5N hydrochloric acid (10 ml), 0.5N sodium hydroxide solution (10 ml) and water (10 ml), then dried ($MgSO_4$) and evaporated under reduced pressure. The residual orange gum was purified by column chromatography on silica gel, using an elution gradient of dichloromethane:methanol (99:1 to 95:5) to afford the title compound (220 mg, 15%) as an orange solid.

$\delta(CDCl_3)$: 3.02 (3H, d), 3.94 (3H, s), 5.67 (2H, s), 7.30 (1H, m), 7.39 (1H, d), 7.78 (1H, m), 8.55 (1H, d), 8.72 (1H, m).

LRMS: m/z 320 (M+1)$^+$

Preparation 46
3-Methoxycarbonyl-1-methyl-4-nitro-1H-pyrazole-5-N-methylcarboxamide Methylamine hydrochloride (2.16 g, 32 mmol) and triethylamine (5.87 ml, 80 mmol) were added to an ice-cold solution of the title compound of Preparation 41 (4.55 g, 16 mmol) in dichloromethane (40 ml) and the reaction stirred at room temperature for 18 hours. The reaction mixture was filtered, and the filtrate washed consecutively with water (20 ml), 1N hydrochloric acid (20 ml), 1N sodium hydroxide solution (3×20 ml) and water (20 ml). The organic solution was dried ($MgSO_4$), concentrated under reduced pressure and the residue triturated with diethyl ether to afford the title compound (1.30 g, 34%) as a beige solid.

Found: C, 39.54; H, 4.13; N, 22.90. $C_{8 H10}N_4O_5$ requires C, 39.67; H, 4.16; N, 23.13%.

$\delta(CDCl_3)$: 3.03 (3H, d), 3.96 (3H, s), 4.19 (3H, s), 7.34 (1H, m).

LRMS: m/z 243 (M+1)$^+$

Preparation 47
4-Nitro-1-(pyridin-2-yl)methyl-1H-pyrazole-3,5-dicarboxamide

A suspension of the title compound of Preparation 3 (5.0 g, 15.6 mmol) in methanol (250 ml), was saturated with ammonia gas for an hour, and the reaction stirred for a further 90 minutes at room temperature The reaction mixture was evaporated under reduced pressure, azeotroped with dichloromethane and dried under vacuum to afford the title compound (4.53 g, 100%) as a beige solid.

Found: C, 45.35; H, 3.46; N, 28.78.$C_{11}H_{10}N_6O_4$ requires C, 45.52; H, 3.47; N, 28.96%.

$\delta(DMSOd_6)$: 5.52 (2H, s), 7.29 (1H, d), 7.36 (1H, m), 7.76 (1H, s), 7.81 (1H, m), 8.04 (1H, s), 8.23 (1H, s), 8.55 (2H, m).

LRMS: m/z 291 (M+1)$^+$

Preparation 48
5-N-Methylcarboxamido-4-nitro-1-(pyridin-2-yl)methyl-1H-pyrazole-3-carboxamide An ice-cooled solution of the title compound of Preparation 45 (215 mg, 0.67 mmol) in methanol (10 ml) was saturated with ammonia, and the mixture stirred at room temperature for an hour. The reaction mixture was concentrated under reduced pressure and azeotroped with dichloromethane to afford the title compound (206 mg, 100%) as a beige foam.

$\delta(CDCl_3)$: 3.01 (3H, d), 5.60 (2H, s), 5.74 (1H, s), 7.05 (1H, s), 7.34 (1H, m), 7.40 (1H, d), 7.78 (1H, m), 8.55 (1H, d), 8.62 (1H, s).

LRMS: m/z 305 (M+1)$^+$

Preparation 49
1-Methyl-5-N-methylcarboxamido-4-nitro-1H-pyrazole-3-carboxamide

Obtained as a solid (99%) from the title compound of Preparation 46, using the procedure of Preparation 48.

Found: C, 36.89; H, 3.91; N, 30.59. $C_7H_9N_5O_4$ requires C, 37.01; H, 3.99; N, 30.83%.

$\delta(DMSOd_6)$: 2.80 (3H, d), 3.82 (3H, s), 7.74 (1H, s), 8.04 (1H, s), 9.00 (1H, m).

LRMS: m/z 245 (M+18)$^+$

Preparation 50
4-Amino-1-benzyl-3-methoxycarbonyl-1H-pyrazole-5-carboxamide

Obtained as a dark brown solid (81%) from the title compound of Preparation 42 and Raney® nickel using a similar procedure to that described in Preparation 11.

LRMS: m/z 275 (M+1)$^+$

Preparation 51
4-Amino-1-methyl-3-methoxycarbonyl-1H-pyrazole-5-carboxamide

Obtained as a white solid (99%) from the title compound of Preparation 43, using the procedure of Preparation 11.

Found: C, 42.18; H, 5.00; N, 27.35. $C_7H_{10}N_4O_3$ requires C, 42.42; H, 5.09; N, 28.37%.

$\delta(DMSOd_6)$: 3.78 (3H, s), 3.97 (3H, s), 5.18 (2H, s), 7.39 (2H, s).

LRMS: m/z 199 (M+1)$^+$

Preparation 52
4-Amino-1-methyl-5-methoxycarbonyl-1H-pyrazole-3-carboxamide

Obtained as a white solid (91%) from the tile compound of Preparation 44 and Raney nickel, using the procedure of Preparation 11.

$\delta(DMSOd_6)$: 3.82 (3H, s), 3.98 (3H, s), 5.56 (2H, s), 7.16 (1H, s), 7.34 (1H, s).

LRMS: m/z 199 (M+1)⁺

Preparation 53
4-Amino-1-(pyridin-2-yl)methyl-1H-pyrazole-3,5-dicarboxamide

Obtained as a white solid (90%) from the title compound of Preparation 47 using the procedure of Preparation 11.

δ(DMSOd$_6$): 5.28 (2H, s), 5.71 (2H, s), 6.93 (1H, d), 7.19 (1H, s), 7.28 (1H, m), 7.38 (1H, s), 7.46 (2H, s), 7.76 (1H, m), 8.48 (1H, d).

LRMS: m/z 260 (M)⁺

Preparation 54
4-Amino-5-N-methylcarboxamido-1-(pyridin-2-yl)methyl-1H-pyrazole-3-carboxamide A mixture of the title compound of Preparation 48 (200 mg, 0.66 mmol) and 10% palladium on charcoal (40 mg) in ethanol (10 ml) was hydrogenated at 30° C. and 207 kPa (30 psi), for 3 hours, then filtered. The filtrate was combined with an ethanol (30 ml) wash of the filter pad, concentrated under reduced pressure and azeotroped with dichloromethane to afford the title compound (135 mg, 75%).

δ(CDCl$_3$): 3.00 (3H, s), 5.00 (2H, s), 5.26 (2H, s), 5.55 (2H, s), 7.29 (1H, m), 7.38 (1H, d), 7.75 (1H, m), 8.54 (1H, d), 8.97 (1H, s).

Preparation 55
4-Amino-1-methyl-5-N-methylcarboxamide-1H-pyrazole-3-carboxamide

Obtained as a white solid (65%) from the title compound of Preparation 49, using the procedure of Preparation 11.

Found: C, 42.52; H, 5.86; N, 34.95. C$_7$H$_{11}$N$_5$O$_2$ requires C, 42.64; H, 5.62; N, 35.51%.

δ(DMSOd$_6$): 2.75 (3H, d), 3.90 (3H, s), 5.13 (2H, s), 7.14 (1H, s), 7.33 (1H, s), 7.60 (1H, m).

Preparation 56
3-Methoxycarbonyl-2-methyl4(2-n-propoxybenzamido)-1H-pyrazole-5-carboxamide A solution of 2-n-propoxybenzoyl chloride (644 mg, 3.25 mmol) in dichloromethane (5 ml) was added dropwise to an ice-cooled solution of the title compound of Preparation 52 (642 mg, 3.25 mmol) in pyridine (15 ml) and the reaction stirred at room temperature for 72 hours. The reaction mixture was concentrated under reduced pressure, the residue partitioned between dichloromethane (30 ml) and 1N hydrochloric acid (20 ml), and the phases separated. The organic layer was washed with 1N hydrochloric acid (2×20 ml), dried (MgSO$_4$) and evaporated under reduced pressure. The residue was purified by column chromatography on silica gel, using an elution gradient of dichloromethane:methanol (99:1 to 98:2) to afford the title compound (700 mg, 60%) as a white solid.

δ(CDCl$_3$): 1.04 (3H, t), 2.04 (2H, m), 3.88 (3H, s), 4.08 (3H, s), 4.25 (2H, t), 5.44 (1H, s), 6.70 (1H, s), 7.04 (2H, m), 7.47 (1H, m), 8.21 (1H, d), 10.82 (1H, s).

LRMS: m/z 361 (M+1)⁺

Preparation 57
3-Methoxycarbonyl-1-methyl4-(2-n-propoxybenzamido)-1H-pyrazole-5-carboxamide A solution of 2-n-propoxybenzoyl chloride (1.12 g, 5.65 mmol) in dichloromethane (5 ml) was added slowly to an ice-cooled solution of the title compound of Preparation 51 (1.12 g, 5.65 mmol) in pyridine (20 ml) and the reaction stirred at room temperature for 18 hours. The mixture was concentrated under reduced pressure, the residue partitioned between dichloromethane (60 ml) and 2N hydrochloric acid (20 ml) and the phases separated. The organic layer was washed with 2N hydrochloric acid (20 ml), dried (MgSO$_4$) and evaporated under reduced pressure to afford the title compound (2.0 g, 98%) as a white foam.

δ(CDCl$_3$): 1.06 (3H, t), 1.99 (2H, m), 3.93 (3H, s), 4.22 (5H, m), 5.72 is (1H, s), 7.09 (2H, m), 7.55 (1H, m), 8.28 (2H, m), 10.47 (1H, s).

LRMS: m/z 361 (M+I)⁺

Preparation 58
Potassium 2-methyl-7-oxo-5-(2-propoxyphenyl)-2,6-dihydro-2H-pyrazolo[4,3-d]pyrimidine-3-carboxylate A mixture of potassium t-butoxide (498 mg, 4.44 mmol) and the tide compound of Preparation 56 (400 mg, 1.11 mmol) in n-propanol (20 ml) was heated under reflux for 20 hours, then cooled. The resulting precipitate was filtered, washed with diethyl ether and dried at 60° C., to afford the title compound (286 mg, 79%) as a white solid.

δ(DMSOd$_6$): 0.80 (3H, t), 1.57 (2H, m), 3.85 (2H, t), 4.21 (3H, s), 6.98 (2H, m), 7.21 (1H, m), 7.40 (1H, d).

Preparation 59
1-Methyl-7-oxo-5-(2-n-propoxyphenyl)-1,6-dihydro-1H-pyrazolo[4,3-d]pyrimidine-3-carboxylic acid Potassium t-butoxide (2.15 g, 19.13 mmol) was added portionwise to a solution of the title compound of Preparation 57 (1.97 g, 5.47 mmol) in n-propanol (50 ml) and the reaction heated under reflux for 22 hours. The cooled reaction mixture was concentrated under reduced pressure, the residue dissolved in water (20 ml) and acidified to pH 4 with 2N hydrochloric acid. The resulting precipitate was filtered, washed with water, and dried at 60° C. to afford the title compound (1.64 g, 91%) as a white solid.

δ(DMSO$_6$): 0.96 (3H, t), 1.72 (2H, m), 4.03 (2H, t), 4.28 (3H, s), 7.06 (1H, m), 7.18 (1H, d), 7.50 (1H, m), 7.68 (1H, d), 12.20 (1H, s), 12.91 (1H, s).

LRMS: m/z 329 (M+1)⁺

Preparation 60
2-Methyl-7-oxo-5-(2-n-propoxyphenyl)-2,6-dihydro-2H-pyrazolo[4,3-d]pyrimidine-3-N-methylcarboxamide A mixture of the title compound of Preparation 58 (140 mg, 0.38 mmol), methylamine hydrochloride (29 mg, 0.42 mmol), N-ethyldiisopropylamine (220 ml, 1.28 mmol) and bromo-tris-pyrrolidino-phosphonium hexafluorophosphate (199 mg, 0.42 mmol) in dichloromethane (10 ml) and dimethylformamide (5 ml) was stirred at room temperature for 72 hours. The reaction mixture was concentrated under reduced pressure, the residue dissolved in dichloromethane (20 ml), and washed with 1N hydrochloric acid (2×10 ml), then water (10 ml), dried (MgSO$_4$) and evaporated under reduced pressure. The residue was triturated with diethyl ether to afford the title compound (125 mg, 96%) as a white solid.

δ(DMSOd$_6$): 0.95 (3H, t), 1.74 (2H, m), 2.89 (3H, d), 4.04 (2H, t), 4.37 (3H, s), 7.08 (1H, m), 7.18 (1I1, d), 7.51 (1H, m), 7.80 (1H, d), 8.34 (1H, s), 11.99 (1H, s).

LRMS: m/z 342 (M+1)⁺

Preparation 61
1-Methyl-7-oxo-5-(2-n-propoxyphenyl)-1,6-dihydro-1H-pyrazolo[4,3-d]pyrimidine-3-carboxamide A mixture of the title compound of Preparation 59 (1.57 g, 4.77 mmol) and N,N'-carbonyldiimidazole (850 mg, 5.24 mmol) in tetrahydrofuran (50 ml) was heated under reflux for 3 hours, then ice-cooled. This solution was saturated with ammonia gas, and the reaction mixture stirred at room temperature for 18 hours. The resulting precipitate was filtered, washed with ethyl acetate and dried at 60° C. to afford the title compound (1.37 g, 88%) as a white solid.

δ(DMSOd$_6$): 0.97 (3H, t), 1.73 (2H, m), 4.04 (2H, t), 4.25 (3H, s), 7.08 (1H, m), 7.19 (1H, d), 7.51 (1H, m), 7.71 (3H, m), 11.50 (1H, s).

Preparation 62
Pyridine-2-amino-5-sulphonic acid

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound (111.3 g, 75%) as a solid.

LRMS: m/z 175 (M+1)⁺

Preparation 63

Pyridine-2-amino-3-bromo-5-sulphonic acid

Bromine (99 g, 0.62 mol) was added dropwise over an hour, to a solution of the title compound of Preparation 62 (108 g, 0.62 mol) in water (600 ml) so as to maintain a steady reflux. Once the addition was complete the reaction was cooled and the resulting mixture filtered. The solid was washed with water and dried under suction to afford the title compound (53.4 g, 34%).

$\delta(DMSOd_6)$: 8.08 (1H, s), 8.14 (1H, s).

LRMS: m/z 253 (M)⁺

Preparation 64

Pyridine-3-bromo-2-chloro-5-sulphonyl chloride

A solution of sodium nitrite (7.6 g, 110 mmol) in water (30 ml) was added dropwise to an ice-cooled solution of the title compound of Preparation 63 (25.3 g, 100 mmol) in aqueous hydrochloric acid (115 ml, 20%), so as to maintain the temperature below 6° C. The reaction was stirred for 30 minutes at 0° C. and a further hour at room temperature. The reaction mixture was evaporated under reduced pressure and the residue dried under vacuum at 70° C. for 72 hours. A mixture of this solid, phosphorus pentachloride (30 g, 144 mmol) and phosphorus oxychloride (1 ml) was heated at 125° C. for 3 hours, and then cooled. The reaction mixture was poured onto ice (100 g) and the resulting solid filtered, and washed with water. The product was dissolved in dichloromethane, dried ($MgSO_4$), filtered and evaporated under reduced pressure to afford the tide compound (26.58 g, 91%) as a yellow solid.

$\delta(CDCl3)$: 8.46 (1H, s), 8.92 (1H, s).

Preparation 65

Pyridine-3-bromo-5-(4-ethylpiperazin-1-ylsulphonyl)-2-chloride

A solution of 1-ethyl piperazine (11.3 ml, 89 mmol) and triethylamine (12.5 ml, 89 mmol) in dichloromethane (150 ml) was added dropwise to an ice-cooled solution of the title compound of Preparation 64 (23 g, 79 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound (14.5 g, 50%) as an orange solid.

$\delta(CDCl_3)$: 1.05 (3H, t), 2.42 (2H, q), 2.55 (4H, m), 3.12 (4H, m), 8.24 (1H, s), 8.67 (1H, s).

Preparation 66

3-Bromo-2-ethoxy-5-(4-ethylpiperazin-1-ylsulphonyl) pyridine

A mixture of the title compound of Preparation 65 (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried ($MgSO_4$) and evaporated under reduced pressure to afford the tide compound (6.41 g, 95%) as a brown solid.

Found: C, 41.27; H, 5.33; N, 11.11. $C_{13}H_{20}BrN_3O_3S$ requires C, 41.35; H, 5.28; N, 10.99%.

$\delta(CDCl_3)$: 1.06 (3H, t), 1.48 (2H, m), 2.42 (2H, q), 2.56 (4H, m), 3.09 (4H, m), 4.54 (2H, q), 8.10 (1H, s), 8.46 (1H, s).

LRMS: m/z 380 (M+2)⁺

Preparation 67

Pyridine-2-ethoxy-5-(4-ethylpiperazin-1-ylsulphonyl)-3-carboxylic acid ethyl ester A mixture of the title compound of Preparation 66 (6.40 g, 16.92 mmol), triethylamine (12 ml), and palladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound (6.2 g, 99%) as an orange oil.

$\delta(CDCl_3)$: 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s).

LRMS: m/z 372 (M+1)⁺

Preparation 68

Pyridine-2-ethoxy-5-(4-ethylpiperazin-1-ylsulphonyl)-3-carboxylic acid

A mixture of the title compound of Preparation 67 (4.96 g, 13.35 mmol) and aqueous sodium hydroxide solution (25 ml, 2N) in ethanol (25 ml) was stirred at room temperature for 2 hours. The reaction mixture was concentrated under reduced pressure to half its volume, washed with diethyl ether and acidified to pH 5 using 4N hydrochloric acid. The aqueous solution was extracted with dichloromethane (3×30 ml), the combined organic extracts dried ($MgSO_4$) and evaporated under reduced pressure to afford the title compound (4.02 g, 88%) as a tan coloured solid.

$\delta(DMSOd_6)$: 1.18 (3H, t), 1.37 (3H, t), 3.08 (2H, q), 3.17–3.35 (8H, m), 4.52 (2H, q), 8.30 (1H, s), 8.70 (1H, s).

Preparation 69

Pyridine-2-ethoxy-5-(4-ethylpiperazin-1-ylsulphonyl)-3-carboxylic acid chloride hydrochloride Oxalyl chloride (0.77 ml, 8.85 mmol) was added dropwise to an ice-cooled solution of the title compound of Preparation 68 (1.52 g, 4.42 mmol) and dimethylformamide (2 drops) in dichloromethane (30 ml) and the reaction stirred for 18 hours at room temperature. The mixture was concentrated under reduced pressure and the residue triturated with ethyl acetate. The resulting solid was filtered, washed with diethyl ether and dried under suction to afford the title compound (1.68 g, 95%).

Found: C, 41.51; H, 5.27; N, 10.32. $C_{14}H_{21}Cl_2N_3O_4S$;$0.10CH_2Cl_2$ requires C, 41.73; H, 5.02; N, 10.36%.

$\delta(CDCl_3)$: 1.46 (6H, m), 2.95 (2H, q), 3.11 (2H, m), 3.48 (2H, m), 3.55 (2H, m), 3.92 (2H, m), 4.60 (2H, q), 8.58 (1H, s), 8.66 (1H, s), 13.16 (1H, s).

Preparation 70

2-Ethoxy-5-(4-methylpiperazin-1-ylsulphonyl)benzoic acid chloride hydrochloride

Oxalyl chloride (11.7 ml, 134 mmol) was added dropwise to an ice cold suspension of 2-ethoxy-5(4methylpiperazin-1-ylsulphonyl)benzoic acid (EP 812845) (20.0 g, 60.9 mmol) and dimethylformamide (2 drops) in dichloromethane (200 ml) over 15 minutes, and the reaction mixture stirred at room temperature for 18 hours. The mixture was concentrated under reduced pressure, the residue triturated with ether then ethyl acetate and dried at 40° C. for 16 hours, to afford the title compound, (19.6 g; 93%).

$\delta(DMSOd_6)$: 1.35 (3H, t), 2.70 (5H, m), 3.12 (2H, m), 3.41 (2H, m), 3.75 (2H, m), 4.21 (2H, q), 7.38 (1H, d), 7.83 (1H, d), 7.94 (1H, s), 11.26 (1H, s).

Preparation 71

1-Benzyl4-[2-ethoxy-5-(4-methylpiperazin-1-ylsulphonyl) benzamido]-3-methoxycarbonyl-pyrazole-5-carboxamide A solution of the title compound of Preparation 70 (4.51 g, 13.0 mmol) in dichloromethane (18 ml) was added dropwise to an ice-cooled solution of the title compound of Preparation 50 (3.56 g, 13.0 mmol) in pyridine (20 ml) and dichloromethane (2 ml), and the reaction stirred at room temperature for 20 hours. The reaction mixture was concentrated under reduced pressure, azeotroped with toluene and the residual oil partitioned between dichloromethane (50 ml) and sodium bicarbonate solution (50 ml). The phases were separated, the aqueous layer extracted with dichloromethane (2×50 ml), and the combined organic solutions dried ($Na_2SO_4$) and evaporated under reduced pressure. The residual oil was purified by column chromatography on silica gel, using an elution gradient of dichloromethane:methanol (100:0 to 90:10) and triturated with diethyl ether to afford the title compound (5.08 g, 67%) as a white solid.

δ($CDCl_3$): 1.58 (3H, t), 2.20 (3H, s), 2.41 (4H, m), 2.98 (4H, m), 3.88 (3H, s), 4.39 (2H, q), 5.70 (2H, s), 7.13 (1H, d), 7.23 (7H, m), 7.82 (1H, m), 8.56 (1H, s), 10.39 (1H, s).

LRMS: m/z 585 $(M+1)^+$

Preparation 72

1-Benzyl-7-oxo-5-[2-ethoxy-5-(4methylpiperazin-1-ylsulphonyl)phenyl]-1,6-dihydro-1H-pyrazolo[4,3-d]pyrimidine-3-carboxylic acid A mixture of the title compound of Preparation 71 (5.08 g, 8.69 mmol) and potassium t-butoxide (3.41 g, 30.4 mmol) in isopropanol (80 ml) was heated under reflux for 10 hours, then cooled. Water (80 ml) was added and the mixture acidified to pH 5 using concentrated hydrochloric acid. The resulting precipitate was filtered, washed with water and dried to afford the title compound, (3.95 g, 85%) as a white solid.

δ($DMSOd_6$): 1.34 (3H, t), 2.18 (3H, s), 2.40 (4H, m), 2.94 (4H, m), 4.23 (2H, q), 5.84 (2H, s), 7.36 (6H, m), 7.84 (1H, d), 7.94 (1H, s), 12.44 (1H, s).

LRMS: m/z 553 $(M+1)^+$

Preparation 73

4-[2-Ethoxy-5-(4-ethylpiperazin-1-ylsulphonyl)pyridin-3-ylcarboxamido]-2-(pyridin-2-yl)methyl-pyrazole-3,5-dicarboxamide Triethylamine (1.26 ml, 9.04 mmol) was added dropwise to an ice-cold suspension of the title compounds of Preparations 69 (1.20 g, 3.01 mmol) and 53 (784 mg, 3.01 mmol) in dichloromethane (50 ml) and the reaction stirred at room temperature for 18 hours. The reaction mixture was diluted with dichloromethane (50 ml), washed with water (15 ml), and saturated sodium carbonate solution (15 ml), dried ($MgSO_4$) and concentrated under reduced pressure. The residual brown foam was purified by column chromatography on silica gel, using an elution gradient of dichloromethane:methanol (98:2 to 95:5) to afford the title compound (845 mg, 49%) as a white solid.

δ($DMSOd_6$): 0.92 (3H, t), 1.49 (3H, t), 2.30 (2H, q), 2.42 (4H, m), 2.95 (4H, m), 4.70 (2H, q), 5.68 (2H, s), 7.17 (1H, d), 7.30 (1H, m), 7.50 (1H, s), 7.66 (2H, s), 7.70 (1H, s), 7.78 (1H, m), 8.50 (2H, m), 8.72 (1H, s), 10.81 (1H, s).

LRMS: m/z 587 $(M+2)^+$

Preparation 74

4-[2-Ethoxy-5-(4-ethylpiperazin-1-ylsulphonyl)pyridin-3-ylcarboxamido]-3-N-meythylcarboxamido-2-(pyridin-2-yl)methyl-pyrazole-5-carboxamide Obtained as a yellow foam (59%) from the title compounds of Preparations of 69 and 54, using the procedure of Preparation 73.

δ($CDCl_3$): 1.01 (3H, t), 1.59 (3H, t), 2.40 (2H, q), 2.53 (4H, m), 2.94 (3H, d), 3.08 (4H, m), 4.79 (2H, q), 5.32 (1H, s), 5.66 (2H, s), 6.68 (1H, s), 7.25 (2H, m), 7.70 (1H, m), 8.45 (1H, m), 8.58 (1H, d), 8.66 (1H, s), 8.86 (1H, s), 10.89 (1H, s).

LRMS: m/z 600 $(M+1)^+$

Preparation 75

4-[$^2$-Ethoxy-5-(4-ethylpiperazin-1-ylsulphonyl)pyridin-3-ylcarboxamido]-2-methyl-3-N-methylcarboxamido-pyrazole-5-carboxamide Obtained as a pink foam (26%) from the title compounds of Preparations 69 and 55, using the procedure of Preparation 73.

δ($CDCl_3$): 1.02 (3H, t), 1.57 (3H, t), 2.40 (2H, q), 2.53 (4H, m), 2.93 (3H, d), 3.10 (4H, m), 4.09 (3H, s), 4.78 (2H, q), 5.50 (1H, s), 6.68 (1H, s), 7.96 (1H, s), 8.68 (1H, s), 8.83 (1H, s), 10.75 (1H, s).

LRMS: m/z 523 $(M+1)^+$

Preparation 76

Ethyl 4-amino-3-(pyridin-2-yl)-1H-pyrazole-5-carboxylate

2-Pyridylacetonitrile (10 ml, 94.0 mmol) was added dropwise over 20 minutes to an ice-cooled solution of sodium ethoxide (34 ml, 2.76M, 94.0 mmol) in ethanol (50 ml), and the mixture stirred at 0° C. for 30 minutes. Ethyldiazoacetate (9.9 ml, 94.0 mmol) was added dropwise over 15 minutes and the reaction allowed to warm to room temperature and stirred for a furter 18 hours. Water (300 ml) was added, the mixture neutralised with solid carbon dioxide, and the resulting precipitate filtered and dried to afford the title compound, (13.0 g, 60%) as a brown solid.

δ($CDCl_3$): 1.40 (3H, t), 4.40 (2H, q), 5.78 (2H, s), 7.16 (1H, m), 7.72 (1H, m), 8.00 (1H, d), 8.57 (1H, d).

LRMS: m/z 232$(M)^+$

Preparation 77

Ethyl 4amino-3-(pyridin-3-yl)-1H-pyrazole-5-carboxylate

Obtained (64%) from 3-pyridylacetonitrile and ethyldiazoacetate, using a similar procedure to that described in Preparation 76.

δ($CDCl_3$): 1.38 (3H, t), 4.38 (2H, q), 7.38 (1H, m), 8.01 (1H, d), 8.46 (1H, d), 8.84 (1H, s).

Preparation 78

Ethyl 4-(2-n-propoxybenzamido)-3-(pyridin-2-yl)-1H-pyrazole-5-carboxylate

A mixture of the title compound of Preparation 76 (2.14 g, 10.78 mmol) and 2-n-propoxybenzoyl chloride (2.5 g, 10.78 mmol) in pyridine (25 ml) was heated at 60° C. for 5 hours, then cooled. The reaction mixture was concentrated under reduced pressure, azeotroped with toluene and the resulting oil partitioned between dichloromethane (50 ml) and sodium bicarbonate solution (50 ml). The phases were separated, the aqueous layer extracted with dichloromethane (2×50 ml) and the combined organic solutions dried ($Na_2SO_4$) and evaporated under reduced pressure. The residual brown oil was purified by column chromatography on silica gel, using an elution gradient of dichloromethane:methanol (100:0 to 97:3) to afford the title compound, (3.82 g, 90%) as a pink foam.

δ($CDCl_3$): 1.07 (3H, t), 1.38 (3H, t), 2.01 (2H, m), 4.26 (2H, t), 4.40 (2H, q), 7.06 (2H, m), 7.24 (2H, m), 7.55 (2H, m), 7.70 (1H, m), 8.26 (1H, d), 8.60 (1H, d), 10.46 (1H, s).

LRMS: m/z 395 $(M+1)^+$

Preparation 79

Ethyl 4(2-n-propoxybenzamido)-3-(pyridin-3-yl)-1H-pyrazole-5-carboxylate

Obtained (74%) from the title compound of Preparation 77 and 2-n-propoxybenzoyl chloride using the procedure described in Preparation 78.

δ($CDCl_3$): 1.02 (3H, t), 1.28 (3H, t), 1.92 (2H, m), 4.20 (2H, t), 4.36 (2H, q), 7.03 (2H, m), 7.30 (1H, m), 7.47 (1H, m), 8.02 (1H, d), 8.19 (1H, d), 8.56 (1H, d), 8.97 (1H, s), 10.00 (1H, s), 11.72 (1H, s).

Preparation 80
4-(2-n-Propoxybenzamido)-3-(pyridin-2-yl)-1H-pyrazole-5-carboxamide An ice-cooled solution of the title compound of Preparation 78 (3.10 g, 7.87 mmol) in methanol (100 ml) was saturated with ammonia gas, and the reaction mixture heated at 100° C. for 36 hours in a sealed vessel, then cooled. The mixture was evaporated under reduced pressure and the residue purified by column chromatography on silica gel, using an elution gradient of dichloromethane:methanol (100:0 to 90:10). The product was triturated with diethyl ether to afford the title compound (1.50 g, 52%) as a pink solid.

$\delta(DMSOd_6)$: 0.96 (3H, t), 1.86 (2H, m), 4.20 (2H, t), 7.05 (1H, m), 7.22 (1H, d), 7.30 (2H, m), 7.52 (3H, m), 7.86 (2H, m), 8.60 (1H, s), 10.38 (1H, s), 13.76 (1H, s).

LRMS: m/z 366 (M+1)$^+$

Preparation 81
2-Ethoxypyridine-3-carboxylic acid

A solution of potassium t-butoxide (44.9 g, 0.40 mol) in absolute ethanol (300 ml) was added slowly to a solution of 2chloronicotinic acid (30 g, 0.19 mol) in ethanol (100 ml), and the reaction heated in a sealed vessel at 170° C. for 20 hours. On cooling, the reaction mixture was concentrated under reduced pressure, the residue dissolved in water (200 ml) and acidified to pH 3 with aqueous hydrochloric acid. The aqueous solution was extracted with dichloromethane (4×200 ml), the organic phases combined, dried ($Na_2SO_4$) and concentrated under reduced pressure to afford the title compound (27.4 g, 41%) as a white solid.

$\delta(CDCl_3)$: 1.53 (3H, t), 4.69 (2H, q), 7.13 (1H, m), 8.37 (1H, d), 8.48 (1H, d).

Preparation 82
2-Ethoxypyridine-3-carboxylic acid ethyl ester

A suspension of the title compound of Preparation 81 (16.4 g, 98 mmol), and cesium carbonate (32 g, 98 mmol) in dimethylformamide (240 ml) was stirred at room temperature for 2 hours. Ethyl iodide (7.85 ml, 98 mmol) was added and the reaction stirred for a further 24 hours. The reaction mixture was concentrated under reduced pressure and the residue partitioned between aqueous sodium carbonate solution (100 ml) and ethyl acetate (100 ml). The phases were separated and the aqueous phase extracted with ethyl acetate (2×100 ml). The combined organic phases were washed with brine, dried ($Na_2SO_4$) and evaporated under reduced pressure to afford the title compound (18.0 g, 94%) as a pale yellow oil.

$\delta(CDCl_3)$: 1.41 (6H, m), 4.36, (2H, q), 4.48 (2H, q), 6.90 (1H, m), 8.12 (1H, d), 8.28 (1H, d).

Preparation 83
2-Ethoxy-5-nitropyridine-3-carboxylic acid ethyl ester

Ammonium nitrate (5.36 g, 66 mmol) was added portionwise to an ice-cooled solution of the title compound of Preparation 82 (4.66 g, 22.3 mmol) in trifluoroacetic anhydride (50 ml) and the reaction stirred for 18 hours at room temperature. The reaction mixture was carefully poured into ice water (200 ml) and the resulting suspension stirred for an hour. The precipitate was filtered off, washed with water and dried under suction to afford the tile compound (3.29 g, 61%).

$\delta(CDCl_3)$: 1.41 (3H, t), 1.48 (3H, t), 4.41 (2H, q), 4.62 (2H, q), 8.89 (1H, s), 9.16 (1H, s).

Preparation 84
2-Ethoxy-5-nitropyridine-3-carboxylic acid

Aqueous sodium hydroxide solution (4 ml, 5N, 20 mmol) was added dropwise to a solution of the title compound of Preparation 83 (5.1 g, 20 mmol) in ethanol (100 ml) and the reaction stirred at room temperature for 18 hours. The reaction mixture was concentrated under reduced pressure, the residue suspended in water (50 ml) and acidified to pH 3 with hydrochloric acid. This aqueous solution was extracted with ethyl acetate (3×100 ml), the combined organic layers washed with brine (100 ml), dried ($Na_2SO_4$) and evaporated under reduced pressure to give a beige solid. The crude product was recrystallised from ethyl acetate/hexane to afford the title compound (3.32 g, 78%) as beige crystals.

$\delta(CDCl_3)$: 1.55 (3H, t), 4.78 (2H, q), 9.17 (1H, s), 9.23 (1H, s).

Preparation 85
4-Amino-3-(pyridin-3-yl)-1H-pyrazole-5-carboxamide

The title compound of Preparation 77 (2.9 g, 12.5 mmol) was dissolved in saturated methanolic ammonia solution (50 ml) and the reaction heated at 100° C. for 18 hours in a sealed vessel. The cooled mixture was evaporated under reduced pressure to afford the title compound (2.53 g, 99%) as a brown solid.

$\delta(DMSOd_6)$: 3.28 (2H, s), 5.08 (2H, s), 7.43 (1H, m), 8.09 (1H, d), 8.46 (1H, d), 8.95 (1H, s).

LRMS: m/z 204 (M+1)$^+$

Preparation 86
4-[2-Ethoxy-5-nitropyridin-3-ylcarboxamido]-3-(pyridin-3-yl)-1H-pyrazole-5-carboxamide A mixture of the title compounds of Preparations 84 (2.37 g, 11.2 mmol) and 85 (2.5 g, 12.3 mmol), N-ethyldiisopropylamine (3.87 ml, 22.4 mmol), 1-hydroxybenzotriazole hydrate (1.66 g, 12.3 mmol) and 1-(3-dimethylaminopropyl)-3-ethylcarbodiimide hydrochloride (2.36 g, 12.3 mmol) in tetrahydrofuran (60 ml) was stirred at room temperature for 48 hours. The mixture was concentrated under reduced pressure, suspended in ethyl acetate (100 ml), washed with brine (25 ml), 2N hydrochloric acid (25 ml), dried ($MgSO_4$) and concentrated under reduced pressure. The residue was purified by column chromatography on silica gel, using dichloromethane:methanol (97.5:2.5) as eluant to afford the title compound, (1.82 g, 41%) as a yellow solid.

$\delta(DMSOd_6)$: 1.42 (3H, t), 4.62 (2H, q), 7.42 (2H, m), 7.63 (1H, s), 7.95 (1H, s), 8.51 (1H, d), 8.66 (1H, s), 8.80 (1H, s), 9.18 (1H, d), 10.48 (1H, s), 13.78 (1H, s).

LRMS: m/z 398 (M+1)$^+$

Preparation 87
4-[5-Amino-2-ethoxypyridin-3-ylcarboxamido]-3-(pyridin-3-yl)-1H-pyrazole-5-carboxamide A mixture of the tile compound of Preparation 86 (1.8 g, 4.53 mmol) and Raney® nickel (800 mg) in ethanol (100 ml) was hydrogenated at 345 kPa (50 psi) and 50° C. for 18 hours. The cooled mixture was filtered through Arbocel®, the filter pad washed well with ethanol (100 ml) and the filtrate evaporated under reduced pressure to afford the title compound (1.65 g, 99%) as a white solid.

LRMS: m/z 368 (M+1)$^+$

Preparation 88
2-n-Propoxyphenyl-3-(pyridin2-yl)-1,6-dihydro-7H-pyrazolo[4,3-d]pyrimidin-7-one Potassium t-butoxide (1.60 g, 14.44 mmol) was added to a suspension of the title compound of Preparation 80 (1.50 g, 4.11 mmol) in isopropanol (40 ml) and the mixture heated under reflux for 5 hours, then cooled. Water (50 ml) was added, the mixture neutralised using solid carbon dioxide and the resulting precipitate filtered and dried, to afford the title compound (1.26 g, 88%) as a pale yellow solid.

$\delta(DMSOd_6)$: 0.96 (3H, t), 1.75 (2H, m), 4.06 (2H, t), 7.10 (1H, m), 7.19 (1H, d), 7.39 (1H, m), 7.50 (1H, m), 7.82 (1H, d), 7.97 (1H, m), 8.48 (1H, d), 8.67 (1H, d), 11.82 (1H, br s).

LRMS: m/z 348 (M+1)+

Preparation 89

2-n-Propoxyphenyl-3-(pyridin-3-yl)-1,6-dihydro-7H-pyrazolo[4,3-d]pyrimidin-7-one An ice-cooled solution of the title compound of Preparation 79 (2.5 g, 6.33 mmol) in methanol (100 ml) was saturated with ammonia and the reaction heated at 100° C. for 18 hours, then cooled and evaporated under reduced pressure. A mixture of this product, and potassium t-butoxide (1.9 g, 17.0 mmol) in isopropanol (40 ml) was heated under reflux for 6 hours, then cooled. Water (20 ml) was added, the mixture neutralised using solid carbon dioxide and the resulting precipitate filtered and dried to afford the title compound, (950 mg, 43%).

δ(CDCl$_3$): 1.12 (3H, t), 1.99 (2H, m), 4.18 (2H, t), 7.02 (1H, d), 7.12 (1H, m), 7.40 (2H, m), 8.55 (1H, d), 8.64 (1H, d), 9.71 (1H, s), 11.32 (1H, s).

Preparation 90

5-[5-Amino-2-ethoxypyridin-3-yl]-3-(pyridin-3-yl)-1,6-dihydro-7H-pyrazolo[4,3-d]pyrimidin-7-one A mixture of the title compound of Preparation 87 (1.45 g, 3.95 mmol) and potassium t-butoxide (2.66 g, 23.7 mmol) in ethanol (70 ml) was heated under reflux for 72 hours, then cooled. The reaction mixture was evaporated under reduced pressure and the residue purified by column chromatography on silica gel, using dichloromethane:methanol (97.5:2.5) as eluant to afford the title compound (10 g, 73%) as a yellow solid.

δ(MSOd$_6$): 1.27 (3H, t), 4.27 (2H, q), 5.02 (2H, s), 7.49 (1H, m), 7.59 (1H, s), 7.65 (1H, s), 8.58 (2H, m), 9.46 (1H, s), 11.98 (1H, s), 14.48 (1H, s).

LRMS: m/z 350 (M+1)+

Preparation 91

5-(2-n-Propoxyphenyl)-3-(pyridin-2-yl)-2-(pyridin-2-yl)methyl-2,6-dihydro-7H-pyrazolo[4,3-d]pyrimidin-7-one Sodium hydride (63 mg, 60%, 1.59 mmol) was added to a solution of the title compound of Preparation 88 (500 mg, 1.44 mmol) in dimethylformamide (10 ml), and the mixture stirred at room temperature for 45 minutes. A solution of 2-(chloromethyl)pyridine (obtained from 284 mg, 1.73 mmol of the hydrochloride) in dimethylformamide (5 ml), was added dropwise and the reaction mixture stirred at room temperature for 18 hours. Water (2 ml) was added, the mixture partitioned between ethyl acetate (25 ml) and sodium bicarbonate solution (25 ml) and the phases separated. The aqueous layer was extracted with ethyl acetate (2×25 ml), the combined organic solutions dried (Na$_2$SO$_4$) and evaporated under reduced pressure. The residual pink solid was purified by column chromatography on silica gel, using an elution gradient of dichloromethane:methanol (100:0 to 97:3) and repeated using dichloromethane:methanol:0.88 ammonia (100:0:0 to 98:2:1) to afford the title compound (230 mg, 36%) as a white solid.

δ(CDCl$_3$): 1.14 (3H, t), 1.99 (2H, m), 4.18 (2H, t), 6.10 (2H, s), 6.99 (1H, d), 7.04 (1H, d), 7.12 (1H, m), 7.18 (1H, m), 7.26 (1H, m), 7.46 (1H, m), 7.56 (1H, m), 7.83 (1H, m), 8.54 (1H, d), 8.60 (1H, d), 8.69 (1H, d), 8.77 (1H, d), 11.40 (1H, s).

LRMS: m/z 440 (M+2)+

Preparation 92

5-(2-n-Propoxyphenyl)-3-(pyridin-3-yl)-2-(pyridin-2-yl)methyl-2,6-dihydro-7H-pyrazolo[4,3-d]pyrimidin-7-one Obtained (60%) from the title compound of Preparation 89 and 2(chloromethyl)pyridine, using a similar procedure to that described in Preparation 91.

δ(CDCl$_3$): 1.20 (3H, t), 2.04 (2H, m), 4.22 (2H, t), 6.05 (2H, s), 7.08 (1H, d), 7.19 (3H, m), 7.48 (2H, m), 7.64 (1H, m), 8.61 (3H, m), 8.74 (1H, d), 9.79 (1H, s), 11.48 (1H, s).

LRMS: m/z 439 (M+1)+

Preparation 93

5-[2-Ethoxy-5-(4-ethylpiperazin-1-ylsulphonyl)pyridin-3-yl]-3-(pyridin-3-yl)-1H-1,6-dihydro-7H-pyrazolo[4,3-d]pyrimidin-7-one Sodium nitrite (240 mg, 3.43 mmol) was added portionwise to a cooled (−20° C.) solution of the title compound of Preparation 90 (750 mg, 2.15 mmol) in concentrated hydrochloric acid (30 ml) and acetic acid (15 ml), and the mixture allowed to warm to 0° C. over 2 hours. The mixture was re-cooled to −20° C., liquid sulphur dioxide (9 ml) and copper (II) chloride (900 mg, 6.64 mmol) in water (2 ml) and acetic acid (10 ml) were added, and the reaction mixture allowed to warm to room temperature and stirred for a further 2 hours. The mixture was poured into ice and this aqueous solution extracted with dichloromethane (3×50 ml), the combined organic extracts dried (MgSO$_4$) and evaporated under reduced pressure to give a yellow solid. A mixture of this intermediate sulphonyl chloride, N-thylpiperazine (1.05 g, 9.16 mmol) and N-ethyldiisopropylamine (1.58 ml, 9.16 mmol) in ethanol (10 ml) was stirred at room temperature for 18 hours. The mixture was concentrated under reduced pressure and the residue partitioned between dichloromethane (20 ml) and water (10 ml) and the layers separated. The organic phase was extracted with aqueous citric acid solution (2×20 ml), and these combined extracts neutralised using 1N sodium hydroxide solution. This aqueous solution was re-extracted with dichloromethane:methanol (90:10) (3×30 ml), the combined organic extracts dried (MgSO$_4$) and evaporated under reduced pressure. The product was purified by column chromatography on silica gel, using dichloromethane:methanol (97.5:2.5) as eluant to afford the title compound (320 mg, 29%) as a white solid.

δ(DMSOd$_6$): 0.90 (3H, t), 1.30 (3H, t), 2.25 (2H, q), 2.39 (4H, m), 2.95 (4H, m), 4.48 (2H, q), 7.46 (1H, m), 8.28 (1H, s), 8.52 (2H, m), 8.62 (1H, s), 9.41 (1H, s), 12.44 (1H, s), 14.57 (1H, s).

LRMS: m/z 511 M+1)+

Preparation 94

2-Methyl-pyrimidine-N-oxide

A freshly prepared solution of sodium (11.5 g, 0.50 mol) in ethanol (170 ml) was added dropwise over an hour to a suspension of hydroxylamine hydrochloride (34.75 g, 0.50 mol) and phenolphthalein (50 mg) in ethanol (200 ml) so as to maintain a colourless solution, and the reaction stirred at room temperature for 3 hours. Acetonitrile (26 ml, 0.50 mol) was added, and the reaction stirred for a further 2 hours at room temperature, and then at 45° C. for 48 hours. The reaction mixture was is filtered, and concentrated under reduced pressure to a volume of 100 ml. The solution was cooled to 0° C. and the resulting precipitate filtered and dried under suction to give white crystals (9.9 g). Boron trifluoride diethyl ether complex (9.5 ml, 75 mmol) followed by 1,1,3,3-tetramethoxypropane (11.5 ml, 70 mmol) were added to a solution of dimethylformamide (100 ml) in toluene (10 ml). 1-Hydroxymino-2-ethylamine (5.0 g, 67.5 mmol) was added and the reaction heated under reflux for 45 minutes, then cooled. The mixture was concentrated under reduced pressure and the residual brown oil partitioned between dichloromethane:methanol (80:20) (100 ml) and aqueous sodium carbonate solution (100 ml). The phases were separated, the aqueous layer extracted with dichloromethane:methanol (80:20) (10×50 ml) and the combined organic extracts dried (MgSO$_4$) and concentrated under reduced pressure. The residue was purified by column chromatography on silica gel, using dichloromethane:methanol (98:2) as eluant to afford the title compound (2.5 g, 34%) as an orange solid.

δ(CDCl$_3$): 2.74 (3H, s), 7.19 (1H, m), 8.16 (1H, d), 8.39 (1H, d).

Preparation 95
2-(Chloromethyl)pyrimidine

A mixture of the title compound of Preparation 94 (2.5 g, 22.7 mmol) in phosphorous oxychloride (18 ml, 193 mmol) was heated under reflux for 2 hours, then cooled. The mixture was poured into ice and neutralised using solid sodium carbonate over 3 hours. The aqueous solution was extracted with dichloromethane (3×100 ml), the combined organic extracts dried (MgSO$_4$) and concentrated under reduced pressure. The residual brown oil was purified by column chromatography on silica gel, using an elution gradient of dichloromethane:methanol (100:0 to 97:3) to afford the title compound (510 mg, 17%).

δ(CDCl$_3$): 4.72 (2H, s), 7.22 (1H, m), 8.75 (2H, d).
LRMS: m/z 129 (M+1)$^+$

Preparation 96
4-Nitro-1H-pyrazole-5-carboxamide

Oxalyl chloride (33.3 ml, 0.4 mol) was added dropwise over 15 minutes to an ice-cold suspension of 4nitro-1H-pyrazole-5-carboxylic acid (40.0 g, 0.25 mol) and dimethylformamide (3 drops) in dichloromethane (400 ml). The mixture was allowed to warm to room temperature and stirred for 24 hours. Additional oxalyl chloride (16.7 ml, 0.2 mol) was added and the reaction stirred for a further 24 hours. The reaction mixture was filtered, the filtrate evaporated under reduced pressure and redissolved in tetrahydrofuran (400 ml). This solution was cooled in an ice-bath, ammonia bubbled through for an hour, and the mixture purged with nitrogen for 30 minutes. The reaction mixture was concentrated under reduced pressure, the residue triturated with water, and the solid filtered and dried under vacuum to afford the title compound (34.7 g, 86%) as a white solid.

δ(DMSOd$_6$): 7.60–8.10 (3H, m), 8.68 (1H, s).

Preparation 97
2-Methyl4-nitro-pyrazole-5-carboxamide

A mixture of the title compound of preparation 96 (35.5 g, 0.22 mol), cesium carbonate (79.7 g, 0.24 mol) and methyl iodide (34.7 g, 0.24 mol) in dimethylformamide (200 ml) was stirred at room temperature for 4 days. The reaction mixture was concentrated under reduced pressure and the residue azeotroped with xylene. The resulting brown gum was triturated with hot ethyl acetate (6×400 ml) and hot methanol/dichloromethane (4×500 ml), the resulting suspensions filtered and the combined filtrates evaporated under reduced pressure. The residual brown solid was purified by column chromatography on silica gel, using an elution gradient of ethyl acetate:hexane (30:70 to 100:0) to afford the title compound, (11.5 g, 31%) as a solid.

δ(CDCl$_3$): 4.03 (3H, s), 5.88 (1H, s), 7.80 (1H, s), 8.25 (1H, s).

Preparation 98
4-Amino-2-methyl-pyrazole-5-carboxamide

A mixture of the title compound of preparation 97 (5.0 g, 30.0 mmol) and 10% palladium on charcoal (50 mg) in methanol (200 ml) was hydrogenated at 30 psi(207 kPa) and 50° C. for 18 hours. The cooled mixture was filtered through Arbocel®, the filter pad washed with methanol, and the combined filtrate evaporated under reduced pressure to afford the title compound, (4.2 g, 100%) as a pink solid.

δ(DMSOd$_6$): 3.72 (3H, s), 4.60 (2H, s), 6.88 (1H, s), 7.05 (2H, m).

Preparation 99
4-Amino-3-bromo2-methyl-pyrazole-5-carboxamide

Bromine (92 ml, 1.8 mmol) was added to a solution of the title compound of preparation 98 (250 mg, 1.8 mmol) in acetic acid (10 ml), and the reaction stirred for an hour at room temperature. The mixture was concentrated under reduced pressure, and the residue azeotroped with toluene. The crude product was purified by column chromatography on silica gel, using ethyl acetate:methanol:0.88 ammonia (90:10:1) as eluant, to afford the title compound (250 mg, 64%).

δ(DMSOd$_6$): 3.76 (3H, s), 4.64 (2H, s), 7.14 (1H, s), 7.27 (1H, s)

Preparation 100
3-Bromo4-[2-ethoxy-5-(4-ethylpiperazin-1-ylsulphonyl) pyridin-3-yl-carboxamido]-2-methyl-pyrazole-5-carboxamide A mixture of the title compounds of preparation 99 (250 mg, 1.1 mmol), and 68 (429 mg, 1.25 mmol), N-ethyldiisopropylamine (294 mg, 2.3 mmol) and 2-chloro-1-methylpyridinium iodide (363 mg, 1.4 mmol) in dichloromethane (10 ml), was stirred at room temperature for 18 hours. The mixture was concentrated under reduced pressure and the residue partitioned between water (20 ml) and ethyl acetate (20 ml), and the phases separated. The aqueous phase was extracted with ethyl acetate (2×20 ml), and the combined organic solutions dried (Na$_2$SO$_4$), and evaporated under reduced pressure. The residual brown gum was purified by column chromatography on silica gel, using an elution gradient of methanol:ethyl acetate (5:95 to 7:93) to afford the title compound, (310 mg, 50%).

δ(CDCl$_3$): 1.12 (3H, t), 1.60 (3H, t), 2.41 (2H, q), 2.55 (4H, m), 3.14 (4H, m), 3.96 (3H, s), 4.78 (2H, q), 5.34 (1H, s), 6.62 (1H, s), 8.67 (1H, s), 8.86 (1H, s), 10.39 (1H, s).
LRMS: m/z 546 (M+2)$^+$

Preparation 101
3-Bromo5-[2-ethoxy-5-(4-ethylpiperazin-1-ylsulphonyl) pyridin-3-yl]-2-methyl-2,6-dihydro-7H-pyrazolo[4,3-d] pyrimidin-7-one A mixture of the title compound of preparation 100 (815 mg, 1.2 mmol), and potassium bis(trimethylsilyl)amide (439 mg, 2.2 mmol) in 3-methyl-3-pentanol (60 ml) was stirred at 125° C. in a sealed vessel for 20 hours. The cooled reaction was evaporated under reduced pressure and the residue purified by column chromatography on silica gel, using an elution gradient of ethyl acetate:diethylamine (95:5 to 90:10) to afford the title compound, (360 mg, 46%).

δ(CDCl$_3$): 1.02 (3H, t), 1.60 (3H, t), 2.41 (2H, q), 2.58 (4H, m), 3.16 (4H, m), 4.18 (3H, s), 4.76 (2H, q), 8.65 (1H, s), 9.13 (1H, s), 10.77 (1H, s).
LRMS: m/z 528 (M+2)$^+$

Preparation 102
2-(2-Methoxyethoxy)pyridine-3-carboxylic acid

Potassium t-butoxide (45.0 g, 0.40 mol) was added portion-wise to ice-cold 2-methoxyethanol (175 ml), and the resulting solution added to a suspension of 2-chloronicotinic acid (30.0 g, 0.19 mol) in 2-methoxyethanol (175 ml). The reaction mixture was heated under reflux for 26 hours, then cooled and concentrated under reduced pressure. The residue was diluted with water (200 ml), the pH of the solution adjusted to 5 using concentrated hydrochloric acid, and extracted with dichloromethane (3×). The combined organic extracts were washed with brine, dried (MgSO$_4$), evaporated under reduced pressure and azeotroped with toluene, to afford the title compound, (30.54 g, 81%).

δ(CDCl$_3$): 3.42 (3H, s), 3.80 (2H, t), 4.72 (2H, t), 7.14 (1H, m), 8.36 (1H, m), 8.45 (1H, m).
LRMS: m/z 198 (M+1)$^+$

Preparation 103
2-(2-Methoxyethoxy)-5-nitropyridine-3-carboxylic acid

Ammonium nitrate (21.8 g, 273.0 mmol) was added portion-wise to an ice-cooled solution of the title compound of preparation 102 (30.5 g, 155.0 mmol) in trifluoroacetic anhydride (110 ml), and once addition was complete, the reaction was allowed to warm to 10° C., and initiation occurred. The reaction mixture was re-cooled using an ice-bath, and then stirred at room temperature for an hour. Tlc analysis showed starting material remaining, so the reaction was cooled in an ice-bath, additional ammonium nitrate (12.4 g, 155.0 mmol) was added portionwise, and the reaction stirred at room temperature for a further hour. The reaction was poured onto ice (300 g), the resulting precipitate filtered, washed with water and dried under vacuum to afford the title compound, (25 g, 67%).

δ(CDCl$_3$): 3.44 (3H, s), 3.82 (2H, t), 4.61 (2H, t), 9.16 (1H, s), 9.21 (1H, s).

LRMS: m/z 243 (M+1)$^+$

Preparation 104

2-Ethoxy-5-nitropyridine-3-carboxamide

N,N-Dimethylformamide (2 drops) was added to an ice-cold solution of the title compound of preparation 84 (3.0 g, 13.9 mmol) and oxalyl chloride (5 ml, 57.0 mmol) in dichloromethane (30 ml), and the reaction then stirred at room temperature for 2 hours. The reaction mixture was concentrated under reduced pressure and azeotroped with dichloromethane. The residue was dissolved in dichloromethane (30 ml), the solution cooled in an ice-bath, 0.88 ammonia (5 ml) added, and the reaction stirred for 15 minutes. The mixture was partitioned between dichloromethane and water and the layers separated. The organic phase was washed with aqueous saturated sodium bicarbonate solution, brine, then dried (MgSO$_4$) and evaporated under reduced pressure. The residual yellow solid was triturated with diethyl ether, filtered and dried to afford the title compound (2.4 g, 83%).

δ(CDCl$_3$): 1.56 (3H, t), 4.74 (2H, q), 6.14 (1H, br, s), 7.66 (1H, br, s), 9.18 (1H, d), 9.29 (1H, d).

LRMS: m/z 229 (M+18)$^+$

Preparation 105

2-(2-Methoxyethoxy)-5-nitropyridine-3-carboxamide

The title compound was obtained as a pale yellow solid (84%) from the title compound of preparation 103, following the procedure described in preparation 104.

δ(CDCl$_3$): 3.43 (3H, s), 3.80 (2H, t), 4.78 (2H, t), 6.12 (1H, br, s), 7.80 (1H, br, s), 9.15 (1H, d), 9.25 (1H, d).

LRMS: m/z 264 (M+23)$^+$

Preparation 106

2-Ethoxy-5-nitropyridine-3-carbonitrile

Trifluoroacetic anhydride (3.46 g, 16.5 mmol) in dioxan (5 ml) was added to an ice-cold solution of the title compound of preparation 104 (2.32 g, 11.0 mmol) and pyridine (2.17 g, 27.5 mmol) in dioxan (15 ml), and the solution stirred at room temperature for 3 hours. The mixture was concentrated under reduced pressure and the residue partitioned between ethyl acetate and water. The layers were separated and the organic phase washed consecutively with hydrochloric acid (2N, 2×), aqueous saturated sodium bicarbonate solution, then brine. The solution was dried (MgSO$_4$) and evaporated under reduced pressure. The residue was purified by column chromatography on silica gel using an elution gradient of pentane:ethyl acetate (100:0 to 95:5) to afford the title compound (1.73 g, 81%).

δ(CDCl3): 1.50 (3H, t), 4.63 (2H, q), 8.66 (1H, d), 9.20 (1H, d).

Preparation 107

2-(2-Methoxyethoxy)-5-nitropyridine-3-carbonitrile

The title compound was prepared from the title compound of preparation 105, following a similar procedure to that described in preparation 106. The crude product was purified by trituration, and filtration from diethyl ether to give the desired product, (18.27 g, 97%) as a solid.

δ(CDCl$_3$): 3.42 (3H, s), 3.81 (2H, t), 4.76 (2H, t), 8.68 (1H, d), 9.20 (1H, d).

Preparation 108

2-Ethoxy-5-nitropyridine-3-carboximidamide acetate

The title compound of preparation 106 (11.0 g, 57.0 mmol) was added "in one portion" to a cooled (−10° C.) solution of ethanol saturated with HCl gas (100 ml), and the reaction stirred at this temperature for 8 hours. The reaction was evaporated under reduced pressure, the residue triturated with diethyl ether, and the precipitate filtered off. The solid was partitioned between ethyl acetate and aqueous saturated sodium bicarbonate solution, and the layers separated. The organic phase was washed with aqueous saturated sodium bicarbonate solution, brine, then dried (MgSO$_4$), and evaporated under reduced pressure to give a white solid, 4.25 g. Ammonium acetate (3.61 g, 46.9 mmol) was added to a solution of this intermediate imidate (8.62 g) in ethanol (80 ml), and the reaction heated under reflux for an hour. Tlc analysis showed starting material remaining, so additional ammonium acetate (0.5 g, 6.5 mmol) was added, and the reaction heated under reflux for a further 30 minutes. The cooled reaction mixture was evaporated under reduced pressure and the residue triturated with diethyl ether. The resulting solid was filtered off, and dried under vacuum to afford the title compound (8.26 g).

δ(DMSOd$_6$): 1.38 (3H, t), 1.77 (3H, s), 4.54 (2H, q), 8.74 (1H, d), 9.20 (1H, d).

LRMS: m/z 211 (M+1)$^+$

Preparation 109

2-(2-Methoxyethoxy)-5-nitropyridine-3-carboximidamide formate

The title compound was obtained as a pale brown solid (53%) from the title compound of preparation 107 and ammonium formate, in 2-methoxyethanol, following a similar procedure to that described in preparation 108.

δ(DMSOd$_6$): 3.29 (3H, s), 3.73 (2H, t), 4.60 (2H, t), 8.40 (1H, s), 8.81 (1H, d), 9.24 (1H, d).

LRMS: m/z 241 (M+1)$^+$

Preparation 110

Ethyl 2-ethoxy-1-methyl-pyrazole-4-carboxylate

Diethyl azodicarboxylate (1.3 ml, 7.5 mmol) was added dropwise to a solution of ethyl 2-hydroxy-1-methyl-pyrazole carboxylate (Chem. Pharm. Bull; 1983; 31; 1228), (880 mg, 5.0 mmol), and triphenylphosphine (2.03 g, 7.5 mmol) in ethanol (0.3 ml, 5.0 mmol) and tetrahydrofuran (100 ml), and the reaction stirred at room temperature for 4 hours. The mixture was concentrated under reduced pressure, the residue partitioned between dichloromethane and water, and the layers separated. The aqueous phase was extracted with dichloromethane, the combined organic solutions washed consecutively with water, 2N aqueous sodium hydroxide, water and finally brine. The solution was then dried (Na$_2$SO$_4$), and evaporated under reduced pressure. The crude product was purified by column chromatography on silica gel using dichloromethane as eluant to afford the title compound (768 mg, 79%), as a crystalline solid.

δ(CDCl$_3$): 1.39 (6H, m), 3.68 (3H, s), 4.10 (2H, q), 4.38 (2H, q), 6.00 (1H, s).

LRMS: m/z 199 (M+1)$^+$

Preparation 111

Ethyl 2-ethoxy-1-methyl-3-nitro-pyrazole-4-carboxylate

Fuming nitric acid (0.43 ml) was added dropwise to ice-cooled concentrated sulphuric acid (2.6 ml), and the resulting solution warmed to 40° C. The title compound of preparation 110 (433 mg, 2.18 mmol) was added portionwise, and the reaction mixture stirred for a further 50 minutes. The reaction was poured carefully onto ice, and the resulting mixture extracted with dichloromethane. The combined organic extracts were washed with water, and brine, then dried (Na$_2$SO$_4$), and evaporated under reduced pressure to afford the title compound, (301 mg, 57%) as an orange oil.

δ(CDCl$_3$): 1.40 (3H, t), 1.48 (3H, t), 3.78 (3H, s), 4.39–4.55 (4H, m).

LRMS: m/z 244 (M+1)$^+$

Preparation 112

Ethyl 3-amino-2ethoxy-1-methyl-pyrazole-4-carboxylate

A mixture of the title compound of preparation 111 (301 mg, 1.24 mmol) and 10% palladium on charcoal (60 mg) in ethanol (12 ml) was hydrogenated at 60 psi (414 kPa), and room temperature for 3 hours. The reaction mixture was filtered through Arbocel®, and the filtrate evaporated under reduced pressure. The residue was purified by column chromatography on silica gel using an elution gradient of dichloromethane:methanol (100:0 to 99:1) to afford the title compound, (140 mg, 53%).

δ(CDCl$_3$): 1.38 (6H, m), 3.72 (5H, s), 4.17 (2H, q), 4.39 (2H, q).

LRMS: m/z 214 (M+1)$^+$

Preparation 113

5-(2-Ethoxy-5-nitropyridine-3-yl)-2-methyl-2,6-dihydro-7H-pyrazolo[4,3-d]pyrimidin-7-one A mixture of the title compounds of preparations 98 (3.85 g, 27.5 mmol) and 108 (8.26 g, 30.6 mmol) in 3-methyl-3-pentanol (80 ml) were heated under reflux for 2½ hours, then cooled. The reaction mixture was partitioned between dichloromethane and hydrochloric acid (2N), and the resulting precipitate filtered, washed with water and diethyl ether, and dried. The filtrate was separated, and the organic layer washed with hydrochloric acid (2N), saturated aqueous sodium bicarbonate solution, brine, then dried (MgSO$_4$) and evaporated under reduced pressure. The residue was triturated with diethyl ether, and the resulting solid filtered and dried. The isolated solids were combined to provide the title compound (6.9 g, 79%).

δ(DMSOd$_6$): 1.35 (3H, t), 4.10 (3H, s), 4.54 (2H, q1), 8.39 (1H, s), 8.70 (1H, d), 9.19 (1H, d), 11.92 (1H, s).

LRMS: m/z 317 (M+1)$^+$

Found: C, 49.36; H, 3.82; N, 26.57. C$_{13}$H$_{12}$N$_6$O$_4$ requires C, 49.18; H, 3.77; N, 26.53%.

Preparation 114

5-[2-(2-Methoxyethoxy)-5-nitropyridin-3-yl]-2-methyl-2,6-dihydro7H-pyrazolo[4,3-d]pyrimidin-7one The title compound was obtained as a yellow solid from the title compounds of preparations 98 and 109, following a similar procedure to that described in preparation 113.

δ(DMSOd$_6$): 3.23 (3H, s), 3.70 (2H, t), 4.10 (3H, s), 4.60 (2H, t), 8.40 (1H, s), 8.77 (1H, d), 9.18 (1H, d).

Preparation 115

3-Ethoxy-5-(2-ethoxy-5-nitropyridin-3-yl)-2-methyl-2,6-dihydro-7H-pyrazolo[4,3-d]pyrimidin-7-one A solution of the title compounds of preparations 108 (177 mg, 0.66 mmol) and 112 (140 mg, 0.66 mmol) in 3-methyl-3-pentanol (5 ml) was heated at 130° C. for 3 hours. The cooled reaction was partitioned between water and dichloromethane, and the layers separated. The aqueous phase was extracted with dichloromethane, the combined organic solutions washed with brine, then dried (Na$_2$SO$_4$) and evaporated under reduced pressure. The crude product was purified by column chromatography on silica gel using dichloromethane:methanol (99.5:0.5) as eluant to afford the title compound, (55 mg, 18%) as a yellow solid.

δ(CDCl$_3$): 1.58 (6H, m), 3.91 (3H, s), 4.80 (2H, q), 4.95 (2H, q), 9.15 (1H, d), 9.39 (1H, d), 10.54 (1H, s).

LRMS: m/z 383 (M+23)$^+$

Preparation 116

3-Bromo-5-(2-ethoxy-5-nitropyridin-3-yl)-2-methyl-2,6-dihydro-7H-pyrazolo[4,3-d]pyrimidin-7-one A mixture of the title compound of preparation 113 (6.9 g, 21.8 mmol), bromine (1.35 ml, 26.2 mmol), and sodium acetate (2.7 g, 32.7 mmol) in acetic acid (100 ml) was heated under reflux for 7 hours, then allowed to cool. Additional bromine (0.35 ml, 6.8 mmol) was added and the reaction stirred at room temperature for a further 18 hours. The reaction mixture was concentrated under reduced pressure and azeotroped with toluene. The residue was partitioned between dichloromethane and water and the resulting precipitate filtered off, washed with dichloromethane, water, then diethyl ether and dried. The filtrate was separated, and the organic layer washed with aqueous saturated sodium bicarbonate solution, and brine, then dried (MgSO$_4$) and evaporated under reduced pressure to give a yellow solid. The isolated solids were combined, suspended in ethyl acetate, and stirred for 30 minutes. The resulting precipitate was filtered off, and dried to afford the title compound (7.66 g, 89%).

δ(DMSOd$_6$): 1.35 (3H, t), 4.10 (3H, s), 4.54 (2H, q), 8.70 (1H, d), 9.20 (1H, d), 12.16 (1H, s).

LRMS: m/z 394, 396 (M+1)$^+$

Found: C, 39.51; H, 2.80; N, 21.27. C$_{13}$H$_{11}$BrN$_6$O$_4$ requires C, 39.63; H, 2.73; N, 21.36%.

Preparation 117

3-Bromo-5-[2-(2-methoxyethoxy)-5-nitropyridin-3-yl]-2-methyl-2,6-dihydro-7H-pyrazolo[4,3-d]pyrimidin-7-one Bromine (500 μl, 10.0 mmol) was added dropwise to a suspension of the title compound of preparation 114 (2.64 g, 7.62 mmol) and sodium acetate (1.25 g, 15.2 mmol) in acetic acid (45 ml), and the reaction heated at 50° C. for 3 hours. Additional bromine (300 μl, 6.0 mmol) was added dropwise, and the reaction stirred for a further 3 hours at 50° C. The cooled reaction mixture was evaporated under reduced pressure, the residue triturated with water, and the resulting precipitate filtered. The solid was washed with water and diethyl ether, then dried under vacuum, to afford the title compound, (2.05 g, 63%).

δ(DMSOd$_6$): 3.25 (3H, s), 3.70 (2H, t), 4.10 (3H, s), 4.60 (2H, t), 8.78 (1H, d), 9.20 (1H, d), 12.18 (1H, s).

LRMS: m/z 443 (M+18)$^+$

Preparation 118

5-(5-Amino-2-ethoxypyridin-3-yl)-2-methyl-2,6-dihydro7H-pyrazolo[4,3-d]pyrimidin-7-one Iron powder (3.7 g, 66.3 mmol) was added to a solution of the title compound of preparation 113 (2.91 g, 9.2 mmol) in acetic acid (40 ml) and water (4 ml), and the reaction stirred at room temperature for 18 hours. The mixture was filtered through Celite®, the filtrate concentrated under reduced pressure, and the residue partitioned between water and dichloromethane. The resulting precipitate was filtered off, washed well with methanol and dried under vacuum. The filtrate was separated, the organic phase was dried (MgSO$_4$), and evaporated under reduced pressure to give, when combined with the previously isolated solid, the title compound (1.05 g, 40%).

δ(CDCl$_3$): 1.50 (3H, t), 3.57 (2H, br, s), 4.18 (3H, s), 4.58 (2H, q), 7.80 (1H, d), 7.84 (1H, s), 8.16 (1H, d), 11.15 (1H, s).

LRMS: m/z 304 (M+18)$^+$

Preparation 119

5-[5-Amino-2-(2-methoxyethoxy)pyridin-3-yl]-3-bromo-2-methyl-2,6-dihydro-7H-pyrazolo[4,3-d]pyrimidin-7-one Titanium trichloride (35 ml, 15% w/v solution, 33.6 mmol) was added dropwise to a solution of the title compound of preparation 117 (2.04 g, 4.8 mmol) in acetic acid (35 ml), and the reaction stirred at room temperature for an hour. Tlc analysis showed starting material remaining, so additional titanium trichloride (2×5 ml, 35% w/v solution, 10.4 mmol) was added and the reaction stirred for a further 2 hours. The mixture was concentrated under reduced pressure and the residue partitioned between dichloromethane and saturated aqueous sodium bicarbonate solution. The resulting suspension was filtered through Celite®, and the filtrate separated. The aqueous phase was saturated with sodium chloride, and extracted with dichloromethane. The combined organic solutions were washed with brine, dried (MgSO$_4$) and evaporated under reduced pressure to afford the title compound, (1.88 g, 99%).

δ(CDCl$_3$): 3.36 (3H, s), 3.62 (2H, t), 3.90 (2H, s), 3.98 (3H, s), 4.42 (2H, t), 7.60 (1H, s), 7.98 (1H, s), 11.17 (1H, s).

Preparation 120

5-(5-Amino-2-ethoxypyridin-3-yl)-3-ethoxy-2-methyl-2,6-dihydro-7H-pyrazolo[4,3]pyrimidin7-one A mixture of the title compound of preparation 115 (55 mg, 0.15 mmol) and 10% palladium on charcoal (7.5 mg) in ethanol (22 ml) was hydrogenated at 60 psi(414 kPa) and room temperature for 2 hours. The reaction mixture was filtered through Arbocel®, and the filtrate evaporated under reduced pressure. The crude product was purified by column chromatography on silica gel using dichloromethane:methanol (93.4:6.6) as eluant to afford the title compound, (40 mg, 80%).

δ(CDCl₃): 1.50 (6H, m), 3.86 (3H, s), 4.55 (2H, q) 4.87 (2H, q), 7.77 (1H, d), 8.02 (1H, d), 11.00 (1H, s).

LRMS: m/z 331 (M+1)⁺

Preparation 121

5-[2-Ethoxy-5-(4-ethylpiperazin-1-ylsulphonyl)pyridin-3-yl]-2-methyl-2,6-dihydro-7H-pyrazolo[4,3-d]pyrimidin-7-one Sodium nitrite (380 mg, 5.5 mmol) was added to a cooled (−10° C.) solution of the title compound of preparation 118 (1.05 g, 3.7 mmol) in acetic acid (16 ml) and concentrated hydrochloric acid (16 ml), and the solution stirred at 0° C. for 2 hours. The solution was re-cooled to −30° C., liquid sulphur dioxide (11 ml) added, followed by a solution of copper (II) chloride (1.5 g, 11.1 mmol) in water (5 ml). The reaction mixture was stirred at 0° C. for 30 minutes and at room temperature for an additional 2 hours. The reaction was poured onto ice, and this aqueous mixture extracted with dichloromethane. The combined organic extracts were dried (MgSO₄), and evaporated under reduced pressure. A solution of this intermediate sulphonyl chloride in dichloromethane (5 ml) was cooled in ice. N-Ethylpiperazine (0.7 ml, 5.55 mmol) was added and the reaction stirred at room temperature for 20 hours, then evaporated under reduced pressure. The residue was suspended in aqueous saturated sodium bicarbonate solution, and extracted with ethyl acetate. The combined organic extracts were evaporated under reduced pressure to afford the title compound, (530 mg, 32%).

δ(CDCl₃): 1.02 (3H, t), 1.58 (3H, t), 2.40 (2H, q), 2.58 (4H, m), 3.14 (4H, m), 4.19 (3H, s), 4.77 (2H, q), 7.91 (1H, s), 8.62 (1H, d), 9.07 (1H, d), 10.70 (1H, br, s).

LRMS: m/z 448 (M+1)⁺

Preparation 122 3-Bromo-5-[5-(4-ethylpiperazin-1-ylsulphonyl)-2-(2-methoxyethoxy)pyridin-3-yl]-2-methyl-2,6-dihydro-7H-pyrazolo[4,3-d]pyrimidin-7-one Sodium nitrite (462 mg, 6.70 mmol) was added to a cooled (−10° C.) solution of the title compound of preparation 119 (1.89 g, 4.78 mmol) in acetic acid (10 ml) and concentrated hydrochloric acid (10 ml) and the solution allowed to warm to 0° C. over an hour. The solution was re-cooled to −15° C., liquid sulphur dioxide (15 ml) and a solution of copper (II) chloride (1.92 g, 14.3 mmol) in water (3 ml) added, and the reaction then allowed to warm to room temperature over 2 hours. The mixture was extracted with dichloromethane, the combined organic extracts dried (MgSO₄), concentrated under reduced pressure and azeotroped with toluene. The intermediate sulphonyl chloride was dissolved in dichloromethane (20 ml), triethylamine (1.45 g, 14.3 mmol) and N-ethylpiperazine (1.1 g, 9.6 mmol) were added, and the reaction was stirred at room temperature for an hour. The mixture was washed with aqueous sodium bicarbonate solution, and brine, then dried (MgSO₄) and evaporated under reduced pressure. The crude product was purified by column chromatography on silica gel using an elution gradient of dichloromethane:methanol (100:0 to 97:3) to afford the title compound, (1.0 g, 38%).

δ(CDCl₃): 1.02 (3H, t), 2.40 (2H, q), 2.57 (4H, m), 3.17 (4H, m), 3.58 (3H, s), 3.85 (2H, t), 4.17 (3H, s), 4.78 (2H, t), 8.62 (1H, d), 9.03 (1H, d), 10.95 (1H, s).

Preparation 123

5-[2-Ethoxy-5-(4-ethylpiperazin-1-ylsulphonyl)pyridin-3-yl]-2-methyl-3-nitro-2,6-dihydro-7H-pyrazolo[4,3-d]pyrimidin-7-one Ammonium nitrate (115 mg, 1.45 mmol) was added to a solution of the compound of preparation 121 (430 mg, 0.96 mmol) in trifluoroacetic anhydride (20 ml), and the reaction stirred at room temperature for 18 hours. Tlc analysis showed starting material remaining, so additional ammonium nitrate (115 mg, 1.45 mmol) was added, and the reaction stirred for a further 3 hours. The reaction mixture was carefully diluted with water, then basified to pH 8 using sodium carbonate, and extracted with ethyl acetate. The combined organic extracts were dried (MgSO₄), and evaporated under reduced pressure. The residue was re-partitioned between dichloromethane and hydrochloric acid (2N), and the phases separated. The aqueous phase was basified to pH 8 using sodium carbonate, and this aqueous solution re-extracted with dichloromethane. These combined organic extracts were dried (MgSO₄) and evaporated under reduced pressure. The crude product was purified by column chromatography on silica gel using an elution gradient of dichloromethane:methanol (100:0 to 90:10) to afford the title compound, (460 mg, 97%).

δ(CDCl₃): 1.02 (3H, t), 1.60 (3H, t), 2.42 (2H, q), 2.58 (4H, m), 3.19 (4H, m), 4.55 (3H, s), 4.80 (2H, q), 8.74 (1H, d), 9.22 (1H, d), 11.08 (1H, s).

LRMS: m/z 493 (M+1)⁺

Preparation 124

5-[2-Ethoxy-5-nitropyridin-3-yl]-2-methyl-3-(4trifluoromethoxyphenyl)-2,6-dihydro-7H-pyrazolo[4,3-d]pyrimidin-7-one A mixture of the title compound of preparation 116 (250 mg, 0.64 mmol), 4-trifluoromethoxybenzyl boronic acid (157 mg, 0.76 mmol) and potassium carbonate (176 mg, 1.27 mmol) in dioxan (8 ml) and water (2 ml) was de-gassed and placed under an atmosphere of nitrogen. Tetrakis (triphenylphosphine)palladium (0) (75 mg, 0.065 mmol) was added, and the reaction heated under reflux for 3 hours. The cooled mixture was partitioned between water and dichloromethane and the phases separated. The aqueous layer was extracted with dichloromethane (2×), and the combined organic solutions washed with brine, dried (MgSO₄), and evaporated under reduced pressure. The residue was purified by medium pressure column chromatography on silica gel using an elution gradient of dichloromethane:methanol (99.8:0.2 to 99.4:0.6) to afford the title compound, (168 mg, 55%) as a yellow solid.

δ(CDCl₃): 1.61 (3H, t), 4.20 (3H, s), 4.81 (2H, q), 7.48 (2H, d), 7.75 (2H, d), 9.16 (1H, d), 9.42 (1H, d), 10.72 (1H, s).

LRMS: m/z 499 (M+23)⁺

Preparations 125 to 133

The compounds of the general structure:

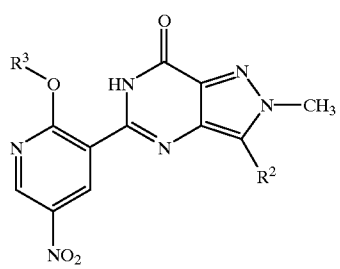

were prepared from the corresponding bromides and boronic acids, following a similar procedure to that described in preparation 124.

| Prep. | R³ | R² | Data |
|---|---|---|---|
| 125 | CH₂CH₃ | 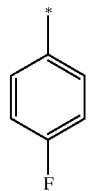 | δ (CDCl₃) : 1.61 (3H, t), 4.19 (3H, s), 4.80 (2H, q), 7.34 (2H, m), 7.65 (2H, m), 9.15 (1H, d), 9.42 (1H, d), 10.71 (1H, s).<br>LRMS : m/z 411 (M + 1)⁺ |
| 126¹ | CH₂CH₃ | 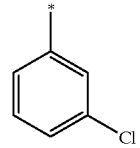 | δ (CDCl₃) : 1.60 (3H, t), 4.21 (3H, s), 4.82 (2H, q), 7.58 (3H, m), 7.70 (1H, m), 9.18 (1H, d), 9.44 (1H, d), 10.73 (1H, br, s). |
| 127 | (CH₂)₂OCH₃ | 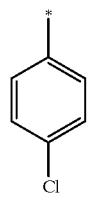 | δ (CDCl₃) : 3.58 (3H, s), 3.90 (2H, t), 4.19 (3H, s), 4.82 (2H, t), 7.60 (4H, m), 9.14 (1H, d), 9.38 (1H, d), 10.91 (1H, s). |
| 128² | CH₂CH₃ | 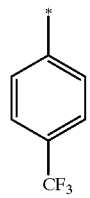 | δ (CDCl₃) : 1.61 (3H, t), 4.22 (3H, s), 4.82 (2H, q), 7.82 (2H, d), 7.90 (2H, d), 9.17 (1H, d), 9.42 (1H, d), 10.76 (1H, s).<br>LRMS : m/z 461 (M + 1)⁺ |
| 129¹ | CH₂CH₃ | 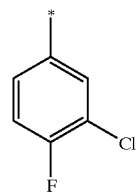 | δ (CDCl₃) : 1.55 (3H, t), 4.15 (3H, s), 4.72 (2H, q), 7.36 (1H, m), 7.50 (1H, m), 7.70 (1H, m), 9.08 (1H, d), 9.26 (1H, d), 10.89 (1H, s).<br>LRMS : m/z 467 (M + 23)⁺ |
| 130¹ | CH₂CH₃ | 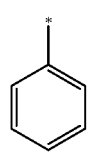 | δ (CDCl₃) : 1.60 (3H, t), 4.20 (3H, s), 4.80 (2H, q), 7.57 (1H, m), 7.61 (2H, m), 7.66 (2H, m), 9.14 (1H, d), 9.43 (1H, d), 10.70 (1H, s).<br>LRMS : m/z 410 (M + 18)⁺ |
| 131 | (CH₂)₂OCH₃ | 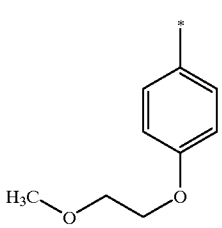 | δ (CDCl₃) : 3.48 (3H, s), 3.58 (3H, s), 3.80 (2H, t), 3.89 (2H, t), 4.18 (3H, s), 4.22 (2H, t), 4.82 (2H, t), 7.17 (2H, d), 7.60 (2H, d), 9.12 (1H, d), 9.39 (1H, d), 10.83 (1H, s). |

-continued

| Prep. | R³ | R² | Data |
|---|---|---|---|
| 132 | CH₂CH₃ | * (1,3-benzodioxol-5-yl) | δ (CDCl₃) : 1.60 (3H, t), 4.18 (3H, s), 4.80 (2H, q), 6.12 (2H, s), 7.02 (1H, m), 7.12 (2H, m), 9.15 (1H, d), 9.42 (1H, d), 10.68 (1H, s). LRMS : m/z 459 (M + 23)⁺ |

¹=purified by column chromatography on silica gel using dichloromethane:methanol as eluent.
²=purified by trituration/filtration from diethyl ether Preparation 133
5-[5-Amino-2-ethoxypyridin-3-yl]-3-(4-fluorophenyl)-2-methyl-2,6-dihydro-7H-pyrazolo[4,3-d]pyrimidin-7-one 10% Palladium on charcoal (20 mg) was added to a solution of the tide compound of preparation 125 (86 mg, 0.21 mmol) in ethanol (50 ml) and water (1 ml), and the mixture hydrogenated at 60 psi (414 kPa) and 50° C. for 3 hours. The reaction mixture was filtered through Arbocel®, the filtrate evaporated under reduced pressure, and azeotroped with dichloromethane. The residue was triturated with diethyl ether, filtered and dried to afford the title compound, (63 mg, 79%).

δ(CDCl₃): 1.40 (3H, t), 3.75 (2H, br, s), 4.06 (3H, s), 4.45 (2H, q), 7.19 (2H, m), 7.58 (2H, m), 7.64 (1H, d), 7.99 (1H, d), 11.14 (1H, s).
LRMS: m/z 381 (M+1)⁺

Preparation 134
5-[5-Amino-2-ethoxypyridin-3-yl]-2-methyl-3-(4trifluoromethylphenyl)-2,6-dihydro-7H-pyrazolo[4,3-d]pyrimidin-7-one The title compound was prepared from the title compound of preparation 128, following the procedure described in preparation 133. The crude product was purified by column chromatography on silica gel using an elution gradient of dichloromethane:methanol (98:2 to 95:5) to afford the desired product (90 mg, 44%).

δ(CDCl₃): 1.56 (3H, t), 3.58 (2H, br, s), 4.21 (3H, s), 4.59 (2H, q), 7.79 (1H, d), 7.83 (4H, m), 8.12 (1H, d), 11.28 (1H, s).
LRMS: m/z 432 (M+2)⁺

Preparation 135
5-[5-Amino-2-ethoxypyridin-3-yl]-2-methyl-3-phenyl-2,6-dihydro-7H-pyrazolo[4,3-d]pyrimidin-7-one The title compound was obtained as a solid (75%) from the title compound of preparation 130, following a similar procedure to that described in preparation 133.

δ(CDCl₃): 1.54 (3H, t), 3.56 (2H, br, s), 4.18 (3H, s), 4.58 (2H, q), 7.53 (1H, m), 7.60 (2H, m), 7.67 (2H, m), 7.77 (1H, d), 8.15 (1H, d), 11.22 (1H, s).
LRMS: m/z 363 (M+1)⁺

Preparation 136
5-[5-Amino-2-ethoxypyridin-3-yl]-3-(3-chlorophenyl)-2-methyl-2,6-dihydro-7H-pyrazolo[4,3-d]pyrimidin-7-one Acetic acid (5 ml) was added to a mixture of the title compound of preparation 126 (250 mg, 0.59 mmol) and iron powder (328 mg, 5.86 mmol) in water (300 μl) and the reaction stirred at room temperature for 2 hours. The reaction mixture was filtered through Celite®, and the filtrate evaporated under reduced pressure. The crude product was purified by column chromatography on silica gel using dichloromethane:methanol (95:5) as eluant to afford the title compound, (203 mg, 87%) as a brown solid.

δ(CDCl₃): 1.56 (3H, t), 4.20 (3H, s), 4.60 (2H, q), 7.55 (3H, m), 7.74 (2H, m), 8.14 (1H, m), 11.38 (1H, s).
LRMS: m/z 397 (M+1)⁺

Preparation 137
5-[5-Amino-2-ethoxypyridin-3-yl]-3-(3-chloro4-fluorophenyl)-2-methyl2,6-dihydro-7H-pyrazolo[4,3-d]pyrimidin-7-one A suspension of the title compound of preparation 129 (125 mg, 0.28 mmol) in ethanol (4 ml) was added to a mixture of iron powder (47 mg, 0.84 mmol) and ammonium chloride (75 mg, 1.40 mmol) in water (1.5 ml), and the reaction heated under reflux for 4 hours. The hot solution was filtered through Arbocel®, and washed through well with hot ethanol. The filtrate was evaporated under reduced pressure to give the title compound as a yellow solid (35 mg, 30%). The Arbocel® filter pad was suspended in a solution of dichloromethane:ethanol (1:1), the mixture stirred for a minute, and the supernatant decanted off. This was repeated several times and the combined solutions filtered, and the filtrate evaporated under reduced pressure to afford an additional (46.4 mg, 40%) of the title compound.

δ(CDCl₃): 1.56 (3H, m), 3.57 (2H, br, s), 4.18 (3H, s), 4.58 (2H, q), 7.38 (1H, m), 7.57 (1H, m), 7.78 (2H, m), 8.12 (1H, d), 11.27 (1H, s).
LRMS: m/z 415 (M+1)⁺

Preparation 138
5-[5-Amino-2-ethoxypyridin-3-yl]-2-methyl-3-(4-trifluoromethoxyphenyl)-2,6-dihydro-7H-pyrazolo[4,3-d]pyrimidin-7-one The title compound was obtained as a yellow solid (86%) from the tide compound of preparation 124, following a similar procedure to that described in preparation 137.

δ(CDCl₃): 1.54 (3H, t), 3.59 (2H, br, s), 4.19 (3H, s), 4.58 (2H, q), 7.42 (2H, d), 7.74 (2H, d), 7.79 (1H, d), 8.14 (1H, d), 11.25 (1H, d).
LRMS: m/z 469 (M+23)⁺

Preparation 139
5-[5-Amino-2-ethoxypyridin-3-yl]-3-(1,3-benzodioxol-5-yl)-2-methyl-2,6-dihydro-7H-pyrazolo[4,3-d]pyrimidin-7-one The title compound was obtained as a yellow solid (65%) from the title compound of preparation 132, following a similar procedure to that described in preparation 138.

δ(CDCl₃): 1.55 (3H, m), 3.55 (2H, s), 4.16 (3H, s), 4.58 (2H, q), 6.09 (2H, s), 7.01 (1H, d), 7.14 (2H, m), 7.78 (1H, m), 8.16 (1H, m), 11.20 (1H, s).
LRMS: m/z 407 (M+1)⁺

Preparation 140
5-[5-Amino-2-ethoxypyridin-3-yl]-3-[4(2-methoxyethoxy)phenyl]-2-methyl-2,6-dihydro-7H-pyrazolo[4,3-d]pyrimidin-7-one Titanium trichloride (2.9 ml, 15% w/v aqueous solution, 3.0 mmol) was added to a solution of the title compound of preparation 131 (200 mg, 0.40 mmol) in acetic acid (4 ml) and the reaction stirred at room temperature for an hour. Tlc analysis showed starting material remaining, additional titanium trichloride (1 ml, 15% w/v aqueous solution, 0.97 mmol) was added and the reaction stirred for a further 30 minutes. The reaction mixture was concentrated under reduced pressure and the residue partitioned between dichloromethane and saturated aqueous sodium bicarbonate solution. The phases were separated and the aqueous layer filtered to remove titanium residues and this filtrate extracted with dichloromethane (2×). The combined organic solutions were washed with brine, dried (MgSO$_4$), and evaporated under reduced pressure to afford the title compound (87 mg, 46%). The filtered titanium residues were triturated with a dichloromethane:methanol (95:5) solution, this solution decanted off and evaporated under reduced pressure to provide an additional (57 mg, 30%) of the title compound.

δ(CDCl$_3$): 3.49 (3H, s), 3.55 (5H, s), 3.80 (4H, m), 4.16 (3H, s), 4.22 (2H, t), 4.61 (2H, t), 7.14 (2H, d), 7.59 (2H, d), 7.75 (1H, d), 8.05 (1H, d), 11.23 (1H, s).

LRMS: m/z 467 (M+1)$^+$

Preparation 141

5-[5-Amino-2-ethoxypyridin-3-yl]-3-(4-chlorophenyl)-2-methyl-2,6-dihydro-7H-pyrazolo[4,3-d]pyrimidin-7-one The title compound was obtained (60%) from the title compound of preparation 127, following a similar procedure to that described in preparation 140.

δ(CDCl$_3$): 3.57 (3H, s), 3.82 (2H, t), 4.18 (3H, s), 4.61 (2H, t), 7.58 (2H, d), 7.62 (2H, d), 7.77 (1H, d), 8.04 (1H, d), 11.30 (1H, s).

LRMS: m/z 427(M+1)$^+$

Preparation 142

1-Iodo-4-(2-methoxyethoxy)benzene

Triphenylphosphine (2.8 g, 10.7 mmol) was added to an ice-cold solution of 4-iodophenol (2.2 g, 10.0 mmol) and 2-methoxyethanol (0.79 ml, 10.0 mmol) in tetrahydrofuran (10 ml). A solution of diethyl azodicarboxylate (1.88 ml, 11.5 mmol) in tetrahydrofuran (10 ml) was then added dropwise, and the reaction stirred at room temperature for 18 hours. The mixture was evaporated under reduced pressure, the residue partitioned between dichloromethane and hydrochloric acid (2N) and the phases separated. The organic layer was washed with brine, dried (MgSO$_4$) and evaporated under reduced pressure. The residue was triturated with diethyl ether, the resulting suspension filtered and the filtrate concentrated under reduced pressure. The crude product was purified by column chromatography on silica gel using pentane:dichloromethane (75:25) as eluant to give the title compound, (2.0 g, 71%) as an oil.

δ(CDCl$_3$): 3.42 (3H, s), 3.75 (2H, t), 4.08 (2H, t), 6.70 (2H, d), 7.56 (2H, d).

Preparation 143

2-Amino-5-iodopyridine

A mixture of 2-aminopyridine (7.0 g, 74.4 mmol), periodic acid (14.9 mmol), iodine (7.59 g, 30.0 mmol) and concentrated sulphuric acid (1.4 ml) in water (9 ml) and acetic acid (45 ml) was heated at 80° C. for 4 hours, and at room temperature for a further 18 hours. The reaction was poured into 10% aqueous sodium thiosulphate solution (200 ml), and the mixture extracted with diethyl ether. The combined organic extracts were washed with aqueous sodium hydroxide solution (2N), brine, then dried (K$_2$CO$_3$) and evaporated under reduced pressure. The crude product was purified by medium pressure column chromatography on silica gel using an elution gradient of pentane:ethyl acetate (84:16 to 75:25) to give the title compound.

δ(DMSOd$_6$): 6.78 (1H, d), 8.02 (1H, d), 8.20 (1H, s).

Preparation 144

2-(Azetidin-1-yl)-5-bromopyridine hydrochloride

Azetidine hydrochloride (3.0 g, 32.1 mmol) was added to a solution of sodium (0.73 g, 31.7 mmol) in ethanol (25 ml) and the solution stirred vigorously for an hour. 2,5-Dibromopyridine (5.0 g, 21.1 mmol) was then added and the reaction mixture heated at 100° C. for 10 hours in a sealed vessel, and then at 120° C. for a further 10 hours. The cooled mixture was concentrated under reduced pressure and the residue was partitioned between water and ethyl acetate. The layers were separated, the aqueous phase was extracted with ethyl acetate (3×), and the combined organic extracts washed with brine, dried (MgSO$_4$), and evaporated under reduced pressure. The crude product was purified by medium pressure column chromatography on silica gel, using dichloromethane:pentane (66:34) as eluant to give the tile compound, (900 mg, 17%) as white crystals.

δ(CDCl$_3$): 2.39 (2H, m), 4.00 (4H, m), 6.17 (1H, d), 7.48 (1H, dd), 8.16 (1H, d).

LRMS: m/z 213, 215 (M+1)$^+$

Preparation 145

4-Bromo-1-ethylpyrazole

A mixture of 4-bromopyrazole (4.25 g, 28.9 mmol), cesium carbonate (18.8 g, 57.8 mmol) and ethyl bromide (3.24 ml, 43.3 mmol) in acetonitrile (40 ml) was stirred at room temperature under a nitrogen atmosphere for 72 hours. The reaction mixture was concentrated under reduced pressure at room temperature, and the residue triturated with diethyl ether. The suspension was filtered, the solid washed well with diethyl ether, and the combined filtrates evaporated under reduced pressure at room temperature, to afford the title compound (3.2 g, 63%).

δ(CDCl$_3$): 1.43 (3H, t), 4.15 (2H, q), 7.39 (1H, s), 7.42 (1H, s).

LRMS: m/z 175, 177 (M+1)$^+$

Preparation 146

4-(2-Methoxyethoxy)phenyl boronic acid n-Butyllithium (5.17 ml, 1.6M in hexanes, 8.27 mmol) was added dropwise to a cooled (−78° C.) solution of the title compound from preparation 142 (2.0 g, 7.19 mmol) in tetrahydrofuran (10 ml), and the solution stirred for minutes. Triisopropyl borate (2.4 ml, 10.4 mmol) was added dropwise and the reaction allowed to warm to room temperature over 3 hours. Hydrochloric acid (2N) was added and the mixture extracted with diethyl ether (4×). The combined organic extracts were washed with brine, dried (MgSO$_4$) and evaporated under reduced pressure. The residue was triturated with diethyl ether:pentane (1:1), the resulting solid filtered off and the filtrate evaporated under reduced pressure. The isolated solid was redissolved in diethyl ether, treated with charcoal, this suspension filtered and the filtrate evaporated under reduced pressure to give the title compound, (256 mg, 18%) as a yellow solid. The remaining crude product was purified by column chromatography on silica gel using pentane:diethyl ether (50:50) as eluant to afford additional title compound, (150 mg, 10%).

δ(DMSOd$_6$): 3.27 (3H, s), 3.62 (2H, t), 4.08 (2H, t), 6.85 (2H, d), 7.70 (2H, d).

Preparation 147

6-(Methylamino)pyridin-3-yl boronic acid hydrochloride n-Butyllithium (10.8 ml, 1.6M in hexanes, 17.3 mmol) was added dropwise to a cooled (−70° C.) solution of 5-bromo-2-methylaminopyridine (J. Org. Chem. 1983; 48; 1064) (1.5 g, 8.02 mmol) in tetrahydrofuran (20 ml), and the solution stirred for 30 minutes. A solution of triisopropyl borate (2.77 ml, 12.0 mmol) in tetrahydrofuran (4 ml) was added dropwise, and the reaction then allowed to warm to room temperature over 2 hours. Additional triisopropyl borate (1.85 ml, 8.02 mmol) was added and the mixture stirred for a further hour. The reaction was quenched by the addition of hydrochloric acid (2N), and the mixture then evaporated under reduced pressure. The residue was suspended in water, washed with diethyl ether, and the aqueous solution evaporated under reduced pressure. The residue was purified by reverse phase column chromatography on polystyrene gel, using an elution gradient of water:methanol (100:0 to 80:20) to give the title compound, (140 mg, 9%) as a white solid.

δ(DMSOd₆): 2.95 (3H, d), 7.00 (1H, d), 8.03 (1H, d), 8.21 (1H, s), 8.41 (2H, s).
LRMS: m/z 152 (M+1)⁺

Preparation 148

6-(Dimethylamino)pyridin-3-yl boronic acid dihydrochloride n-Butyllithium (5.3 ml, 1.6M in hexanes, 8.5 mmol) was added dropwise to a cooled (−70° C.) solution of 5-bromo-2-(dimethylaminopyridine (J. Org. Chem. 1983; 48; 1064) (1.5 g, 7.46 mmol) in tetrahydrofuran (20 ml), and the solution stirred for 30 minutes. A solution of triisopropyl borate (2.57 ml, 11.2 mmol) in tetrahydrofuran (4 ml) was added dropwise, and the reaction then allowed to warm to room temperature over 3 hours. The reaction was quenched by the addition of hydrochloric acid (2N), and the mixture then evaporated under reduced pressure. The residue was crystallised from methanol:diethyl ether to afford the title compound, (800 mg, 45%) as an off-white solid.
δ(DMSOd₆): 3.20 (6H, s), 7.18 (1H, d), 8.18 (2H, m).

Preparation 149

5-Methyl-2-(tri-n-butylstannyl)pyridine n-Butyllithium (12.8 ml, 2.5M in hexanes, 32.6 mmol) was added dropwise to a cooled (−78° C.) solution of 2-bromo5-methylpyridine (5.0 g, 29.1 mmol), and the solution stirred for an hour. Tri-n-butyltin chloride (9.5 ml, 34.9 mmol) was then added and the reaction allowed to warm to room temperature, and stirred for 18 hours. The reaction mixture was evaporated under reduced pressure and the residue purified by column chromatography on silica gel using an elution gradient of pentane:ethyl acetate (100:0 to 90:10) to give the title compound, (6.5 g, 58%) as a yellow oil.
δ(CDCl₃): 0.78–1.68 (m, 27H), 2.25 (3H, s), 7.24 (2H, m), 8.58 (1H, m).

Preparation 150

2-Ethyl-5-(tri-n-butylstannyl)pyridine n-Butyllithium (2 ml, 1.6M in hexanes, 3.22 mmol) was added dropwise to an ice-cooled solution of diisopropylamine (0.45 ml, 3.22 mmol) in tetrahydrofuran (6 ml) under a nitrogen atmosphere, and the solution stirred for an hour. Tri-n-butyltin hydride (0.79 ml, 2.96 mmol) was added and the solution stirred for a further 2 hours, and then cooled to −78° C. A solution of 5-bromo-2-ethylpyridine (WO 97/01552) (500 mg, 2.69 mmol) in tetrahydrofuran (4 ml) was then added dropwise, and once addition was complete, the reaction was allowed to warm to room temperature, and stirred for 18 hours. The reaction mixture was concentrated under reduced pressure and the residue partitioned between dichloromethane and aqueous ammonium chloride solution. The layers were separated, the organic phase dried (MgSO₄) and evaporated under reduced pressure. The crude product was purified by column chromatography on silica gel using an elution gradient of pentane:ethyl acetate (100:0 to 90:10) to afford the tide compound, (210 mg, 19%) as a yellow oil.
LRMS: m/z 397 (M+1)⁺

Preparation 151

2-(Tri-n-butylstannyl)pyrazine n-Butyllithium (30.0 ml, 1.6M in hexanes, 48.0 mmol) was added dropwise to a cooled (−40° C.) solution of diisopropylamine (7 ml, 50.1 mmol) in tetrahydrofuran (30 ml), so as to maintain the temperature below −30° C. Once addition was complete, the solution was allowed to warm to room temperature for 2 minutes, then re-cooled to −70° C. Tri-n-butyltin hydride (12 ml, 45.8 mmol) was added dropwise over 10 minutes, and once addition was complete, the reaction was stirred at −60° C. for 2 hours. A solution of 2-chloropyrazine (5.0 g, 43.7 mmol) in tetrahydrofuran (5 ml) was added, and the reaction allowed to warm to room temperature. Aqueous ammonium chloride solution was added to quench the reaction, followed by dilution with ethyl acetate. The resulting suspension was filtered through Celite®, and the filtrate separated. The organic phase was washed with brine, dried (MgSO₄), and evaporated under reduced pressure. The residual oil was purified by column chromatography on silica gel using an elution gradient of pentane:ethyl acetate (100:0 to 90:10) to afford the title compound, (800 mg, 5%) as a yellow oil.
δ(CDCl₃): 0.88 (3H, t), 1.18 (6H, m), 1.22–1.40 (6H, m), 1.58 (6H, m), 8.38 (1H, d), 8.55 (1H, d), 8.70 (1H, s).

Preparation 152

2-Chloro-5-(tri-n-butylstannyl)pyrinidine n-Butyllithium (31.0 ml, 1.6M in hexanes, 49.0 mmol) was added dropwise to a cooled (−78° C.) solution of diisopropylamine (6.9 ml, 49.0 mmol) in tetrahydrofuran (35 ml), and the resulting solution stirred for 30 minutes. Tri-n-butyltin hydride (13.4 ml, 49.0 mmol) was then added, and the reaction stirred for 2 hours at −78° C. A solution of 5-bromo-2-chloropyrimidine (J. Chem. Soc. Chem. Comm. 1996; 2719), (8.0 g, 41.0 mmol) in tetrahydrofuiran (10 ml) was added, and the reaction allowed to warm to room temperatures and stirred for 14 hours. The reaction mixture was concentrated under reduced pressure, and the residue triturated with a solution of ethyl acetate:hexane (50:50). The resulting suspension was filtered through silica gel and the filtrate concentrated under reduced pressure. The crude product was purified by column chromatography on silica gel using an elution gradient of pentane:ethyl acetate (100:0 to 95:5) to afford the title compound, (1.1 g, 5.5%) as a yellow oil.
δ(CDCl₃): 0.89 (9H, m), 1.15 (6H, m), 1.34 (6H, m), 1.52 (6H, m), 8.56 (2H; s).
LRMS: m/z 402, 404 (M+1)⁺

Preparation 153

5-(Tri-n-butylstannyl)-2-pyrimidinylamine

A solution of the title compound from preparation 152 (435 mg, 1.08 mmol) in saturated methanolic ammonia (10 ml) was heated at 50° C. for 48 hours in a sealed vessel. The reaction was concentrated under reduced pressure, re-suspended in dichloromethane and the resulting precipitate filtered off, and the filtrate concentrated under reduced pressure. The crude product was purified by column chromatography on silica gel using pentane:ethyl acetate (97:3) as eluant to afford the tide compound, (182 mg, 44%) as a yellow solid.
δ(CDCl₃): 0.80–1.72 (27H, m), 5.04 (2H, s), 8.24 (2H, m).
LRMS: m/z 386 (M+1)⁺

Preparation 154

6(Trimethylstannyl)imidazo[1,2α]pyridine

A solution of 6bromo-imidazo[1,2-a]pyridine (Chem. Pharm. Bull. 39; 6; 1991; 1556) (500 mg, 2.55 mmol) and hexamethylditin (919 mg, 2.81 mmol) in dioxan (8 ml) was de-gassed and placed under an atmosphere of nitrogen. Tetrakis(triphenylphosphine)palladium (0) (147 mg, 0.13 mmol) was added, and the reaction heated under reflux for 5 hours. The cooled mixture was partitioned between 10% aqueous potassium fluoride solution and ethyl acetate and the layers separated. The organic phase was dried (MgSO₄) and evaporated under reduced pressure. The crude product was purified by column chromatography on silica gel using dichloromethane:methanol (90:10) as eluant to afford the title compound, (620 mg, 87%) as an oil.
δ(CDCl₃): 0.32 (9H, s), 7.18 (1H, d), 7.48–7.62 (3H, m), 8.07 (1H, s).
LRMS: m/z 281 (M+1)⁺

Preparation 155

1-Ethyl-4-(tri-n-butylstannyl)pyrazole t-Butyllithium (14.0 ml, 1.7M in pentane, 23.8 mmol) was added dropwise to a cooled (−78° C.) solution of the title compound of preparation 145 (2.0 g, 11.4 mmol) in tetrahydrofuran (30 ml) and diethyl ether (30 ml), under a nitrogen atmosphere. The solution was stirred for 90 minutes, then tri-n-butyltin chloride (3.7 ml, 13.7 mmol) was added, and the reaction allowed to warm to room temperature, and stirred for 18 hours. The reaction mixture was concentrated under reduced pressure and the residue partitioned between water and dichloromethane. The layers were separated, and the organic phase dried ($MgSO_4$) and evaporated under reduced pressure. The crude product was purified by column chromatography on silica gel using an elution gradient of pentane:ethyl acetate (100:0 to 90:10) to afford the title compound (1.7 g, 39%).

δ($CDCl_3$): 0.88 (9H, t), 0.99 (6H, t), 1.32 (6H, m), 1.50 (9H, m), 4.19 (2H, q), 7.24 (1H, s), 7.41 (1H, s).

LRMS: m/z 387 $(M+2)^+$

Preparation 156

4-[2-Ethoxy-5-(4-ethylpiperazin-1-ylsulphonyl)pyridin-3-ylcarboxamido]-3-methoxycarbonyl-2-methyl-pyrazole-5-carboxamide The title compound of preparation 52 (9.0 g, 45.0 mmol) was added to a suspension of the title compound of preparation 69 (19.9 g, 50.0 mmol) in dichloromethane (200 ml), and the mixture cooled in an ice-bath. Triethylamine (21 ml, 150.0 mmol) was added dropwise over 30 minutes, and once addition was complete, the reaction was stirred at room temperature for 20 hours. The reaction mixture was washed with aqueous saturated sodium bicarbonate solution, and water, then dried ($Na_2SO_4$) and evaporated under reduced pressure. The residual solid was triturated with ethanol, filtered and dried to afford the title compound (16.0 g, 68%).

δ($CDCl_3$): 1.01 (3H, t), 1.60 (3H, t), 2.40 (2H, q), 2.52 (4H, m), 3.08 (4H, m), 3.92 (3H, s), 4.08 (3H, s), 4.80 (2H, q), 5.38 (1H, s), 6.67 (1H, s), 8.65 (1H, d), 8.82 (1H, d), 11.01 (1H, s).

LRMS: m/z 525 $(M+2)^+$

Preparation 157

5-[2-Ethoxy-5-(4-ethylpiperazin-1-ylsulphonyl)pyridin-3-yl]-2-methyl-7-oxo-2,6-dihydro-[4,3-d]pyrimidine-3-carboxylic acid A mixture of the title compound from preparation 156 (16.0 g, 30.4 mmol) and potassium bis(trimethylsilyl)amide (25.0 g, 125.2 mmol) in ethanol (900 ml) was heated at 110° C. in a sealed vessel for 18 hours. The cooled mixture was diluted with sufficient water to obtain a solution, then acidified to pH 3 using hydrochloric acid. The resulting precipitate was filtered slowly, and dried. The solid was suspended in water (200 ml), and basified to pH 12 using 0.88 ammonia solution. The mixture was heated to reflux, then cooled in ice and the resulting precipitate filtered and dried to afford the title compound (10.1 g, 68%).

δ($DMSOd_6$): 0.96 (3H, t), 1.35 (3H, t), 2.40 (2H, q), 2.50 (4H, m), 2.99 (4H, m), 4.30 (3H, s), 4.48 (2H, q), 8.24 (1H, s), 8.63 (1H, s), 12.11 (1H, br, s).

LRMS: m/z 492 $(M+1)^+$

Preparation 158

5-[2-Ethoxy-5-(4-ethylpiperazin-1-ylsulphonyl)pyridin-3-yl]-2-methyl-7-oxo-2,6-dihydro-[4,3-d]pyrimidine-3-carboxylic acid hydrochloride Oxalyl chloride (230 μl, 2.6 mmol) was added to a suspension of the title compound of preparation 157 (500 mg, 1.02 mmol) and N,N-dimethylformamide (20 μl) in dichloromethane (40 ml) and the reaction stirred at room temperature for 2½ hours. The reaction mixture was evaporated under reduced pressure, azeotroped with toluene and dried under vacuum to afford the title compound, (450 mg), as a pale yellow solid.

δ($DMSOd_6$): 1.20 (3H, t), 1.35 (3H, t), 2.94 (2H, m), 3.10 (4H, m), 3.52 (2H, m), 3.82 (2H, m), 4.35 (3H, s), 4.52 (2H, q), 8.38 (1H, s), 8.78 (1H, s), 11.00 (1H, s).

Preparation 159

3-Amino-5-[2-ethoxy-5-(4-ethylpiperazin-1-ylsulphonyl)pyridin-3-yl]-2-methyl-2,6-dihydro-7H-pyrazolo[4,3-d]pyrimidin-7-one A mixture of the title compound of preparation 123 (55 mg, 0.11 mmol) and 10% palladium on charcoal (6 mg) in ethanol (5 ml), was hydrogenated at 50 psi (345 kPa) and room temperature for 4 hours. The mixture was filtered through Arbocel®, and the filtrate evaporated under reduced pressure. The crude product was purified by column chromatography on silica gel using an elution gradient of dichloromethane:methanol (100:0 to 90:10) to afford the title compound, (28 mg, 55%).

δ($CDCl_3$): 1.02 (3H, t), 1.58 (3H, t), 2.41 (2H, q), 2.57 (4H, m), 3.13 (4H, m), 3.95 (3H, s), 4.21 (2H, s), 4.75 (2H, q), 8.60 (1H, d), 9.00 (1H, d), 10.60 (1H, s).

LRMS: m/z 463 $(M+1)^+$

Synthesis of the Compounds of Formulae IA and IB

EXAMPLE 1

5-[5-(4-Methylpiperazin-1-ylsulphonyl)-2-n-propoxyphenyl]-7-oxo-1(pyridin-2-yl)methyl-1,6-dihydro-1H-pyrazolo[4,3-d]pyrimidine-3-carboxamide Thionyl chloride (64 μl, 0.87 mmol) and chlorosulphonic acid (387 μl, 5.82 mmol) were added to an ice cooled flask containing the title compound of Preparation 26 (235 mg, 0.58 mmol), and the reaction stirred at room temperature for 18 hours. Ice (1 g) was carefully added with stirring, then N-methylpiperazine (2 ml, 18.0 mmol) followed by sufficient ethanol to obtain a solution. The mixture was stirred for 3 hours at room temperature and evaporated under reduced pressure. The residue was partitioned between dichloromethane (5 mi) and saturated sodium bicarbonate solution (10 ml), and the phases separated. The aqueous layer was extracted with dichloromethane (3×10 ml), the combined organic solutions dried ($Na_2SO_4$) and evaporated under reduced pressure. The residual yellow oil was purified by column chromatography on silica gel, using an elution gradient of dichloromethane:methanol (100:0 to 97:3) to afford the title compound (160 mg, 50%) as a pale yellow solid.

δ($DMSOd_6$): 0.92 (3H, t), 1.72 (2H, m), 2.15 (3H, s), 2.37 (4H, m), 2.92 (4H, m), 4.14 (2H, t), 5.96 (2H, s), 7.23 (1H, d), 7.31 (1H, m), 7.40 (1H, d), 7.70 (1H, s), 7.79 (2H, m), 7.85 (1H, d), 7.93 (1H, s), 8.48 (1H, d), 12.55 (1H, s).

LRMS: m/z 567 $(M+1)^+$

EXAMPLE 2

5-[5-(4-Methylpiperazin-1-ylsulphonyl)-2-n-propoxphenyl]-7-oxo-1(pyridin-2-yl)methyl-1,6-dihydro-1H-pyrazolo[4,3-d]pyrimidine-3-N-methylcarboxamide Thionyl chloride (26 μl, 0.36 mmol) and chlorosulphonic acid (160 μl, 2.39 mmol) were added to an ice cooled flask containing the title compound of Preparation 33 (100 mg, 0.24 mmol) and the reaction stirred at room temperature for 18 hours. Ice (1 g) was carefully added, then N-methylpiperazine (3 ml, 27.0 mmol) followed by enough ethanol to ensure solution, and the mixture stirred at room temperature for 4 hours. The reaction mixture was concentrated under reduced pressure, the residue partitioned between dichloromethane (5 ml) and saturated sodium bicarbonate solution (10 ml), and the phases separated. The aqueous layer was extracted with dichloromethane (3×10 ml), the combined organic solutions washed with water (10 ml), dried (Na$_2$SO$_4$) and evaporated under reduced pressure. The residue was triturated with diethyl ether, to afford the title compound (95 mg, 68%) as a white solid.

Found: C, 55.05; H, 5.51; N, 18.77. C$_{27}$H$_{32}$N$_8$O$_5$S;0.50H$_2$O requires C, 55.00; H, 5.64; N, 19.00%.

δ(CDCl$_3$): 1.18 (31H, t), 2.04 (21H, m), 2.29 (3H, s), 2.52 (41H, m), 3.12 (7H, m), 4.30 (2H, t), 6.04 (21H, s), 7.08–7.23 (3H, m), 7.61 (1H, m), 7.90 (1H, d), 8.10 (1H, m), 8.53 (1H, d), 8.75 (1H, s), 11.00 (1H, s).

LRMS: m/z 581 (M+1)$^+$

EXAMPLES 3 to 14

The compounds of the following tabulated examples of the general formula:

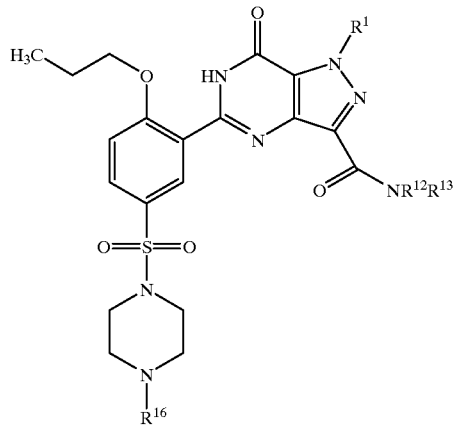

were prepared by the reaction of the corresponding pyrazolo[4,3-d]pyrimidinone with N-alkyl piperazine using similar methods to those described in either Example 1 (method a) or 2 (method b).

| Example | R$^1$ | R$^{16}$ | NR$^{12}$R$^{13}$ | Data | Method |
|---|---|---|---|---|---|
| 3 | *-CH$_2$-(2-pyridyl) | CH$_2$CH$_3$ | NH$_2$ | Found: C, 54.96; H, 5.60; N, 18.49. C$_{27}$H$_{32}$N$_8$O$_5$S;0.50H$_2$O requires C, 55.00; H, 5.64; N, 19.00%. δ (CDCl$_3$) : 1.03 (3H, t), 1.19 (3H, t), 2.05 (2H, m), 2.42 (2H, q), 2.55 (4H, m), 3.12 (4H, m), 4.28 (2H, t), 5.94 (1H, s), 6.04 (2H, s) 7.19 (1H, d), 7.96 (1H, s), 8.54 (1H, d), 7.96 (1H, s), 11.10 (1H, s). LRMS : m/z 581 (M + 1)$^+$ | a |
| 4 | *-CH$_2$-(2-pyridyl) | CH$_2$CH$_3$ | NHCH$_3$ | Found: C, 55.63; H, 5.64; N, 18.47. C$_{28}$H$_{34}$N$_8$O$_5$S;0.50H$_2$O requires C, 55.70; H, 5.84; N, 18.56%. δ (CDCl$_3$) : 1.04 (3H, t), 1.18 (3H, t), 2.04 (2H, m), 2.42 (2H, q), 2.55 (4H, m), 3.12 (7H, m), 4.29 (2H, t), 6.04 (2H, s), 7.12 (1H, d), 7.19 (2H, m), 7.62 (1H, m), 7.90 (1H, d), 8.76 (1H, s), 11.01 (1H, s). LRMS : m/z 595 (M + 1)$^+$ | b |
| 5 | *-CH$_2$-(2-pyridyl) | (CH$_2$)$_2$OH | NH$_2$ | δ (CDCl$_3$) : 1.18 (3H, t), 2.05 (2H, m), 2.36 (1H, s), 2.57 (2H, t), 2.63 (4H, m), 3.13 (4H, m), 3.60 (2H, t), 4.31 (2H, t), 6.03 (3H, m), 7.14–7.30 (3H, m), 7.63 (1H, m), 7.92 (2H, m), 8.54 (1H, d), 8.75 (1H, s), 11.05 (1H, s). LRMS : m/z 597 (M + 1)$^+$ | a |

-continued

| Example | R¹ | R¹⁶ | NR¹²R¹³ | Data | Method |
|---|---|---|---|---|---|
| 6 | *-CH₂-(2-pyridyl) | (CH₂)₂OH | NHCH₃ | Found: C, 54.38; H, 5.56; N, 17.96. $C_{28}H_{34}N_8O_6S;0.50H_2O$ requires C, 50.27; H, 5.69; N, 18.08%. δ (CDCl₃): 1.18 (3H, t), 2.05 (2H, m), 2.57 (2H, t), 2.64 (4H, m), 3.13 (7H, m), 3.59 (2H, t), 4.30 (2H, t), 6.03 (2H, s), 7.08–7.25 (3H, m), 7.62 (1H, m), 7.91 (1H, d) 8.07 (1H, m), 8.54 (1H, d), 8.79 (1H, s). LRMS: m/z 611 (M + 1)⁺ | b |
| 7 | *-CH₂-(3-pyridyl) | CH₃ | NH₂ | Found: C, 53.02; H, 5.23; N, 19.01. $C_{26}H_{30}N_8O_5S$; 1.5H₂O requires C, 52.60; H, 5.60; N, 18.87%. δ (DMSOd6): 0.93 (3H, t), 1.70 (2H, m), 2.14 (3H, s), 2.36 (4H, m), 2.90 (4H, m), 4.12 (2H, t), 5.89 (2H, s), 7.40 (2H, m), 7.72 (2H, m), 7.77 (1H, s), 7.83 (1H, d), 7.90 (1H, s), 8.52 (1H, d), 8.60 (1H, s), 12.51 (1H, s). LRMS: m/z 567 (M + 1)⁺ | b |
| 8 | *-CH₂-(3-pyridyl) | CH₃ | NHCH₃ | Found: C, 55.28; H, 556; N, 18.97. $C_{27}H_{32}N_8O_5S$;0.50H₂O requires C, 55.00; H, 5.64; N, 19.00%. δ (CDCl₃): 1.18 (3H, t), 2.05 (2H, m), 2.28 (3H, s), 2.50 (4H, m), 3.10 (7H, m), 4.28 (2H, t), 5.90 (2H, s), 7.23 (2H, m), 7.87 (2H, m), 8.06 (1H, m), 8.54 (1H, d), 8.68 (1H, s), 8.78 (1H, s), 11.01 (1H, s). LRMS: m/z 581 (M + 1)⁺ | b |
| 9 | *-CH₂-(3-pyridyl) | CH₂CH₃ | NH₂ | Found: C, 55.12; H, 5.48; N, 19.12. $C_{27}H_{32}N_8O_5S;0.50H_2O$ requires C, 55.00; H, 5.64; N, 19.00%. δ (DMSOd₆): 0.92 (6H, m), 1.74 (2H, m), 2.30 (2H, q), 2.40 (4H, m), 2.90 (4H, m), 4.12 (2H, t), 5.88 (2H, s), 7.40 (2H, m), 7.69–7.92 (5H, m), 8.52 (1H, d), 8.60 (1H, s), 12.63 (1H, s) LRMS: m/z 581 (M + 1)⁺ | a |
| 10 | *-CH₂-(3-pyridyl) | CH₂CH₃ | NHCH₃ | Found: C, 54.38; H, 5.59; N, 18.01. $C_{28}H_{34}N_5O_5S;1.5H_2O$ requires C, 54.09; H, 6.00; N, 18.02%. δ (CDCl₃): 1.02 (3H, t), 1.20 (3H, t), 2.06 (2H, m), 2.41 (2H, q), 2.55 (4H, m), 3.10 (7H, m), 4.30 (2H, t), 5.90 (2H, s), 7.22 (2H, m), 7.88 (2H, m), 8.08 (1H, m), 8.56 (1H, d), 8.70 (1H, s), 8.78 (1H, s), 11.05 (1H, s). LRMS: m/z 595 (M + 1)⁺ | b |

-continued

| Example | R$^1$ | R$^{16}$ | NR$^{12}$R$^{13}$ | Data | Method |
|---|---|---|---|---|---|
| 11 | *-CH$_2$-(3-pyridyl) | (CH$_2$)$_2$OH | NH$_2$ | Found: C, 52.64; H, 5.47; N, 17.84. C$_{27}$H$_{32}$N$_8$O$_6$S ;H$_2$O requires C, 52.76; H, 5.58; N, 18.23%. δ (CDCl$_3$) : 1.20 (3H, t), 2.06 (2H, m), 2.56 (2H, t), 2.60 (4H, m), 3.10 (4H, m), 3.60 (2H, t), 4.30 (2H, t), 5.92 (2H, s), 6.11 (1H, s), 7.24 (3H, m), 7.90 (3H, m), 8.56 (1H, 8.68 (1H, s), 8.80 (1H, s). LRMS : m/z 597 (M + 1)$^+$ | b |
| 12 | *-CH$_2$-(3-pyridyl) | (CH$_2$)$_2$OH | NHCH$_3$ | Found : C, 53.56; H, 5.60; N, 17.44. C$_{25}$H$_{34}$N$_8$O$_6$S;H$_2$O requires C, 55.36; H, 5.66; N, 17.43%. δ (CDCl$_3$) : 1.20 (3H, t), 2.07 (2H, m), 2.57 (2H, t), 2.62 (4H, m), 3.11 (7H, m), 3.59 (2H, t), 4.32 (2H, t), 5.90 (21 s), 7.22 (2H, m), 7.84 (1H, d 7.90 (1H, d), 8.04 (1H, m) 8.56 (1H, d), 8.70 (1H,s,) 8.78 (1H, s). LRMS : m/z 611 (M + 1)$^+$ | b |
| 13 | *-CH$_2$-(4-pyridyl) | CH$_3$ | NHCH$_3$ | Found: 54.89; H, 5.60; N, 19.02. C$_{27}$H$_{32}$N$_8$O$_5$S;0.50H$_2$O requires C, 55.oo; H, 5.64; N 19.00%. δ (CDCl$_3$) : 1.19 (3H, t), 2.06 (2H, m), 2.29 (3H, s), 2.52 (4H, m), 3.10 (7H, m), 4.30 (2H, t), 5.86 (2H, s), 7.20 (1H, d), 7.31 (2H, d), 7.90 (1H, d), 8.08 (1H, m), 8.57 (2H, d), 8.73 (1H, s), 11.05 (1H, s). LRMS : m/z 581 (M + 1)$^+$ | a |
| 14 | *-CH$_2$-(4-pyridyl) | CH$_2$CH$_3$ | NHCH$_3$ | Found: C, 55.85; H, 5.91; N, 18.30. C$_{28}$H$_{34}$N$_8$O$_5$S;0.50H$_2$O requires C, 55.70; H, 5.84; N, 18.56%. δ (CDCl$_3$) : 1.03 (3H, t), 1.20 (3H, t), 2.06 (2H, m), 2.42 (2H, q), 2.56 (4H, m), 3.12 (7H, m), 4.30 (2H, t), 5.87 (2H, s), 7.20 (1H, d), 7.31 (2H, d), 7.92 (1H, d), 8.09 (1H, m), 8.57 (2H, d), 8.74 (1H, s), 11.05 (1H, s). LRMS : m/z 595 (M + 1)$^+$ | a |

EXAMPLE 15

1-(4-Bromobenzyl)-5-[5-(4methylpiperazin-1-ylsulphonyl)-2-n-propoxyphenyl]-7-oxo-1,6-dihydro-1H-pyrazolo[4,3-d]pyrimidine-3-N-methylcarboxamide Thionyl chloride (81 μl, 1.1 mmol) and chlorosulphonic acid (0.44 μl, 6.67 mmol) were added to an ice-cooled flask containing the title compound of Preparation 36 (370 mg, 0.74 mmol) and the reaction stirred at room temperature for 18 hours. Ice (1 g) was carefully added with stirring, and the resulting precipitate filtered, washed with water and dried under suction. N-Methylpiperazine (416μl, 3.75 mmol) was added to a suspension of this product in ethanol (5 ml), and the reaction stirred at room temperature for an hour. The reaction mixture was evaporated under reduced pressure and the residue purified by column chromatography on silica gel, using dichloromethane:methanol:0.88 ammonia (95:5:1) as eluant. This product was recrystallised from dichloromethane-hexane to afford the title compound (270 mg, 55%) as a white solid.

Found: C, 50.08; H, 4.78; N, 14.45. C$_{28}$H$_{32}$BrN$_7$O$_5$S;H$_2$O requires C, 49.71; H, 5.07; N, 14.49%.

δ(CDCl$_3$): 1.20 (3H, t), 2.07 (2H, m), 2.30 (3H, s), 2.52 (4H, m), 3.12 (7H, m), 4.30 (2H, t), 5.81 (2H, s), 7.21 (1H, d), 7.40 (4H, m), 7.90 (1H, d), 8.06 (1H, m), 8.72 (1H, s), 11.00 (1H, s).

LRMS: m/z 659 (M+1)$^+$

EXAMPLE 16

1-(4-Bromobenzyl)-5-[5-(4-ethylpiperazin-1-ylsulphonyl)-2-n-propoxyphenyl]-7-oxo-1,6-dihydro-1H-pyrazolo[4,3-d]pyrimidine-3-N-methylcarboxamide Obtained (63%) from the title compound of Preparation 36 and N-ethylpiperazine using the procedure of Example 15.

δ(CDCl$_3$): 1.04 (3H, t), 1.20 (3H, t), 2.06 (2H, m), 2.42 (2H, q), 2.56 (4H, m), 3.12 (7H, m), 4.30 (2H, t), 5.81 (2H, s), 7.20 (1H, d), 7.41 (4H, m), 7.91 (1H, d), 8.08 (1H, m), 8.72 (1H, s), 11.00 (1H, s).

LRMS: m/z 673 (M+1)$^+$

EXAMPLE 17

1-(4-Bromobenzyl)-5-{5-[4-(2-hydroxyethyl)piperazin-1-ylsulphonyl]-2-n-propoxyphenyl}-7-oxo-1,6-dihydro-1H-pyrazolo[4,3-d]pyrimidine-3-N-methylcarboxamide Obtained as fine white crystals after crystallization from ethanol (70%), from the title compound of Preparation 36 and N-(2-hydroxyethyl)piperazine, using the procedure of Example 15.

Found: C, 50.15; H, 5.01; N, 13.97. C$_{29}$H$_{34}$BrN$_7$O$_6$S requires C, 50.59; H, 4.98; N, 14.24%.

δ(CDCl$_3$): 1.20 (3H, t), 2.06 (2H, m), 2.26 (1H, s), 2.58 (2H, t), 2.63 (4H, m), 3.12 (7H, m), 3.60 (2H, m), 4.32 (2H, t), 5.81 (2H, s), 7.22 (1H, d), 7.40 (4H, m), 7.90 (1H, d), 8.04 (1H, m), 8.75 (1H, s), 11.02 (1H, s).

LRMS: m/z 688 (M)$^+$

EXAMPLE 18

1-Benzyl-5-[2-ethoxy-5-(4methylpiperazin-1-ylsulphonyl)]-7-oxo-1,6-dihydro-1H-pyrazolo[4,3-d]pyrimidine-3-carboxamide N,N'-Carbonyldiimidazole (80 mg, 0.5 mmol) was added to a suspension of the title compound of Preparation 72 (250 mg, 0.46 mmol) in tetrahydrofuran (15 ml), and the reaction heated under reflux and a nitrogen atmosphere for 4 hours. The solution was cooled in ice, ammonia gas bubbled through for 5 minutes, and then stirred at room temperature for 14 hours. The mixture was filtered, the precipitate washed with ethyl acetate, and dried under suction to afford the title compound (225 mg, 89%) as a white solid.

Found: C, 55.32; H, 5.26; N, 17.22. C$_{26}$H$_{29}$N$_7$O$_5$S;0.75H$_2$O requires C, 55.36; H, 5.44; N, 17.35%.

δ(DMSOd$_6$): 1.33 (3H, t), 2.16 (3H, s), 2.39 (4H, m), 2.91 (4H, m), 4.22 (2H, q), 5.82 (2H, s), 7.37 (6H, m), 7.70 (1H, s), 7.79 (1H, s), 7.84 (1H, m), 7.92 (1H, s), 12.66 (1H, s).

LRMS: m/z 552 (M+1)$^+$

EXAMPLE 19

1-Benzyl-5-[2-ethoxy-5-(4-methylpiperazin-1-ylsulphonyl)]-7-oxo-1,6-dihydro-1H-pyrazolo[4,3-d]pyrimidine -3-N-methylcarboxamide 1-(3-Dimethylaminopropyl)-3-ethylcarbodiimide hydrochloride (250 mg, 0.45 mmol), was added to a suspension of the title compound of Preparation 72 (250 mg, 0.45 mmol), N-methylmorpholine (0.11 ml, 1.0 mmol), 1-hydroxybenzotriazole hydrate (67 mg, 0.50 mmol) and methylamine hydrochloride (67 mg, 1.0 mmol) in dichloromethane (7 ml) and the reaction stirred at room temperature for 18 hours. The mixture was partitioned between dichloromethane (15 ml) and aqueous sodium bicarbonate solution (15 ml), the phases separated and the aqueous layer extracted with dichloromethane (2×15 ml). The combined organic extracts were dried (Na$_2$SO$_4$) and evaporated under reduced pressure. The residual solid was purified by column chromatography on silica gel, using an elution gradient of dichloromethane:methanol (100:0 to 95:5) to afford the title compound (250 mg, 98%) as a white solid.

Found: C, 56.60; H, 5.53; N, 16.84. C$_{27}$H$_{31}$N$_7$O$_5$S;CH$_3$OH requires C, 57.11; H, 5.60; N, 17.14%.

δ(CDCl$_3$): 1.67 (3H, t), 2.30 (3H, s), 2.52 (4H, m), 3.12 (7H, m), 4.41 (2H, q), 5.86 (2H, s), 7.20 (1H, d), 7.30 (3H, m), 7.52 (2H, m), 7.90 (1H, d), 8.08 (1H, m), 8.72 (1H, s), 10.98 (1H, s).

EXAMPLE 20

1-Benzyl-5-[2-ethoxy-5-(4methylpiperazin-1-ylsulphonyl)]-7-oxo-1,6-dihydro-1H-pyrazolo[4,3-d]pyrimidine-3-N-ethylcarboxamide Obtained (77%) from the title compound of Preparation 72 and ethylamine hydrochloride, using the procedure described in Example 19.

Found: C, 57.33; H, 5.73; N, 16.56. C$_{28}$H$_{33}$N$_7$O$_5$S requires C, 58.01; H, 5.74; N, 16.91%.

δ(CDCl$_3$): 1.37 (3H, t), 1.67 (3H, t), 2.26 (3H, s), 2.49 (4H, m), 3.10 (4H, m), 3.60 (2H, m), 4.40 (2H, q), 5.85 (2H, s), 7.20 (1H, d), 7.28 (3H, m), 7.50 (2H, m), 7.88 (1H, d), 8.02 (1H, m), 8.78 (1H, s), 11.05 (1H, s).

EXAMPLE 21

1-Benzyl-5-[2-ethoxy-5-(4-methylpiperazin-1-ylsulphonyl)]-7-oxo-1,6-dihydro-1H-pyrazolo[4,3-d]pyrimidine-3-N,N-ethylcarboxamide Obtained as a white solid (86%) from the title compound of Preparation 72 and dimethylamine hydrochloride, using the procedure of Example 19.

δ(CDCl$_3$): 1.66 (3H, t), 2.27 (3H, s), 2.50 (4H, m), 3.10 (4H, m), 3.15 (3H, s), 3.20 (3H, s), 4.39 (2H, q), 5.82 (2H, s), 7.16 (1H, d), 7.31 (3H, m), 7.48 (2H, m), 7.84 (1H, d), 8.82 (1H, s), 11.00 (1H, s).

LRMS: m/z 580 (M+1)$^+$

EXAMPLE 22

1-Benzyl-5-[5-(4-methylpiperazin-1-ylsulphonyl)-2-n-propoxyphenyl]-7-oxo-1,6-dihydro-1H-pyrazolo[4,3-d]pyrimidine-3-N-methylcarboxamide Triethylamine (140 μl, 1.0 mmol), palladium (0) tetrakis (triphenyl)-phosphine (40 mg, 0.034 mmol) and sodium formate (68 mg, 1.0 mmol) were added to a solution of the title compound of Example 15 (220 mg, 0.33 mmol) in acetonitrile:dimethylsulphoxide (4 ml, 1:1), and the reaction heated under reflux for 18 hours. The cooled reaction mixture was concentrated under reduced pressure, the residue suspended in water (10 ml) and extracted with dichloromethane (3×10 ml), the combined organic extracts dried (Na$_2$SO$_4$) and evaporated under reduced pressure. The residual yellow solid was purified by column chromatography on silica gel, using dichloromethane:methanol:0.88 ammonia (95:5:1) as eluant and recrystallised from ethanol to afford the title compound (94 mg, 49%) as a white powder.

Found: C, 57.88; H, 5.78; N, 16.56. C$_{28}$H$_{33}$N$_7$O$_5$S requires C, 58.02; H, 5.74; N, 16.91%.

δ(CDCl$_3$): 1.20 (3H, t), 2.06 (2H, m), 2.29 (3H, s), 2.50 (4H, m), 3.10 (7H, m), 4.30 (2H, t), 5.86 (2H, s), 7.20 (1H, d), 7.30 (3H, m), 7.50 (2H, m), 7.90 (1H, d), 8.08 (1H, m), 8.73 (1H, s), 10.98 (1H, s).

LRMS: m/z 580 (M+1)$^+$

EXAMPLE 23

1-Benzyl-5-[5-(4-ethylpiperazin-1-ylsulphonyl)-2-n-propoxyphenyl]-7-oxo-1,6-dihydro-1H-pyrazolo[4,3-d]pyrimidine-3-N-methylcarboxamide Obtained as a white solid (34%) from the title compound of Example 16, using the procedure of Example 22.

Found: C, 58.44; H, 6.04; N, 16.14. $C_{29}H_{35}N_7O_5S$ requires C, 58.67; H, 5.94; N, 16.51%.

δ($CDCl_3$) 1.03 (3H, t), 1.20 (3H, t), 2.05 (2H, m), 2.42 (2H, q), 2.56 (4H, m), 3.12 (7H, m), 4.28 (2H, t), 5.86 (2H, s), 7.20 (1H, d), 7.30 (3H, m), 7.52 (2H, m), 7.90 (1H, d), 8.07 (1H, m), 8.72 (1H, s), 10.98 (1H, s).

EXAMPLE 24

1-Benzyl-5-{5-[4-(2-hydroxyethyl)piperazin-1-ylsulphonyl]-2-n-propoxyphenyl}-7-oxo-1,6-dihydro-1H-pyrazolo[4,3-d]pyrimidine-3-N-methylcarboxamide Obtained as a white powder (55%) from the title compound of Example 17, using the procedure of Example 22.

Found: C, 57.01; H, 5.85; N, 15.79. $C_{29}H_{35}N_7O_6S$ requires C, 57.13; H, 5.79; N, 16.08%.

δ($CDCl_3$): 1.20 (3H, t), 2.06 (2H, m), 2.26 (1H, s), 2.58 (2H, t), 2.63 (4H, m), 3.12 (7H, m), 3.59 (2H, m), 4.30 (2H, t), 5.86 (2H, s), 7.20 (1H, d), 7.30 (3H, m), 7.50 (2H, m), 7.90 (1H, d), 8.05 (1H, m), 8.75 (1H, s), 11.00 (1H, s).

LRMS: m/z 611 (M+2)$^+$

EXAMPLE 25

5-[5-(4-Methylpiperazin-1-ylsulphonyl)-2-n-propoxyphenyl]-7-oxo-2,6-dihydro-2H-pyrazolo[4,3-d]pyrimidine-3-carboxamide hydrochloride Thionyl chloride (1 ml, 13.7 mmol) was added to an ice-cooled solution of the title compound of Preparation 32 (490 mg, 1.56 mmol) in chlorosulphonic acid (2 ml, 30.0 mmol), and the reaction stirred at room temperature for 18 hours. The reaction mixture was poured carefully onto ice (10 g), and the resulting precipitate filtered, washed with water and dried under suction to give a beige solid (360 mg). N-Methylpiperazine (180 ml, 1.65 mmol) was added to a suspension of this solid in ethanol (20 ml) and the reaction stirred at room temperature for 18 hours. The reaction mixture was concentrated under reduced pressure, the residue suspended in water (10 ml), and acidified to pH 6 with 2N hydrochloric acid. The resulting precipitate was filtered, washed with water and diethyl ether and dried at 60° C. to afford the title compound (305 mg, 44%) as an off-white powder.

δ($DMSOd_6$): 0.94 (3H, t), 1.73 (2H, m), 2.23–3.10 (11H, m), 4.14 (2H, t), 7.40 (1H, d), 7.59 (1H, s), 7.85 (2H, m), 7.96 (1H, s), 12.37 (1H, s), 14.90 (1H, s).

LRMS: m/z 476 (M+1)$^+$

EXAMPLE 26

2-Methyl-5-[5-(4methylpiperazin-1-ylsulphonyl)-2-n-propoxyphenyl]-7-oxo-2,6-dihydro-2H-pyrazolo[4,3-d]pyrimidine-3-carboxamide Thionyl chloride (500 μl, 6.85 mmol) was added to an ice-cooled solution of the title compound of Preparation 60 (125 mg, 0.37 mmol) in chlorosulphonic acid (1.0 ml, 15.0 mmol) and the reaction stirred at room temperature for 18 hours. The reaction mixture was poured carefully onto ice (5 g), and the aqueous solution extracted with dichloromethane (3×15 ml). The combined organic extracts were dried ($MgSO_4$) and evaporated under reduced pressure, and the residue triturated with water and diethyl ether, to give a white solid (90 mg). N-Methyl piperazine (40 μl, 0.36 mmol) was added to a suspension of this product in ethanol (5 ml) and the reaction stirred at room temperature for 18 hours. The reaction mixture was concentrated under reduced pressure, the residue dissolved in dichloromethane (25 ml), washed with water (2×10 ml), dried ($MgSO_4$) and evaporated under reduced pressure to afford the tide compound (82 mg, 50%) as a white solid.

Found: C, 50.50; H, 5.64; N, 18.32. $C_{22}H_{29}N_7O_5S;H_2O$ requires C, 50.66; H, 5.99; N, 18.79%.

δ($DMSOd_6$): 0.92 (3H, t), 1.70 (2H, m), 2.15 (3H, s), 2.36 (4H, m), 2.85 (3H, d), 2.92 (4H, m), 4.11 (2H, t), 4.36 (3H, s), 7.38 (1H, d), 7.82 (1H, d), 7.92 (1H, s), 8.28 (1H, m), 12.18 (1H, s).

LRMS: m/z 504 (M+1)$^+$

EXAMPLE 27

1-Methyl-5-[5-(4-methylpiperazin-1-ylsulphonyl)-2-n-propoxyphenyl]-7-oxo-1,6-dihydro-1H-pyragolo[4,3-d]pyrimidine-3-carboxamide hydrochloride Obtained as a white solid (80%) from the title compound of Preparation 61 and N-methylpiperazine using the procedure of Example 25.

Found: C, 48.58; H, 5.35; N, 18.59. $C_{22}H_{29}N_7O_5S;HCl$ requires C, 47.95; H, 5.31; N, 18.64%.

δ($DMSOd_6$): 0.94 (3H, t), 1.73 (2H, m), 2.16 (3H, s), 2.39 (4H, m), 2.90 (4H, m), 4.12 (2H, t), 4.28 (3H, s), 7.40 (1H, d), 7.65 (1H, s), 7.72 (1H, s), 7.84 (1H, d), 7.90 (1H, s), 12.54 (1H, s).

LRMS: m/z 490 (M+1)$^+$

EXAMPLE 28

5-[5-(4-Ethylpiperazin-1-ylsulphonyl)-2-n-propoxyphenyl]-1-methyl-7-oxo-1,6-dihydro-1H-pyrazolo[4,3-d]pyrimidine-3-carboxamide Obtained as a white solid (82%) from the title compound of Preparation 61 and N-ethylpiperazine using the procedure of Example 26.

Found: C, 50.05; H, 5.89; N, 18.12. $C_{22}H_2N_7O_5S;1.20H_2O$ requires C, 50.31; H, 6.03; N, 18.67%.

δ($CDCl_3$): 1.03 (3H, t), 1.20 (3H, t), 2.07 (2H, m), 2.41 (2H, q), 2.55 (4H, m), 3.10 (4H, m), 4.30 (2H, t), 4.40 (3H, s), 5.84 (1H, s), 7.21 (1H, d), 7.90 (2H, m), 8.70 (1H, s), 11.00 (1H, s).

LRMS: m/z 504 (M+1)$^+$

EXAMPLE 29

1-Cyclobutylmethyl-5-[5-(4-methylpiperazin-1-ylsulphonyl)-2-n-propoxyphenyl]-7-oxo-1,6-dihydro-1H-pyrazolo[4,3-d]pyrimidine-3-N-methylcarboxamide Obtained as a white solid (89%) from the title compound of Preparation 37 and N-methylpiperazine, using the procedure of Example 15.

Found: C, 55.60; H, 6.29; N, 17.37. $C_{26}H_{35}N_7O_5S$ requires C, 56.00; H, 6.33; N, 17.58%.

δ($CDCl_3$): 1.18 (3H, t), 1.86 (4H, m), 1.95–2.06 (4H, m), 2.25 (3H, s), 2.49 (4H, m), 3.00 (1H, m), 3.08 (7H, m), 4.28 (2H, t), 4.70 (2H, d), 7.18 (1H, d), 7.85 (1H, d), 8.04 (1H, m), 8.72 (1H, s), 10.95 (1H, s).

LRMS: m/z 559 (M+2)$^+$

EXAMPLE 30

5-[5-(4-Methylpiperazin-1-ylsulphonyl)-2-n-propoxyphenyl]-1-[2-(4-morpholinyl)ethyl]-7-oxo1,6dihydro-1H-pyrazolo[4,3-d]pyrimidine-3-N-methylcarboxamide Obtained (15%) from the title compound of Preparation 31 and N-methylpiperazine using the procedure of Example 1.

δ(CDCl$_3$): 1.20 (3H, t), 2.08 (2H, m), 2.30 (3H, s), 2.54 (8H, m), 2.96 (2H, t), 3.11 (4H, m), 3.60 (4H, m), 4.32 (2H, t), 4.83 (2H, t), 5.93 (1H, s), 7.21 (1H, d), 7.90 (1H, d), 7.98 (1H, s), 8.73 (1H, s), 11.03 (1H, s).

LRMS: m/z 589 (M+1)$^+$

EXAMPLE 31

5-[5-(4-Ethylpiperazin-1-ylsulphonyl)-2-(n-propoxy) pyridin-3-yl]-7-oxo-2-(pyridin-2-yl)methyl-2,6-dihydro-2H-pyrazolo[4,3-d]pyrimidine-3-carboxamide and

EXAMPLE 32

5-[5-(4-Ethylpiperazin-1-ylsulphonyl)-2n-propoxy) pyridin-3-yl]-7-oxo-1-(pyridin-2-yl)methyl-1,6-dihydro-1H-pyrazolo[4,3-d]pyrimidine-3-carboxamide A mixture of the title compound of Preparation 73 (380 mg, 0.65 mmol) and potassium bis(trimethylsilyl)amide (518 mg, 2.60 mmol) in ethanol (20 ml) was heated at 100° C. in a sealed vessel for 18 hours. The cooled reaction mixture was concentrated under reduced pressure, the residue dissolved in water (7 ml), neutralised with 50% aqueous citric acid and the aqueous solution extracted with dichloromethane (3×30 ml). The combined organic extracts were dried (MgSO$_4$), and evaporated under reduced pressure. The residual brown foam was purified by column chromatography on silica gel, using an elution gradient of dichloromethane:methanol (98:2 to 95:5), and azeotroped with dichloromethane and diethyl ether, to afford the title compound of Example 31 (8 mg, 2%) as a white solid:

δ(CDCl$_3$): 1.04 (3H, t), 1.60 (3H, t), 2.42 (2H, q), 2.58 (4H, m), 3.15 (4H, m), 4.79 (2H, q), 5.77 (1H, s), 6.30 (2H, s), 7.11 (1H, d), 7.19 (1H, m), 7.62 (1H, m), 8.15 (1H, s), 8.54 (1H, d), 8.70 (1H, s), 8.88 (1H, s), 10.81 (1H, s);

LRMS: m/z 568 (M+1)$^+$; and the title compound of Example 32 (200 mg, 54%) as a white solid.

Found: C, 52.53; H, 5.08; N, 21.83. C$_{25}$H$_{29}$N$_9$O$_5$S requires C, 52.90; H, 5.15; N, 22.21%.

δ(CDCl$_3$): 1.05 (3H, t), 1.59 (3H, t), 2.42 (2H, q), 2.57 (4H, m), 3.15 (4H, m), 4.79 (2H, q), 5.86 (1H, s), 6.06 (2H, s), 7.19 (2H, m), 7.64 (1H, m), 7.79 (1H, s), 8.54 (1H, d), 8.71 (1H, s), 8.98 (1H, s), 11.02 (1H, s).

LRMS: m/z 568 (M+1)$^+$

EXAMPLE 33

5-[5-(4-Ethylpiperazin-1-ylsulphonyl)-2-(2-methoxyethoxy)pyridin-3-yl]-7-oxo-1-(pyridin-2-yl) methyl-1,6-dihydro-1H-pyrazolo[4,3-d]pyrimidine-3-carboxamide A mixture of 2-methoxyethanol (10 ml) and potassium bis(trimethylsilyl)amide (175.7 mg, 0.88 mmol) was heated at 90° C. for an hour, then cooled. The title compound of Example 32 (100 mg, 0.17 mmol) was added and the reaction heated at 110° C. for 18 hours. The cooled reaction mixture was concentrated under reduced pressure, the residue dissolved in water (5 ml) and neutralised with 20% aqueous citric acid. The aqueous solution was extracted with dichloromethane (3×10 ml), the combined organic extracts dried (MgSO$_4$) and evaporated under reduced pressure. The residual brown oil was purified by column chromatography on silica gel, using an elution gradient of dichloromethane:methanol (98:2 to 95:5) and azeotroped with dichloromethane and diethyl ether, to afford the title compound (94 mg, 90%) as a white solid.

Found: C, 51.73; H, 5.22; N, 20.49. C$_{26}$H$_{31}$N$_9$O$_6$S requires C, 52.25; H, 5.23; N, 21.09%.

δ(CDCl$_3$): 1.04 (3H, t), 2.43 (2H, q), 2.57 (4H, m), 3.16 (4H, m), 3.58 (3H, s), 3.87 (3H, t), 4.81 (2H, t), 5.85 (1H, s), 6.08 (2H, s), 7.18 (2H, m), 7.64 (1H, m), 7.80 (1H, s), 8.55 (1H, d), 8.70 (1H, s), 8.89 (1H, s), 11.28 (1H, s).

LRMS: m/z 598 (M+1)$^+$

EXAMPLE 34

5-[5-(4Ethylpiperazin-1-ylsulphonyl)-2-(2-methoxyethoxy)pyridin-3-yl]-7-oxo2-(pyridin-2yl) methyl-2,6-dihydro-1H-pyrazolo[4,3-d]pyrimidine-3-N-methylcarboxamide Obtained as a beige solid (38%) from the title compound of Preparation 74, using a similar procedure to that described in Example 31.

Found: C, 53.25; H, 5.47; N, 21.21. C$_{26}$H$_3$N$_9$O$_5$S requires C, 53.69; H, 5.37; N, 21.67%.

δ(CDCl$_3$): 1.05 (3H, t), 1.59 (3H, t), 2.42 (2H, q), 2.57 (4H, m), 3.05 (3H, d), 3.15 (4H, m), 4.79 (2H, q), 6.34 (2H, s), 7.10 (1H, d), 7.18 (1H, m), 7.62 (1H, m), 8.28 (1H, m), 8.54 (1H, d), 8.70 (1H, s), 8.92 (1H, s), 10.75 (1H, s).

LRMS: m/z 582 (M+1)$^+$

EXAMPLE 35

5-[2-Ethoxy-5-(4-ethylpiperazin-1-ylsulphonyl) pyridin-3-yl]-7-oxo2-methyl-2,6-dihydro-2H-pyrazolo[4,3-d]pyrimidine-3-N-methylcarboxamide Obtained as a white solid (57%), from the title compound of Preparation 75, using a similar procedure to that described in Example 31.

Found: C, 49.69; H, 5.54; N, 21.85. C$_{21}$H$_{28}$N$_8$O$_5$S requires C, 49.99; H, 5.59; N, 22.20%.

δ(CDCl$_3$): 1.05 (3H, t), 1.59 (3H, t), 2.42 (2H, q), 2.57 (4H, m), 3.09 (3H, d), 3.15 (4H, m), 4.54 (3H, s), 4.79 (2H, q), 8.21 (1H, m), 8.70 (1H, s), 8.90 (1H, s), 10.75 (1H, s).

LRMS: m/z 505 (M+1)$^+$

EXAMPLE 36

5-[5-(4-Ethylpiperazin-1-ylsulphonyl)-2-(2-methoxyethoxy)pyridin-3-yl]-7-oxo-2-methyl-2,6-dihydro-2H-pyrazolo[4,3-d]pyrimidine-3-N-methylcarboxamide Obtained as a white solid (73%), from the title compound of Example 35, using the procedure of Example 33.

Found C, 48.53; H, 5.76; N, 20.51. C$_{22}$H$_{30}$N$_8$O$_6$S; 0.5H$_2$O requires C, 48.61; H, 5.75; N, 20.61%.

δ(CDCl$_3$): 1.04 (3H, t), 2.43 (2H, q), 2.57 (4H, m), 3.08 (3H, d), 3.16 (4H, m), 3.59 (3H, s), 3.87 (2H, t), 4.53 (3H, s), 4.80 (2H, t), 8.22 (1H, m), 8.68 (1H, s), 8.81 (1H, s), 11.00 (1H, s).

LRMS: m/z 535 (M+1)$^+$

EXAMPLE 37

5-{5-4Ethylpiperazin-1-ylsulphonyl)-2-[(pyridin-2-yl)methoxy]pyrimidine-3-yl}-7-oxo2-methyl-2,6-dihydro-2H-pyrazolo[4,3-d]pyrimidine-3-N-methylcarboxamide Obtained as a white solid (33%) from the title compound of Example 35 and 2-(hydroxymethyl)pyridine using the procedure of Example 33.

δ(CDCl₃): 1.04 (3H, t), 2.42 (2H, q), 2.57 (4H, m), 3.09 (3H, d), 3.15 (4H, m), 4.56 (3H, s), 5.98 (2H, s), 7.37 (2H, m), 7.79 (1H, m), 8.30 (1H, m), 8.66 (2H, m), 8.87 (1H, d), 13.68 (1H, s).

LRMS: 568 (M+1)$^+$

EXAMPLE 38

5-[5-(4-Ethylpiperazin-1-ylsulphonyl)-2-n-propoxyphenyl]-3-(pyridin-2-yl)-1,6-dihydro-1H-7H-pyrazolo[4,3-d]pyrimidin-7-one A mixture of the title compound of Preparation 88 (120 mg, 0.35 mmol), chlorosulphonic acid (230 μl, 3.5 mmol) and thionyl chloride (38 μl, 0.52 mmol) was stirred at room temperature for 18 hours. The mixture was cooled in an ice-bath, ice (1 g) added, followed by N-thylpiperazine (2 ml) and ethanol (1 ml) and the reaction stirred at room temperature for 5 hours. The mixture was partitioned between dichloromethane (10 ml) and sodium bicarbonate solution (5 ml), and the phases separated. The aqueous layer was extracted with dichloromethane (3×10 ml), the combined organic solutions washed with brine (20 ml), dried ($Na_2SO_4$ and evaporated under reduced pressure. The residue was purified by column chromatography on silica gel, using an elution gradient of dichloromethane:methanol (100:0 to 98:2) to afford the title compound, (120 mg, 66%) as a pale pink solid.

Found: C, 56.58; H, 5.63; N, 18.25. $C_{25}H_{29}N_7O_4S$; $0.5H_2O$ requires C, 56.38; H, 5.68; N, 18.41%.

δ(CDCl₃): 1.05 (3H, t), 1.21 (3H, t), 2.15 (2H, m), 2.62 (2H, q), 2.78 (4H, m), 3.28 (4H, m), 4.35 (2H, t), 7.15 (1H, m), 7.23 (1H, d), 7.58 (1H, m), 7.94 (1H, d), 8.29 (1H, d), 8.52 (1H, s), 8.77 (1H, s), 10.89 (1H, s), 13.82 (1H, s).

LRMS: m/z 524 (M+1)$^+$

EXAMPLE 39

5-[5-(4-Ethylpiperazin-1-ylsulphonyl)-2-n-propoxyphenyl]-3-(pyridin-3-yl)-1,6-dihydro-1H-7H-pyrazolo[4,3-d]pyrimidin-7-one A mixture of the title compound of Preparation 89 (150 mg, 0.43 mmol) chlorosulphonic acid (230 μl, 3.46 mmol) and thionyl chloride (40 μl, 0.52 mmol) was stirred at room temperature for 18 hours. Ice (5 g) was added, followed by N-thylpiperazine (3 ml) and ethanol (1 ml) and the reaction stirred for a further 4 hours. The mixture was partitioned between water (10 ml) and dichloromethane (10 ml), the layers separated and the aqueous phase extracted with dichloromethane (3×10 ml). The combined organic solutions were dried ($Na_2SO_4$) and evaporated under reduced pressure, and the residue triturated with ethanol to afford the title compound (106 mg, 47%) as a pale yellow solid.

δ(CDCl₃): 0.82 (3H, t), 0.97 (3H, t), 1.82 (2H, m), 2.23 (2H, q), 2.38 (4H, m), 2.96 (4H, m), 4.06 (2H, t), 7.02 (1H, d), 7.19 (1H, m), 7.68 (1H, d), 8.40 (1H, d), 8.50 (2H, m), 9.38 (1H, s).

LRMS: m/z 524 (M+1)$^+$

EXAMPLE 40

5-[5-(4-Ethylpiperazin-1-ylsulphonyl)-2-n-propoxyphenyl]-3-(pyridin-2-yl)-2-(pyridin-2-yl) methyl-2,6-dihydro-7H-pyrazolo[4,3-d]pyrimidin-7-one Obtained as a white solid (25%) from the title compound of Preparation 91 using a similar procedure to that described in Example 38.

Found: C, 59.63; H, 5.65; N, 17.69. $C_{31}H_{34}N_8O_4S$;$0.5H_2O$ requires C, 59.70; H, 5.66; N, 17.96%.

δ(CDCl₃): 1.02 (3H, t), 1.20 (3H, t), 2.04 (2H, m), 2.41 (2H, q), 2.56 (4H, m), 3.15 (4H, m), 4.29 (2H, t), 6.14 (2H, s), 7.05 (1H, d), 7.18 (2H, m), 7.28 (1H, m), 7.60 (1H, m), 7.84 (2H, m), 8.56 (1H, d), 8.68 (1H, d), 8.79 (1H, d), 8.98 (1H, s), 11.01 (1H, s).

LRMS: m/z 615 (M+1)$^+$

EXAMPLE 41

5-[5-(4-Ethylpiperazin-1-ylsulphonyl)-2-n-propoxyphenyl]-3-(pyridin-3-yl)-2-(pyridin-2-yl) methyl-2,6-dihydro-7H-pyrazolo[4,3-d]pyrimidin-7-one Obtained as a solid (50%) from the title compound of Preparation 92, using a similar procedure to that described in Example 38.

Found: C, 60.23; H, 5.57; N, 18.11. $C_{31}H_{34}N_8O_4S$ requires C, 60.57; H, 5.57; N, 18.23%.

δ(CDCl₃): 1.03 (3H, t), 1.20 (3H, t), 2.05 (2H, m), 2.42 (2H, q), 2.59 (4H, m), 3.18 (4H, m), 4.28 (2H, t), 6.05 (2H, s), 7.19 (3H, m), 7.38 (1H, m), 7.63 (1H, m), 7.89 (1H, d), 8.60 (2H, m), 8.71 (1H, d), 8.92 (1H, s), 9.59 (1H, s), 11.01 (1H, s).

EXAMPLE 42

5-[5-(4-Ethylpiperazin-1-ylsulphonyl)-2-(propoxy) pyridin-3-yl]-3(pyridin-3-yl)-2-(pyrimidin-2-yl) methyl-2,6-dihydro7H-pyrazolo[4,3-d]pyrimidin-7-one A mixture of the title compound of Preparation 93 (200 mg, 0.40 mmol) and sodium hydride (17 mg, 60%, 0.43 mmol) in dimethylformamide (5 ml) was stirred at room temperature for 2 hours. The title compound of Preparation 95 (55 mg, 0.43 mmol) was added and the reaction stirred at room temperature for 18 hours, then evaporated under reduced pressure. The residue was purified by column chromatography on silica gel, using an elution gradient of dichloromethane:methanol (97:3 to 85:15) to afford the title compound, (56 mg, 23%).

Found: C, 54.99; H, 5.00; N, 21.96. $C_{28}H_{30}N_{10}O_4S$; $0.25CH_2Cl_2$ requires C, 54.38; H, 4.93; N, 22.45%.

δ(DMSOd₆): 0.95 (3H, t), 1.37 (3H, t), 2.34 (2H, q), 2.44 (4H, m), 3.00 (4H, m), 4.55 (2H, q), 6.12 (2H, s), 7.50 (2H, m), 8.38 (1H, s), 8.56 (2H, m), 8.68 (1H, s), 8.78 (2H, m), 9.42 (1H, s), 12.62 (1H, s).

LRMS: m/z 603 (M+1)$^+$

EXAMPLE 43

5-[2-Ethoxy-5-(4-ethylpiperazin-1-ylsulphonyl) pyridin-3-yl]-3-(4-methoxy-phenyl)-2-methyl-2,6-dihydro-7H-pyrazolo[4,3-d]pyrimidin-7-one Triethylamine (24 ml, 0.17 mmol), tri(o-tolyl)phosphine (7 mg, 0.02 mmol), the title compound of Preparation 101 (48 mg, 0.09 mmol) and finally tris(dibenzylideneacetone) dipalladium(0) (10 mg, 0.01 mmol) were added to a solution of (4-methoxyphenyl)tri-n-butyltin (Tetrahedron, 1993; 49(25); 5461) (181 mg, 0.45 mmol) in acetonitrile (5 ml) and the reaction heated under reflux for 18 hours. The cooled mixture was evaporated under reduced pressure and the residue purified twice by column chromatography on silica gel, using an elution gradient of methanol:ethyl acetate (5:95 to 10:90). This product was triturated with diethyl ether to afford the title compound (22 mg, 43%) as a pale yellow solid.

δ(CDCl$_3$): 1.02 (3H, t), 1.60 (3H, t), 2.40 (2H, q), 2.55 (4H, m), 3.12 (4H, m), 3.92 (3H, s), 4.19 (3H, s), 4.77 (2H, q), 7.08 (2H, d), 7.60 (2H, d), 8.62 (1H, s), 8.98 (1H, s), 10.70 (1H, s).

LRMS: m/z 554 (M+1)$^+$

EXAMPLE 44

5-[2-Ethoxy-5-(4-ethylpiperazin-1-ylsulphonyl)pyridin-3-yl]-2-methyl-3-(4-trifluoromethoxyphenyl)-2,6-dihydro-7H-pyrazolo[4,3-d]pyrimidin-7-one Sodium nitrite (38 mg, 0.55 mmol) was added to a cooled (−10° C.) solution of the title compound of preparation 138 (120 mg, 0.27 mmol) in acetic acid (4 ml) and concentrated hydrochloric acid (4 ml), and the solution stirred at 0° C. for 90 minutes. The solution was re-cooled to −30° C., liquid sulphur dioxide (4 ml) added, followed by a solution of copper (II) chloride (108 mg, 0.80 mmol) in water (5 drops). The reaction mixture was stirred at 0° C. for 30 minutes and at room temperature for an additional 90 minutes. The mixture was then diluted with dichloromethane, and the phases separated. The aqueous phase was extracted with dichloromethane, the combined organic solutions dried (MgSO$_4$), and evaporated under reduced pressure. The residue was azeotroped with toluene to give a yellow solid. A solution of this intermediate sulphonyl chloride in dichloromethane was cooled in ice. Triethylamine (120 μl, 0.86 mmol) and N-ethylpiperazine (70 μl, 0.54 mmol) were added and the reaction stirred at room temperature for 20 hours. The reaction was washed with saturated aqueous sodium bicarbonate solution, and brine, then dried (MgSO$_4$) and concentrated under reduced pressure. The crude product was purified by column chromatography on silica gel using dichloromethane:methanol (95:5) as eluant to afford the title compound, (84 mg, 51%) as a white solid.

δ(CDCl$_3$): 1.02 (3H, t), 1.58 (3H, t), 2.20 (2H, q), 2.54 (4H, m), 3.12 (4H, m), 4.20 (3H, s), 4.78 (2H, q), 7.41 (2H, d), 7.75 (2H, d), 8.62 (1H, s), 8.96 (1H, s), 10.71 (1H, s).

LRMS: m/z 608 (M+1)$^+$

EXAMPLES 45 to 53

The following compounds of the general structure:

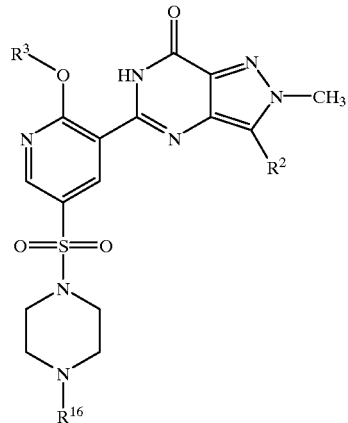

were prepared from the corresponding amino compounds, following a similar procedure to that described in example 44.

| Ex | R$^3$ | R$^2$ | R$^{16}$ | Data |
|----|-------|-------|----------|------|
| 45 | CH$_2$CH$_3$ | 4-fluorophenyl (*) | CH$_2$CH$_3$ | δ (CDCl$_3$) : 1.02 (3H, t), 1.59 (3H, t), 2.40 (2H, q), 2.55 (4H, m), 3.12 (4H, m), 4.20 (3H, s), 4.78 (2H, q), 7.27 (2H, m), 7.64 (2H, m), 8.62 (1H, d), 8.97 (1H, d), 10.71 (1H, s). LRMS : m/z 542 (M + 1)$^+$ |
| 46 | CH$_2$CH$_3$ | 3-chlorophenyl (*) | CH$_3$ | δ (CDCl$_3$) : 1.35 (3H, t), 2.14 (3H, s), 2.37 (4H, m), 2.96 (4H, m), 4.17 (3H, s), 4.50 (2H, q), 7.59 (2H, m), 7.74 (1H, d), 7.86 (1H, s), 8.20 (1H, d), 8.62 (1H, d), 12.05 (1H, s). LRMS : m/z 544, 546 (M + 1)$^+$ |
| 47 | CH$_2$CH$_3$ | 3-chlorophenyl (*) | CH$_2$CH$_3$ | δ (CDCl$_3$) : 1.02 (3H, t), 1.59 (3H, t), 2.40 (2H, q), 2.56 (4H, m), 3.14 (4H, m), 4.22 (3H, s), 4.78 (2H, q), 7.42-7.58 (2H, m), 7.66 (1H, m), 7.77 (1H, s), 8.63 (1H, s), 8.99 (1H, s), 10.78 (1H, s). LRMS : m/z 558, 560 (M + 1)$^+$ |

-continued

| Ex | R³ | R² | R¹⁶ | Data |
|---|---|---|---|---|
| 48 | (CH₂)₂OCH₃ | 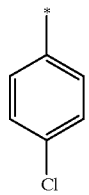 | CH₂CH₃ | δ (DMSOd₆) : 0.93 (3H, t), 2.27 (2H, q), 2.40 (4H, m), 2.96 (4H, m), 3.22 (3H, s), 3.64 (2H, t), 4.15 (3H, s), 4.57 (2H, t), 7.61 (2H, d), 7.78 (2H, d), 8.20 (1H, s), 8.60 (1H, s), 11.95 (1H, s). LRMS : m/z 588, 590 (M + 1)⁺ |
| 49 | CH₂CH₃ | 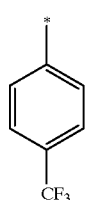 | CH₂CH₃ | δ (CDCl₃) : 1.02 (3H, t), 1.59 (3H, t), 2.40 (2H, q), 2.54 (4H, m), 3.12 (4H, m), 4.23 (3H, s), 4.78 (2H, q), 7.82 (4H, s), 8.64 (1H, s), 8.96 (1H, s), 10.75 (1H, s). LRMS : m/z 592 (M + 1)⁺ |
| 50 | CH₂CH₃ | 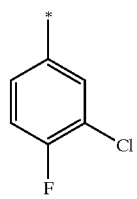 | CH₂CH₃ | δ (CDCl₃) : 1.02 (3H, t), 1.58 (3H, t), 2.40 (2H, q), 2.56 (4H, m), 3.14 (4H, m), 4.20 (3H, s), 4.78 (2H, q), 7.38 (1H, m), 7.56 (1H, m), 7.80 (1H, d), 8.62 (1H, s), 8.98 (1H, s), 10.77 (1H, s). LRMS : m/z 576, 578 (M + 1)⁺ |
| 51 | CH₂CH₃ | 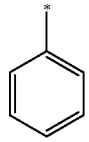 | CH₂CH₃ | δ (CDCl₃) : 1.02 (3H, t), 1.59 (3H, t), 2.40 (2H, q), 2.54 (4H, 4.20 (3H, s), 4.78 (2H, q), 7.50–7.59 (3H, m), 7.66 (2H, d), 8.61 (1H, d), 8.98 (1H, d), 10.71 (1H, s). LRMS : m/z 524 (M + 1)⁺ |
| 52 | (CH₂)₂OCH₃ | 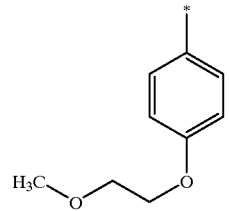 | CH₂CH₃ | δ (CDCl₃) : 1.01 (3H, t), 2.40 (2H, q), 2.52 (4H, m), 3.09 (4H, m), 3.45 (3H, s), 3.58 (3H, s), 3.80 (2H, t), 3.84 (2H, t), 4.17 (3H, s), 4.20 (2H, t), 4.78 (2H, t), 7.11 (2H, d), 7.59 (2H, d), 8.60 (1H, d), 8.90 (1H, s), 10.83 (1H, s). LRMS : m/z 628 (M + 1)⁺ |
| 53 | CH₂CH₃ | 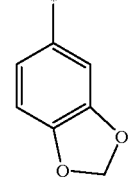 | CH₂CH₃ | δ (CDCl₃) : 1.01 (3H, t), 1.58 (3H, t), 2.40 (2H, q), 2.54 (4H, m), 3.15 (4H, m), 4.18 (3H, s), 4.77 (2H, q), 6.08 (2H, s), 6.99 (1H, d), 7.10 (1H, d), 7.18 (1H, s), 8.62 (1H, d), 8.99 (1H, d), 10.69 (1H, s). LRMS : m/z 568 (M + 1)⁺ |

EXAMPLE 54

5-[2-Ethoxy-5-(4-ethylpiperazin-1-ylsulphonyl) pyridin-3-yl]-3-(2-methoxyphenyl)-2-methyl-2,6-dihydro-7H-pyrazolo[4,3-d]pyrimidin-7-one A mixture of the title compound of preparation 101 (50 mg, 0.95 mmol), 2-methoxybenzene boronic acid (19 mg, 0.125 mmol), cesium fluoride (37.5 mg, 0.247 mmol), tri(o-tolyl)phosphine (3 mg, 0.001 mmol) and tris (dibenzylideneacetone)palladium (0) (5 mg, 0.005 mmol) in 1,2-dimethoxyethane (1 ml) was heated under reflux for 18 hours. Tlc analysis showed starting material remaining, so additional tris(dibenzylideneacetone)palladium (0) (5 mg, 0.005 mmol), tri(o-tolyl)phosphine (9 mg, 0.003 mmol) and cesium fluoride (9 mg, 0.059 mmol) were added, and the reaction heated for a further 72 hours under reflux. The cooled reaction mixture was evaporated under reduced pressure. The residue was purified by column chromatography on silica gel using diethylamine:ethyl acetate (95:5) as eluant, and repeated using ethyl acetate as eluant. The product was triturated with diethyl ether to afford the title compound, (6 mg, 11%) as a solid.

δ(CDCl₃): 1.02 (3H, t), 1.58 (3H, m), 2.40 (2H, q), 2.50 (4H, m), 3.08 (4H, m), 3.86 (3H, s), 4.02 (3H, s), 4.76 (2H, q), 7.14 (2H, m), 7.41 (1H, d), 7.54 (1H, m), 8.60 (1H, d), 8.94 (1H, d), 10.64 (1H, s).

LRMS: m/z 554 (M+1)$^+$

EXAMPLE 55

3-(4-Cyanophenyl)-5-[5-(4-ethylpiperazin-1-ylsulphonyl)-2-(2-methoxyethoxy)pyridin-3-yl]-2-methyl-2,6-dihydro-7H-pyrazolo[4,3-d]pyrimidin-7one A mixture of the title compound of preparation 122 (100 mg, 0.18 mmol), potassium carbonate (50 mg, 0.36 mmol), and 4-cyanophenylboronic acid (32 mg, 0.22 mmol) in dioxan (5 ml) and water (1 ml) was de-gassed and placed under a nitrogen atmosphere. Tetrakis(triphenylphosphine)-palladium (0) (20 mg, 0.017 mmol) was added and the reaction heated under reflux for 2 hours. The cooled reaction mixture was concentrated under reduced pressure and the residue partitioned between water and dichloromethane. The layers were separated, the aqueous phase extracted with dichloromethae (2×), and the combined organic extracts dried (MgSO$_4$) and evaporated under reduced pressure. The residue was purified by medium pressure column chromatography on silica gel using an elution gradient of dichloromethane:methanol (99:1 to 98:2) to afford the title compound, (27 mg, 26%) as a white solid.

δ(CDCl$_3$): 1.02 (3H, t), 2.41 (2H, q), 2.56 (4H, m), 3.12 (4H, m), 3.58 (3H, s), 3.84 (2H, t), 4.22 (3H, s), 4.79 (2H, t), 7.83 (4H, m), 8.62 (1H, d), 8.9,6 (1H, d), 10.96 (1H, s).

LRMS: m/z 579 (M+1)$^+$

EXAMPLE 56

5-[5-(4-Ethylpiperazin-1-ylsulphonyl)-2(2-methoxyethoxy)pyridin-3-yl]-2-methyl-3-(pyridin-3-yl)-2,6-dihydro-7H-pyrazolo[4,3-d]pyrimidin-7one A mixture of the title compound of preparation 122 (152 mg, 0.27 mmol), 3-pyridyl boronic acid hydrochloride (56 mg, 0.35 mmol), and potassium carbonate (113 mg, 0.82 mmol) in dioxan (4 ml) and water (1 ml) was degassed and placed under an atmosphere of nitrogen. Tetrakis (triphenylphosphine)palladium (0) (31 mg, 0.027 mmol) was added and the reaction heated under reflux for 90 minutes. The cooled reaction mixture was concentrated under reduced pressure and the residue partitioned between ethyl acetate and water. The resulting suspension was filtered through Celite®, and the filtrate separated. The organic layer was washed with aqueous sodium bicarbonate solution, then brine, dried (MgSO$_4$) and evaporated under reduced pressure. The residue was triturated with a small volume of ethyl acetate, the solid filtered and dried to afford the title compound, (101 mg, 67%) as a light brown solid.

δ(CDCl$_3$): 1.02 (3H, t), 2.40 (2H, q), 2.54 (4H, m), 3.10 (4H, m), 3.59 (3H, s), 3.85 (2H, t), 4.20 (3H, s), 4.79 (2H, t), 7.52 (1H, m), 8.01 (1H, m), 8.82 (1H, m), 8.76 (1H, d), 8.90 (2H, m), 10.94 (1H, s).

LRMS: m/z 555 (M+1)$^+$

EXAMPLE 57

3-(6Aminopyridin-3-yl)-5-[2-ethoxy-5-(4-ethylpiperazin-1-ylsulphonyl)pyridin-3-yl]-2-methyl-2,6-dihydro-7H-pyrazolo[4,3-d]pyrimidin-7one n-Butyllithium (3.5 ml, 1.6M in hexanes, 5.6 mmol) was added dropwise to a cooled (−78° C.) solution of the title compound of preparation 143 (500 mg, 2.27 mmol) in tetrahydrofuran (5 ml), and the solution stirred for 30 minutes. Triisopropyl borate (0.79 ml, 3.29 mmol) was added dropwise and the mixture allowed to warm to room temperature over 3 hours. The reaction was quenched by the addition of hydrochloric acid (2N), then evaporated under reduced pressure to give a yellow solid, 1.2 g. A mixture of the title compound of preparation 101 (100 mg, 0.19 mmol), the intermediate boronic acid hydrochloride (120 mg), potassium carbonate (104 mg, 0.75 mmol), and tetrakis (triphenylphosphine)palladium (0) (20 mg, 0.017 mmol) in dioxan (5 ml) and water (1 ml) was heated under reflux for 3 hours. Tlc analysis showed starting material remaining, so additional boronic acid (120 mg), potassium carbonate (104 mg, 0.75 mmol) and tetrakis(triphenylphosphine)palladium (0) (20 mg, 0.017 mmol) were added, and the reaction heated under reflux for a further 18 hours. The cooled reaction mixture was concentrated under reduced pressure and the residue partitioned between water and dichloromethane. The phases were separated, the organic layer washed with brine, dried (MgSO$_4$) and evaporated under reduced pressure. The crude product was purified by medium pressure column chromatography on silica gel using dichloromethane:methanol (95:5) as eluant to afford the title compound, (17 mg, 17%) as a yellow solid.

δ(CDCl$_3$): 1.02 (3H, t), 1.59 (3H, t), 2.40 (2H, q), 2.56 (4H, m), 3.12 (4H, m), 4.18 (3H, s), 4.76 (4H, m), 6.68 (1H, d), 7.78 (1H, dd), 8.35 (1H, d), 8.61 (1H, d), 8.98 (1H, d), 10.71 (1H, s).

LRMS: m/z 540 (M+1)$^+$

EXAMPLE 58

5-[2-Ethoxy-5-(4-ethylpiperazin-1-ylsulphonyl) pyridin-3-yl]-2-methyl-3-[6-(methylamino)pyridin-3-yl]-2,6-dihydro-7H-pyrazolo[4,3-d]pyrimidin-7-one A mixture of the title compounds of preparations 101 (100 mg, 0.19 mmol) and 147 (75 mg, 0.40 mmol), potassium carbonate (104 mg, 0.75 mmol), and tetrakis (triphenylphosphine)palladium (0) (20 mg, 0.017 mmol) in dioxan (5 ml) and water (1 ml) was heated under reflux for 4 hours. Tlc analysis showed starting material remaining, so additional boronic acid (75 mg, 0.40 mmol), tetrakis (triphenylphosphine)palladium (0) (20 mg, 0.017 mmol) and potassium carbonate (50 mg, 0.36 mmol) were added and the reaction continued for a flier 2 hours. The cooled mixture was concentrated under reduced pressure, and the residue partitioned between water and dichloromethane and the phases separated. The aqueous layer was extracted with dichloromethane and the combined organic solutions washed with brine, dried (MgSO$_4$) and evaporated under reduced pressure. The residue was triturated with diethyl ether, and the resulting solid, filtered and dried. The crude product was purified by medium pressure column chromatography using an elution gradient of dichloromethane:methanol (99:1 to 97:3) and triturated with diethyl ether to afford the title compound, (63 mg, 60%) as a yellow solid.

δ(CDCl$_3$): 1.01 (3H, t), 1.58 (3H, t), 2.40 (2H, q), 2.54 (4H, m), 3.02 (3H, d), 3.10 (4H, m), 4.18 (3H, s), 4.76 (2H, q), 4.80 (1H, m), 6.58 (1H, d), 7.78 (1H, d), 8.37 (1H, s), 8.60 (1H, s), 8.98 (1H, s), 10.70 (1H, s).

LRMS: m/z 554 (M+1)$^+$

EXAMPLE 59

3-(6-Dimethylaminoipyridin-3-yl)-5-[5-(4-ethiylpiperazin-1-ylsulphonyl)-2-(2-methoxyethoxy) pyridin-3-yl]-2-methyl-2,6-dihydro-7H-pyrazolo[4,3-d]pyrimidin-7-one The title compound was obtained as a yellow solid (66%), from the title compounds of 122 and 148, following the procedure described in example 55.

δ(CDCl$_3$): 1.01 (3H, t), 2.40 (2H, q), 2.54 (4H, m), 3.12 (4H, m), 3.19 (6H, s), 3.58 (3H, s), 3.84 (2H, t), 4.18 (3H, s), 4.78 (2H, t), 6.66 (1H, d), 7.78 (1H, d), 8.41 (1H, s), 8.60 (1H, s), 8.90 (1H, s), 10.83 (1H, s).

LRMS: m/z 598 (M+1)$^+$

EXAMPLE 60

3-[6-(Azetidin-1-yl)pyridin-3-yl]-5-[5-(4-ethylpiperazin-1-ylsulphonyl)-2-(2-methoxyethoxy) pyridin-3-yl]-2-methyl-2,6-dihydro-7H-pyrazolo[4,3-d]pyrimidin-7-one n-Butyllithium (3.0 ml, 1.6M in hexanes, 4.8 mmol) was added dropwise to a cooled (−70° C.) solution of the title compound of preparation 144 (900 mg, 4.22 mmol) in tetrahydrofuran (10 ml), and the solution stirred for 30 minutes. A solution of triisopropyl borate (1.46 ml, 6.33 mmol) in tetrahydrofuran (4 ml) was added dropwise, and the reaction then allowed to warm to room temperature over 3 hours. The reaction was quenched by the addition of hydrochloric acid (2N), and the mixture then evaporated under reduced pressure. A mixture of the title compound of preparation 122 (65 mg, 0.117 mmol), potassium carbonate (65 mg, 0.47 mmol), the intermediate boronic acid (50 mg), and tetrakis(triphenylphosphine)palladium (0) (15 mg, 0.013 mmol) in dioxan (5 ml) and water (1.5 ml) was heated under reflux for 2 hours. Tlc analysis showed starting material remaing, so additional crude boronic acid (50 mg) and tetrakis(triphenylphosphine)palladium (0) (15 mg, 0.013 mmol) were added and the reaction continued for a furter 3 hours. The cooled mixture was concentrated under reduced pressure, and the residue partitioned between water and dichloromethane and the phases separated. The aqueous layer was extracted with dichloromethane and the combined organic solutions washed with brine, dried (MgSO$_4$) and evaporated under reduced pressure. The crude product was purified by medium pressure column chromatography on silica gel using an elution gradient of dichloromethane:methanol (99:1 to 97:3), then triturated several times with diethyl ether to afford the title compound, (22 mg, 31%) as a solid.

δ(CDCl$_3$): 1.01 (3H, t), 2.40 (2H, q), 2.46 (2H, m), 2.54 (4H, m), 3.10 (4H, m), 3.58 (3H, s), 3.86 (2H, t), 4.16 (7H, m), 4.78 (2H, t) 6.40 (1H, d), 7.78 (1H, dd), 8.38 (1H, d), 8.60 (1H, d), 8.92 (1H, d), 10.82 (1H, s).

LRMS: m/z 610 (M+1)$^+$

EXAMPLE 61

5-[2-Ethoxy-5-(4-ethylpiperazin-1-ylsulphonyl) pyridin-3-yl]-3-(furan-2-yl)-2-methyl-2,6-dihydro7H-pyrazolo[4,3-d]pyrimidin-7-one The title compound was prepared from the title compound of preparation 101 and furan-2-boronic acid, following a similar procedure to that described in example 56. The crude product was purified by column chromatography on silica gel using dichloromethane:methanol (100:0 to 97:3) as eluant, to afford the desired compound, (100 mg, 68%).

δ(CDCl$_3$): 1.01 (3H, t), 1.58 (3H, t), 2.40 (2H, q), 2.57 (4H, m), 3.16 (4H, m), 4.40 (3H, s), 4.78 (2H, q), 6.66 (1H, m), 7.28 (1H, m), 7.64 (1H, s), 8.63 (1H, d), 9.09 (1H, d), 10.75 (1H, s).

LRMS: m/z 514 (M+1)$^+$

EXAMPLE 62

5-[2-Ethoxy-5-(4-ethylpiperazin-1-ylsulphonyl) pyridin-3-yl]-3-(furan-3-yl)-2-methyl-2,6-dihydro-7H-pyrazolo[4,3-d]pyrimidin-7-one The title compound was prepared from the title compound of preparation 101 and furan-3-boronic acid, following a similar procedure to that described in example 56. The crude product was purified by reverse phase column chromatography on polystyrene gel, using an elution gradient of 0.1% aqueous trifluoroacetic acid:acetonitrile (90:10 to 20:80), to afford the title compound (9.8 mg, 10%).

δ(CDCl$_3$): 1.02 (3H, t), 1.59 (3H, t), 2.40 (2H, q), 2.57 (4H, m), 3.16 (4H, m), 4.24 (3H, s), 4.77 (2H, q), 7.05 (1H, s), 7.62 (1H,s), 8.03 (1H, s), 8.62 (1H, d), 9.02 (1H, d), 10.71 (1H, s).

LRMS: m/z 514 (M 1)$^+$

EXAMPLE 63

5-[2-Ethoxy-5-(4-ethylpiperazin-1-ylsuphonyl) pyridin-3-yl]-3-(3-methoxyphenyl)-2-methyl-2,6-dihydro-7H-pyrazolo[4,3-d]pyrimidin-7-one Tris(dibenzylideneacetone)palladium (0) (9 mg, 0.009 mmol) was added to a mixture of the title compounds of preparation 101 (44 mg, 0.083 mmol), and 3-methoxyphenyl tri-n-butylstannane (75 mg, 0.19 mmol), tri(o-tolyl) phosphine (7 mg, 0.023 mmol) and triethylamine (21 μl, 0.15 mmol) in acetonitrile (2 ml) and the reaction mixture heated under reflux for 18 hours. Tlc analysis showed starting material remaining, so additional stannane (90 mg, 0.23 mmol), tri(o-tolyl)phosphine (7 mg, 0.023 mmol), tris(dibenzylideneacetone)palladium (0) (9 mg, 0.009 mmol) and triethylamine (21 μl, 0.15 ml) were added, and the reaction heated under reflux for a further 72 hours. The cooled mixture was purified directly by column chromatography on silica gel using ethyl acetate:methanol (95:5) as eluant. The crude product was triturated with diethyl ether to afford the title compound, (5 mg, 11%) as a solid.

δ(CDCl$_3$): 1.00 (3H, t), 1.58 (3H, t), 2.40 (2H, q), 2.53 (4H, m), 3.10 (4H, m), 3.92 (3H, s), 4.22 (3H, s), 4.78 (2H, q), 7.04 (1H, m), 7.20 (1H, d), 7.34 (1H, s), 7.47 (1H, m), 8.62 (1H, s), 9.00 (1H, s), 10.76 (1H, s).

LRMS: m/z 554 (M+1)$^+$

EXAMPLE 64

5-[5-(4-Ethylpiperazin-1-ylsulphonyl)-2-(2-methoxyethoxy)pyridin-3-yl]-3-(5-methylpyridin-2-yl)-2-methyl-2,6-dihydro-7H-pyrazolo[4,3-d] pyrimidin-7-one Tetrakis(triphenylphosphine)palladium (0) (31 mg, 0.027 mmol) was added to a mixture of the title compounds of preparations 122 (150 mg, 0.27 mmol), and 149 (154 mg, 0.40 mmol), lithium chloride (113 mg, 2.69 mmol) and copper (1) iodide (8 mg, 0.04 mmol) in dioxan (6 ml) and the reaction heated under reflux under nitrogen for 18 hours. The cooled reaction was partitioned between water and ethyl acetate, the layers separated, and the organic phase dried (MgSO$_4$), and evaporated under reduced pressure. The residue was purified by column chromatography on silica gel using dichloromethane:methanol (95:5) as eluant and triturated with an diethyl ether:isopropyl alcohol solution (50:50) to afford is the title compound, (92 mg, 60%) as a yellow solid.

δ(CDCl$_3$): 1.02 (3H, t), 2.40 (5H, m), 2.56 (4H, m), 3.16 (4H, m), 3.60 (3H, s), 3.88 (2H, t), 4.56 (3H, s), 4.80 (2H, t), 7.65 (1H, s), 8.36 (1H, d), 8.59 (1H, s), 8.63 (1H, s), 9.00 (1H, s), 10.90 (1H, s).

LRMS: m/z 569 (M+1)$^+$

Found: C, 52.59; H, 5.43; N, 18.82. C$_2$H$_{32}$N$_8$O$_5$S:1.5H$_2$O requires, 52.48; H, 5.92; N, 18.81%.

EXAMPLE 65

5-[5-(4-Ethylpiperazin-1-ylsulphonyl)-2-(2-methoxyethoxy)pyridin-3-yl]-3-(6-ethylpyridin-3-yl)-2-methyl-2,6-dihydro7H-pyrazolo[4,3-d] pyrimidin-7-one The title compound was obtained (57%), after crystallistion from isopropyl alcohol, as a white powder, from the title compounds of preparations 122 and 150, following a similar procedure to that described in example 64.

δ(CDCl$_3$): 1.02 (3H, t), 1.40 (3H, t), 2.40 (2H, q), 2.55 (4H, m), 2.97 (2H, q), 3.12 (4H, m), 3.59 (3H, s), 3.86 (2H, t), 4.20 (3H, s), 4.80 (2H, t), 7.40 (1H, d), 7.96 (1H, d), 8.61 (1H, s), 8.80 (1H, s), 8.88 (1H, s), 10.91 (1H, s).

LRMS: m/z 583 (M+1)$^+$

Found: C, 54.40; H, 5.91; N, 18.78. C$_{27}$H$_{34}$N$_8$O$_5$S;0.5H$_2$O requires C, 54.81; H, 5.96; N, 18.94%.

EXAMPLE 66

3-(2-Aminopyrimidin-5-yl)-5-[2-ethoxy-5-(4-ethylpiperazin-1-ylsulphonyl)pyridin-3-yl]-2methyl-2,6-dihydro-7H-pyrazolo[4,3-d]pyrimidin-7-one The title compound was prepared from the title compounds of preparations 101 and 153, following a similar procedure to that described in example 64. The crude product was purified by column chromatography on silica gel using an elution gradient of dichloromethane:methanol:acetic acid (100:0:0 to 95:5:0 to 90:10:1) to give the desired product (30 mg, 21%) as a yellow solid.

δ(CDCl$_3$): 1.02 (3H, t), 1.58 (3H, t), 2.43 (2H, q), 2.59 (4H, m), 3.16 (4H, m), 3.28–3.72 (2H, br, s), 4.18 (3H, s), 4.77 (2H, q), 8.58 (2H, s), 8.62 (1H, s), 8.92 (1H, d), 10.84 (1H, s).

EXAMPLE 67

3-(2-Dimethylamino-pyrimidin-5-yl)-5-[5-4thylpiperazin-1-ylsulphonyl)-2-(2-methoxyethoxy)pyridin-3-yl]-2-methyl-2,6-dihydro-7H-pyrazolo[4,3-d]pyrimidin-7-one A mixture of the title compounds of preparations 122 (100 mg, 0.18 mmol) and 148 (77 mg, 0.27 mmol), copper (I) iodide (5 mg, 0.027 mmol), and lithium chloride (76 mg, 1.8 mmol) in dioxan (5 ml) was de-gassed, and placed under an atmosphere of nitrogen. Tetrakis(triphenylphosphine)palladium (0) (20 mg, 0.017 mmol) was added and the reaction mixture heated under reflux for 5½ hours. Tlc analysis showed no stannane remaining, so additional tetrakis(triphenylphosphine)palladium (0) (20 mg, 0.017 mmol), copper (I) iodide (5 mg, 0.027 mmol) and the title compound of preparation 148 (25 mg, 0.087 mmol) were added, and the reaction heated for a further is hour under reflux. The cooled reaction was diluted with aqueous 10% potassium fluoride solution (5 ml), the mixture stirred for 20 minutes, then filtered through Celite® washing through well with dichloromethane. The filtrate was separated, the aqueous layer extracted with dichloromethane, and the combined organic solutions dried (MgSO$_4$) and evaporated under reduced pressure. The residue was purified by column chromatography on silica gel using an elution gradient of dichloromethane:methanol (100:0 to 97:3) to give a gum. This was crystallised from isopropyl alcohol, the solid filtered and triturated with pentane to afford the title compound, (66 mg, 61%) as a solid.

δ(CDCl$_3$): 1.03 (3H, t), 2.41 (2H, q), 2.57 (4H, m), 3.16 (4H, m), 3.30 (6H, s), 3.58 (3H, s), 3.88 (2H, t), 4.18 (3H, s), 4.79 (2H, t), 8.60 (2H, s), 8.62 (1H, d), 8.92 (1H, d), 10.86 (1H, s).

LRMS: m/z 599 (M+1)$^+$

EXAMPLE 68

5-[5-(4-Ethylpiperazin-1-ylsulphonyl)-2-(2-methoxyethoxy)pyridin-3-yl]-3-(6-methoxypyridin-3-yl)-2,6-dihydro-7H-pyrazolo[4,3-d]pyrimidin-7-one The title compound was prepared from the title compound of preparation 122 and 2-methoxy-5-(tri-n-butylstannyl) pyridine, following a similar procedure to that described in example 67. The crude product was purified by medium pressure column chromatography on silica gel using dichloromethane:methanol (97:3) as eluant, and triturated with diethyl ether to afford the desired compound, (12.6 mg, 12%) as a yellow solid.

δ(CDCl$_3$): 1.02 (3H, t), 2.40 (2H, q), 2.55 (4H, m), 3.10 (4H, m), 3.58 (3H, s), 3.85 (3H, s), 3.84 (2H, t), 4.02 (3H, s), 4.18 (3H, s), 4.78 (2H, q), 6.95 (1H, d), 7.88 (1H, dd), 8.43 (1H, s), 8.61 (1H, d), 8.90 (1H, d), 10.88 (1H, s).

LRMS: m/z 585 (M+1)$^+$

EXAMPLE 69

5-[2-Ethoxy-5-(4-ethylpiperazin-1-ylsulphonyl)pyridin-3-yl]-2-methyl-3-(pyrazin-2-yl)-2,6-dihydro-7H-pyrazolo[4,3-d]pyrimidin-7-one The title compound was obtained (70%) from the title compounds of preparations 101 and 151, following a similar procedure to that described in example 68.

δ(CDCl$_3$): 1.02 (3H, t), 1.60 (3H, t), 2.41 (2H, q), 2.58 (4H, m), 3.19 (4H, m), 4.56 (3H, s), 4.78 (2H, q), 8.58 (1H, d), 8.68 (2H, s), 9.07 (1H, d), 9.74 (1H, s), 10.78 (1H, s).

LRMS: m/z 526 (M+1)$^+$

EXAMPLE 70

3-(2-Chloropyrimidin-5-yl)-5-[2-ethoxy-5-(4-ethylpiperazin-1-ylsulphonyl)pyridin-3-yl]-2-methyl-2,6-dihydro-7H-pyrazolo[4,3-d]pyrimidin-7-one A mixture of the title compounds from preparations 101 (150 mg, 0.285 mmol) and 152 (142 mg, 0.43 mmol), copper (I) iodide (8 mg, 0.042 mmol), and lithium chloride (120 mg, 2.85 mmol) in dioxan (10 ml) was de-gassed, and placed under an atmosphere of nitrogen. Tetrakis (triphenylphosphine)palladium (0) (33 mg, 0.029 mmol) was added and the reaction mixture heated under reflux for 6 hours. Tlc analysis showed no stannane remaining, so additional tetrakis(triphenylphosphine)palladium (0) (33 mg, 0.029 mmol), and stannane (143 mg, 0.43 mmol) were added, and the reaction heated for a further 18 hours under reflux. Further tetrakis(triphenylphosphine)palladium (0)(33 mg, 0.029 mmol), and stannane (143 mg, 0.43 mmol) were added, and the reaction heated for an additional 12 hours. The cooled mixture was partitioned between dichloromethane and brine, the layers separated and the organic phase dried (MgSO$_4$) and evaporated under reduced pressure. The residue was purified by column chromatography on silica gel using dichloromethane as eluant. The crude product was furter purified by HPLC using a reverse phase silica gel column, and an elution gradient of 0.1% aqueous trifluoroacetic acid:acetonitrile (90:10 to 20:80). The combined column fractions were basified to pH 8 using sodium carbonate, and the mixture extracted with dichloromethane. The combined organic solutions were dried (MgSO$_4$) and evaporated under reduced pressure to afford the title compound, 22 mg, 14%.

δ(CDCl$_3$): 1.10 (3H, m), 1.58 (3H, m), 2.41–2.71 (6H, m), 3.18 (4H, m), 4.26 (3H, s), 4.78 (2H, q), 8.68 (1H, d), 8.96 (1H, d), 9.02 (2H, s), 10.81 (1H, s).

LRMS: m/z 560 (M+1)$^+$

EXAMPLE 71

5-[5-(4-Ethylpiperazin-1-ylsulphonyl)-2-(2-methoxyethoxy)pyridin-3-yl]-3-(3-imidazo[1,2-a]pyridin-6-yl)-2-methyl-2,6-dihydro-7H-pyrazolo[4,3-d]pyrimidin-7-one trifluoroacethate The title compound was prepared from the title compounds of preparations 122 and 154, following a similar procedure to that described in example 66. The product was farther purified by HPLC using a reverse phase silica gel column, and an elution gradient of 0.1% aqueous trifluoroacetic acid:acetonitrile (98:2 to 70:30) to afford the title compound (16 mg, 8.4%) as a white solid.

δ(CDCl$_3$): 1.40 (3H, t), 2.20 (6H, m), 2.98 (2H, m), 3.16 (2H, q), 3.59 (3H, s), 3.72 (2H, m), 3.96 (2H, t), 4.30 (3H, s), 4.80 (2H, t), 7.99 (1H, d), 8.17 (1H, m), 8.64 (1H, d), 8.77 (1H, d), 9.00 (1H, s), 1.08 (1H, s).

LRMS: m/z 594 (M+1)$^+$

EXAMPLE 72

5-[2-Ethoxy-5-(4-ethylpiperazin-1-ylsulphonyl) pyridin-3-yl]-3-(1ethyl-pyrazolo-4-yl)-2-methyl-2,6-dihydro-7H-pyrazolo[4,3-d]pyrimidin-7-one The title compound was prepared from the title compounds of preparations 101 and 155, following a similar procedure to that described in example 70. The crude product was triturated with an diethyl ether:methanol (95:5) solution, the resulting solid filtered, and recrystallised from isopropyl alcohol to afford the desired compound, (73 mg, 47%) as a yellow solid.

δ(CDCl$_3$): 1.00 (3H, t), 1.58 (6H, m), 2.40 (2H, q), 2.56 (4H, m), 3.14 (4H, m), 4.25 (3H, s), 4.34 (2H, q), 4.78 (2H, q), 7.99 (1H, s), 8.18 (1H, s), 8.63 (1H, d), 9.04 (1H, d), 10.70 (1H, s).

LRMS: m/z 542 (M+1)$^+$

EXAMPLE 73

5-[5-(4-Ethylpiperazin-1-ylsulphonyl)-2-(methoxyethoxy)pyridin-3-yl]-3-(1-ethylpyrazol4-yl)-2-methyl-2,6-dihydro-7H-pyrazolo[4,3-d]pyrimidin-7-one Potassium bis(trimethylsilyl)amide (59 mg, 0.295 mmol) was added to a suspension of the title compound of example 72 (40 mg, 0.073 mmol) in 2-methoxyethanol (6 ml), and the reaction heated under reflux for 18 hours. The cooled mixture was evaporated under reduced pressure and the residue purified by column chromatography on silica gel using dichloromethane:methanol (95:5) as eluant. The product was recrystallised from isopropyl alcohol to afford the title compound, (22 mg, 53%) as a yellow solid.

δ(CDCl$_3$): 1.01 (3H, t), 1.60 (3H, t), 2.41 (2H, m), 2.58 (4H, m), 3.15 (4H, m), 3.58 (3H, s), 3.86 (2H, t), 4.22 (3H, s), 4.30 (2H, q), 4.78 (2H, t), 7.98 (1H, s), 8.17 (1H, s), 8.61 (1H, d), 8.99 (1H, d), 10.76 (1H, s).

LRMS: m/z 572 (M+1)$^+$

EXAMPLE 74

5-[5-(4-Ethylpiperazin-1-ylsulphonyl)-2-(2-methoxyethoxy)pyridin-3-yl]-2-methyl-3-phenyl-2,6-dihydro-7H-pyrazolo[4,3-d]pyrimidin-7-one Potassium bis(trimethylsilyl)amide (115 mg, 0.58 mmol) was added to a solution of the title compound from example 51 (76 mg, 0.145 mmol) in 2-methoxyethanol (3 ml), and the reaction heated at 120° C. for 3 hours under a nitrogen atmosphere. The cooled mixture was neutralised using hydrochloric acid (1N), and concentrated under reduced pressure. The residue was partitioned between dichloromethane and aqueous sodium bicarbonate solution, and the layers separated. The organic phase was washed with additional aqueous sodium bicarbonate solution, and brine, then dried (MgSO$_4$) and evaporated under reduced pressure. The crude product was purified by column chromatography on silica gel using an elution gradient of dichloromethane:methanol (100:0 to 97:3) to afford the title compound (66 mg, 82%).

δ(CDCl$_3$): 1.01 (3H, t), 2.40 (2H, q), 2.52 (4H, m), 3.10 (4H, m), 3.58 (3H, s), 3.85 (2H, t), 4.20 (3H, s), 4.78 (2H, t), 7.48–7.59 (3H, m), 7.65 (2H, m), 8.61 (1H, d), 8.92 (1H, d), 10.88 (1H, s).

LRMS: m/z 554 (M+1)$^+$

EXAMPLES 75 to 77

The following compounds of the general structure:

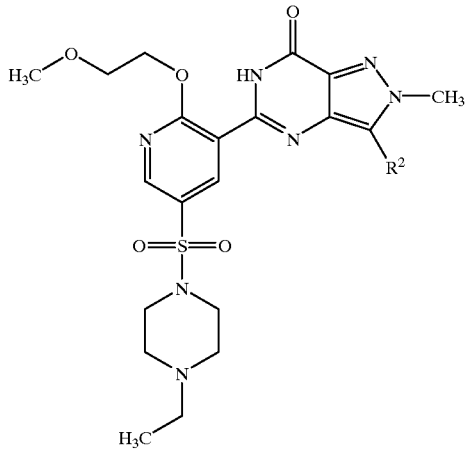

were prepared from the corresponding pyrazolo[4,3-d] pyrimidin-7-one, following a similar procedure to that described in example 74.

| Example | R$^2$ | Data |
|---|---|---|
| 75[1] | * ⌬-Cl (3-chlorophenyl) | δ (DMSOd$_6$) : 0.94 (3H, t), 2.30 (2H, q), 2.40 (4H, m), 2.97 (4H, m), 3.22 (3H, s), 3.68 (2H, t), 4.18 (3H, s), 4.58 (2H, t), 7.59 (2H, m), 7.75 (1H, m), 7.86 (1H, s), 8.24 (1H, d), 8.62 (1H, d), 12.00 (1H, s). LRMS : m/z 588, 590 (M + 1)$^+$ |

| Example | R² | Data |
|---|---|---|
| 76 | 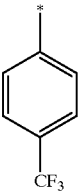 | δ (CDCl₃) : 1.01 (3H, t), 2.40 (2H, q), 2.52 (4H, m), 3.12 (4H, m), 3.58 (3H, s), 3.85 (2H, t), 4.21 (3H, s), 4.79 (2H, t), 7.81 (4H, s), 8.62 (1H, d), 8.88 (1H, d), 10.91 (1H, s). LRMS : m/z 622 (M + 1)⁺ |
| 77 | 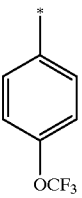 | δ (CDCl₃) : 1.03 (3H, t), 2.40 (2H, q), 2.55 (4H, m), 3.12 (4H, m), 3.59 (3H, s), 3.87 (2H, t), 4.20 (3H, s), 4.79 (2H, t), 7.40 (2H, d), 7.74 (2H, d), 8.62 (1H, s), 8.96 (IH, s), 10.89 (1H, s). LRMS : m/z 638 (M + 1)⁺ |

¹=reaction heated under reflux for 18 hours.

EXAMPLE 78

5-[2-Ethoxy-5-(4-ethylpiperazin-1-ylsulphonyl) pyridin-3-yl]-2-methyl-3-(5-methyl-1,3,4-oxadiazol-2-yl)-2,6-dihydro-7H-pyrazolo[4,3-d]pyrimidin-7-one Acetic hydrazide (80 mg, 1.08 mmol), followed by triethylamine (0.34 ml, 2.44 mmol) were added to a suspension of the title compound of preparation 158 (500 mg, 0.98 mmol) in dichloromethane (15 ml), and the reaction stirred at room temperature for 4 hours. The reaction mixture was partitioned between dichloromethane and aqueous sodium bicarbonate solution, and the layers separated. The aqueous phase was extracted with dichloromethane, and the combined organic solutions dried (Na₂SO₄) and evaporated under reduced pressure, to give a solid, 520 mg. Thionyl chloride (5 ml) was added to this intermediate hydrazide (350 mg), and the solution stirred at 80° C. for 3 hours. The cooled reaction was partitioned between dichloromethane and aqueous sodium bicarbonate solution, and the layers separated. The organic phase was dried (Na₂SO₄) and concentrated under reduced pressure. The residue was purified by column chromatography on silica gel using an elution gradient of dichloromethane:methanol (99:1 to 94:6) to give the title compound, 55 mg.

δ(CDCl₃): 1.01 (3H, t), 1.60 (3H, t), 2.41 (2H, q), 2.58 (4H, m), 2.75 (3H, s), 3.17 (4H, m), 4.58 (3H, s), 4.80 (2H, q), 8.69 (1H, s), 9.19 (1H, s), 10.88 (1H, s).

EXAMPLE 79

5-[2-Ethoxy-5-(4-ethylpiperazin-1-ylsulphonyl)-pyridin-3-yl]-2-methyl-3-(tetrahydrofuran-2-yl)-2,6-dihydro-7H-pyrazolo[4,3-d]pyrimidin-7-one A mixture of the title compound from example 61 (80 mg, 0.16 mmol) and 10% palladium on charcoal (10 mg) in ethanol (4.5 ml) and water (0.5 ml) was hydrogenated at 60 psi (414 kPa) and 40° C. for 18 hours. The reaction mixture was filtered through Celite®, and the filtrate evaporated under reduced pressure to afford the title compound, (27 mg, 32%).

δ(CDCl₃): 1.01 (3H, t), 1.59 (3H, t), 2.15 (1H, m), 2.26 (1H, m), 2.40 (3H, m), 2.56 (4H, m), 2.86 (1H, m), 3.14 (4H, m), 3.98 (1H, m), 4.02 (1H, m), 4.20 (3H, s), 4.77 (2H, q), 5.36 (1H, m), 8.62 (1H, d), 9.00 (1H, d), 10.68 (1H, s).

LRMS: m/z 518 (M+1)⁺

EXAMPLE 80

3-Ethoxy-5-[2-ethoxy-5-(4-ethylpiperazin-1-ylsulphonyl)-pyridin-3-yl]-2-methyl-2,6-dihydro-7H-pyrazolo[4,3-d]pyrimidin-7-one Sodium nutrite (12 mg, 0.18 mmol) was added to a cooled (−10 ° C.) solution of the title compound of preparation 120 (40 mg, 0.12 mmol) in acetic acid (0.45 ml) and concentrated hydrochloric acid (0.45 ml) and the solution allowed to warm to 0° C. over 2 hours. The solution was re-cooled to −20° C., liquid sulphur dioxide (0.36 ml) and a solution of copper (II) chloride (48 mg, 0.48 mmol) in water (2 ml) and acetic acid (1 ml) added, and the reaction then allowed to warm to room temperature over 2 hours. The mixture was extracted with dichloromethane, the combined organic extracts dried (Na₂SO₄), concentrated under reduced pressure and azeotroped with toluene. The brown residue was dissolved in ethanol (10 ml), N-ethylpiperazine (50 µl, 0.38 mmol) added and the reaction stirred at room temperature for 18 hours. The mixture was concentrated under reduced pressure and the crude product purified by column chromatography on silica gel using dichloromethane:methanol:0.88 ammonia (98:2:0.5) to give the title compound, (12 mg, 20%).

δ(CDCl₃): 1.02 (3H, t), 1.57 (6H, m), 2.41 (2H, q), 2.57 (4H, m), 3.12 (4H, m), 3.90 (3H, s), 4.74 (2H, q), 4.88 (2H, q), 8.60 (1H, d), 8.92 (1H, d), 10.56 (1H, s).

LRMS: m/z 492 (M+1)⁺

EXAMPLE 81

5-[2-n-Butoxy-5-(4ethylpiperazin-1-ylsulphonyl) pyridin-3-yl]-3-ethoxy-2-methyl-2,6-dihydro-7H-pyrazolo[4,3-d]pyrimidin-7-one Potassium bis(trimethylsilyl)amide (10 mg, 0.05 mmol) was added to a suspension of the title compound of example 80 (10 mg, 0.02 mmol) in n-butanol (4 ml), and the reaction mixture heated under reflux for 6 hours. The cooled mixture was evaporated under reduced pressure and the residue purified by column chromatography on silica gel using dichloromethane:methanol:0.88 ammonia (98:2:0.5) as eluant, to afford the title compound, (8 mg, 76%).

δ(CDCl$_3$): 1.02 (6H, t), 1.57 (5H, m), 1.96 (2H, m), 2.42 (2H, q), 2.56 (4H, m), 3.13 (4H, m), 3.90 (3H, s), 4.65 (2H, t), 4.88 (2H, q), 8.60 (1H, s), 8.90 (1H, s), 10.53 (1H, s).

LRMS: m/z 520 (M+1)$^+$

EXAMPLE 82

5-[2-Ethoxy-5-(4-ethylpiperazin-1-ylsulphonyl)-pyridin-3-yl]-3-(1-ethoxyvinyl)-2-methyl-2,6-dihydro-7H-pyrazolo[4,3-d]pyrimidin-7-one A mixture of the title compound or preparation 101 (100 mg, 0.19 mmol), lithium chloride (80 mg, 1.9 mmol), copper (I) iodide (6 mg, 0.03 mmol) and (1-ethoxyvinyl)(tri-n-butyl)stannane (90 mg, 0.247 mmol) in dioxan (10 ml) was de-gassed and placed under an atmosphere of nitrogen. Tetrakis(triphenylphosphine)palladium (0) (20 mg, 0.017 mmol) was added, and the reaction heated under reflux for 5 hours. The cooled mixture was concentrated under reduced pressure, and the residue stirred vigorously in a solution of ethyl acetate:10% aqueous potassium fluoride solution for 10 minutes. The resulting suspension was filtered through Arbocel®, and the filtrate separated. The organic layer was washed with 10% aqueous potassium fluoride solution, then brine, dried (MgSO$_4$) and evaporated under reduced pressure. The crude product was purified by medium pressure column chromatography on silica gel using an elution gradient of dichloromethane:methanol (100:0 to 98:2) to afford the title compound (84 mg, 85%) as a foam.

δ(CDCl$_3$): 1.02 (3H, t), 1.46 (3H, t), 1.58 (3H, t), 2.41 (2H, q), 2.57 (4H, m), 3.15 (4H, m), 4.02 (2H, q), 4.24 (3H, s), 4.69 (1H, d), 4.77 (2H, q), 5.23 (1H, d), 8.62 (1H, d), 9.06 (1H, d), 10.70 (1H, s).

LRMS: m/z 518 (M+1)$^+$

EXAMPLE 83

N,2-Dimethyl-5-[2-ethoxy-5(4-ethylpiperazin-1-ylsulphonyl)pyridin-3-yl)-7-oxo-6,7-dihydro-2H-pyrazolo[4,3-d]pyrimidin-3-carboxamide A mixture of the title compound of preparation 159 (50 mg, 0.108 mmol), acetyl chloride (7 μl, 0.108 mmol) and pyridine (9 μl, 0.11 mmol) in dichloromethane (2 ml) was stirred at room temperature for 18 hours. The reaction mixture was evaporated under reduced pressure and the residue purified by column chromatography on silica gel using an elution gradient of dichloromethane:methanol (100:0 to 80:20) to afford the title compound (45 mg, 82%).

δ(CDCl$_3$): 1.08 (3H, m), 1.58 (3H, t), 2.38 (3H, s), 2.44–2.70 (6H, m), 3.18 (4H, m), 4.01 (3H, s), 4.74 (2H, q), 8.60 (1H, d), 8.95 (1H, d), 10.67 (1H, s).

LRMS: m/z504 (M+2)$^+$

Biological Activity

Compound of the invention were found to have in vitro activities as inhibitors of cGMP PDE5 with IC$_{50}$ values of less than about 100 nM.

The following Table illustrates the in vitro activities for a range of compounds of the invention as inhibitors of cGMP PDE5.

| Example | IC$_{50}$ (nM) |
|---|---|
| 5 | 2.80 |
| 8 | 4.10 |
| 19 | 3.40 |
| 33 | 2.80 |
| 42 | 2.26 |

What is claimed is:
1. A compound of formula IA, or of formula IB:

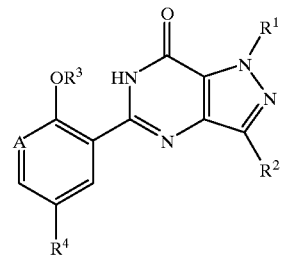

IA

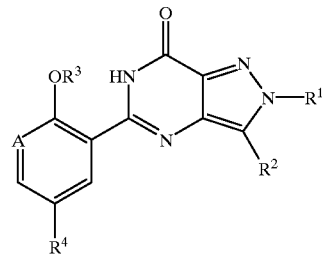

IB wherein
A represents CH or N;
R$^1$ represents H, lower alkyl, Het, alkylHet, aryl or alkylaryl, which latter five groups are all optionally substituted (and/or, in the case of lower alkyl, optionally terminated) by one or more substituents selected from halo, cyano, nitro, lower alkyl, OR$^5$, C(O)R$^6$, C(O)OR$^7$, C(O)NR$^8$R$^9$, NR$^{10a}$R$^{10b}$ and SO$_2$NR$^{11a}$R$^{11b}$;
R$^2$ represents C(O)NR$^{12}$R$^{13}$, C(O)OR$^{12}$, NR$^{12}$R$^{13}$, N(H)SO$_2$R$^{12}$, N(H)SO$_2$NR$^{12}$R$^{13}$,
N(H)C(O)R$^{12}$, OR$^{12a}$, lower alkyl (which alkyl group is interrupted by one or more of O, S or N(R$^{12}$) and/or substituted or terminated by C(O)NR$^{12}$R$^{13}$, C(O)OR$^{12}$ or aryl or Het$^1$), cyano, aryl or Het$^1$, provided that, in a compound of formula IA wherein R$^2$ is alkoxy, A must be N;
R$^3$, R$^{12}$ and R$^{13}$ independently represent H or lower alkyl, which alkyl group is optionally substituted and/or optionally terminated by one or more substituents selected from aryl,
Het, halo, cyano, nitro, OR$^5$, C(O)R$^6$, C(O)OR$^7$, C(O)NR$^8$R$^9$, NR$^{10a}$R$^{10b}$ and SO$_2$N$^{11a}$R$^{11b}$;
R$^4$ represents SO$_2$NR$^{14}$R$^{15}$;
R$^{14}$ and R$^{15}$, together with the nitrogen to which they are attached, form Het;
Het represents an optionally substituted four- to twelve-membered heterocyclic group, which group contains at least one nitrogen atom and, optionally, one or more further heteroatoms selected from nitrogen, oxygen and sulphur;

Het$^1$ represents an optionally substituted four- to twelve-membered heterocyclic group, which group contains at least one nitrogen atom or at least one oxygen atom and, optionally, one or more further heteroatoms selected from nitrogen, oxygen and sulphur; and $R^5$, $R^6$, $R^7$, $R^8$, $R^9$, $R^{11a}$, $R^{11b}$ and $R^{12a}$ independently represent, at each occurrence when used herein, H or lower alkyl;

$R^{10a}$ and $R^{10b}$, at each occurrence when used herein, either independently represent, H or lower alkyl or, together with the nitrogen atom to which they are attached, represent azetidinyl, pyrollidinyl or piperidinyl;

or a pharmaceutically, or a veterinarily, acceptable derivative thereof.

2. A compound as claimed in claim 1, wherein $R^1$ represents H, a linear, branched, cyclic, acyclic and/or part cyclic/acyclic lower alkyl group, alkylHet, or alkylaryl.

3. A compound as claimed in claim 1, wherein $R^2$ represents a linear or branched, optionally unsaturated lower alkyl group (which alkyl group is optionally interrupted by one or more of O, S or N($R^{12}$)), C(O)N$R^{12}R^{13}$, N$R^{12}R^{13}$, N(H)C(O)$R^{12}$, O$R^{12a}$, aryl or Het$^1$.

4. A compound as claimed claim 1, wherein $R^3$ represents linear, branched, cyclic and/or acyclic lower alkyl which is optionally substituted or terminated by one or more substituents selected from Het or O$R^5$.

5. A compound as claimed in claim 1, wherein $R^{12}$ and $R^{13}$ independently represent H, or linear or branched lower alkyl, provided that, in the case where $R^2$ represents N$R^{12}R^{13}$, $R^{12}$ and $R^{13}$ do not both represent H.

6. A compound as claimed in any one of the preceding claims, wherein $R^{14}$ and $R^{15}$, together with the nitrogen to which they are attached represent 4-$R^{16}$-piperazinyl, in which $R^{16}$ represents H or lower allyl, which latter group is optionally substituted or terminated by one or more substituents selected from aryl, Het, halo, cyano, nitro, O$R^5$, C(O)$R^6$, C(O)O$R^7$, C(O)N$R^8R^9$, N$R^{10a}$, $R^{10b}$, SO$_2$N$R^{11a}R^{11b}$ and N(H)SO$_2R^{12}$ wherein $R^5$, $R^6$, $R^7$, $R^8$, $R^9$, $R^{10a}$, $R^{10b}$, $R^{11a}$, $R^{11b}$ and $R^{12}$ are as defined in claim 1.

7. A formulation comprising a compound as defined in claim 1 in admixture with a pharmaceutically or veterinarily acceptable adjuvant, diluent or carrier.

8. A formulation as claimed in claim 7, which is a pharmaceutical formulation.

9. A formulation as claimed in claim 7, which is a veterinary formulation.

10. A method of treating or preventing a medical condition for which inhibition of cGMP PDE5 is desired, which comprises administering a therapeutically effective amount of a compound as defined in claim 1 to a patient in need of such treatment.

11. A method as claimed in claim 10, wherein the condition is male erectile dysfunction, female sexual dysfunction, premature labor, dsymenorrhoea, benign prostatic hyperplasia (BPH), bladder outlet obstruction, incontinence, stable or unstable variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma, a disease characterised by disorders of gut motility, pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer metastasis, baldness, nutcracker oesophagus, anal fissure and hypoxic vasoconstriction.

* * * * *